United States Patent
Uchimura et al.

(10) Patent No.: US 7,942,810 B2
(45) Date of Patent: May 17, 2011

(54) ENDOSCOPE AND ENDOSCOPIC SYSTEM

(75) Inventors: Sumihiro Uchimura, Sagamihara (JP); Fumiyuki Onoda, Tama (JP); Toshiaki Noguchi, Tachikawa (JP); Akira Taniguchi, Hachioji (JP); Katsuya Suzuki, Sagamihara (JP)

(73) Assignee: Olympus Corporation, Tokyo (JP)

( * ) Notice: Subject to any disclaimer, the term of this patent is extended or adjusted under 35 U.S.C. 154(b) by 1300 days.

(21) Appl. No.: 11/510,767

(22) Filed: Aug. 25, 2006

(65) Prior Publication Data

US 2006/0293562 A1 Dec. 28, 2006

Related U.S. Application Data

(63) Continuation of application No. PCT/JP2005/003327, filed on Feb. 28, 2005.

(30) Foreign Application Priority Data

Feb. 26, 2004 (JP) .................................. 2004-052327
Apr. 21, 2004 (JP) .................................. 2004-125758
Apr. 21, 2004 (JP) .................................. 2004-125759

(51) Int. Cl.
*A61B 1/00* (2006.01)
*A61B 1/04* (2006.01)

(52) U.S. Cl. ....................................... 600/117; 600/146

(58) Field of Classification Search ................... 600/103, 600/117–118, 145–146

See application file for complete search history.

(56) References Cited

U.S. PATENT DOCUMENTS

| 4,158,310 | A | * | 6/1979 | Ho .................................. 73/705 |
| 4,292,961 | A | * | 10/1981 | Kawashima .................. 600/145 |
| 4,569,335 | A | * | 2/1986 | Tsuno .......................... 600/158 |
| 4,576,146 | A | * | 3/1986 | Kawazoe et al. ............. 600/117 |
| 4,784,811 | A | * | 11/1988 | Hirschfeld .................... 264/1.27 |
| 4,982,725 | A | * | 1/1991 | Hibino et al. ................. 600/117 |
| 5,351,677 | A | * | 10/1994 | Kami et al. .................... 600/109 |
| 5,469,840 | A | * | 11/1995 | Tanii et al. .................... 600/117 |
| 5,888,191 | A | | 3/1999 | Akiba et al. |
| 5,891,014 | A | | 4/1999 | Akiba |
| 2003/0069475 | A1 | | 4/2003 | Banik et al. |

FOREIGN PATENT DOCUMENTS

| JP | 56-023077 | 3/1981 |
| JP | 4-272739 | 9/1992 |
| JP | 5-13401 | 2/1993 |
| JP | 07-124104 | 5/1995 |
| JP | 07-327922 | 12/1995 |

(Continued)

OTHER PUBLICATIONS

Japanese Office Action dated Feb. 16, 2010.

*Primary Examiner* — Philip R Smith
(74) *Attorney, Agent, or Firm* — Scully, Scott, Murphy & Presser, P.C.

(57) ABSTRACT

An endoscope of the present invention includes an insert section inserted in a subject body, an operation section provided at a base end of the insert section, a control process section provided in the operation section, for controlling an image pickup section for capturing a subject body image and a predetermined function in the operation section, a signal circuit extending from the control process section, and a connection section provided to the operation section, for allowing detachable connection of a tube unit through which at least one duct line is inserted.

12 Claims, 50 Drawing Sheets

FOREIGN PATENT DOCUMENTS

| | | |
|---|---|---|
| JP | 10-201706 | 8/1998 |
| JP | 10-258020 | 9/1998 |
| JP | 10-295635 | 11/1998 |
| JP | 11-032988 | 2/1999 |
| JP | 11-299724 | 11/1999 |
| JP | 2001-299697 | 10/2001 |
| JP | 2002-369789 | 12/2002 |

* cited by examiner

WIRED METHOD

OPTICAL COMMUNICATION METHOD

ENLARGED VIEW

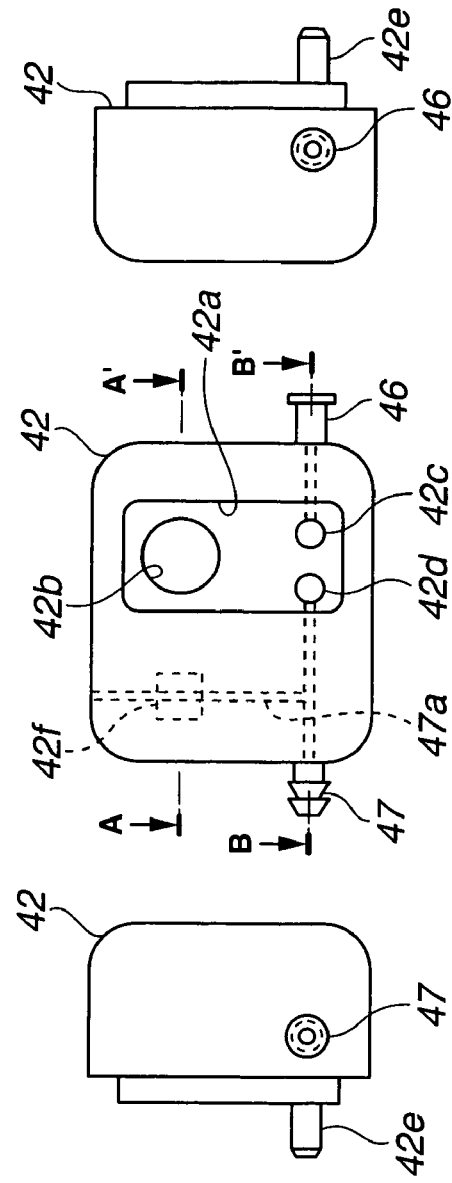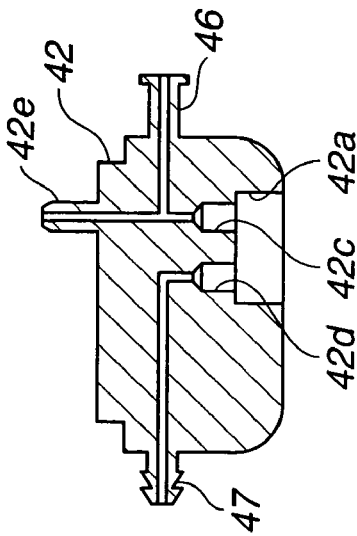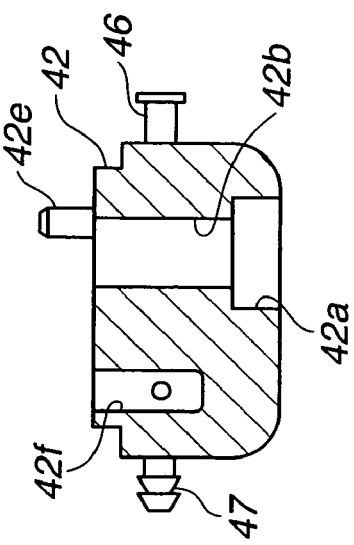

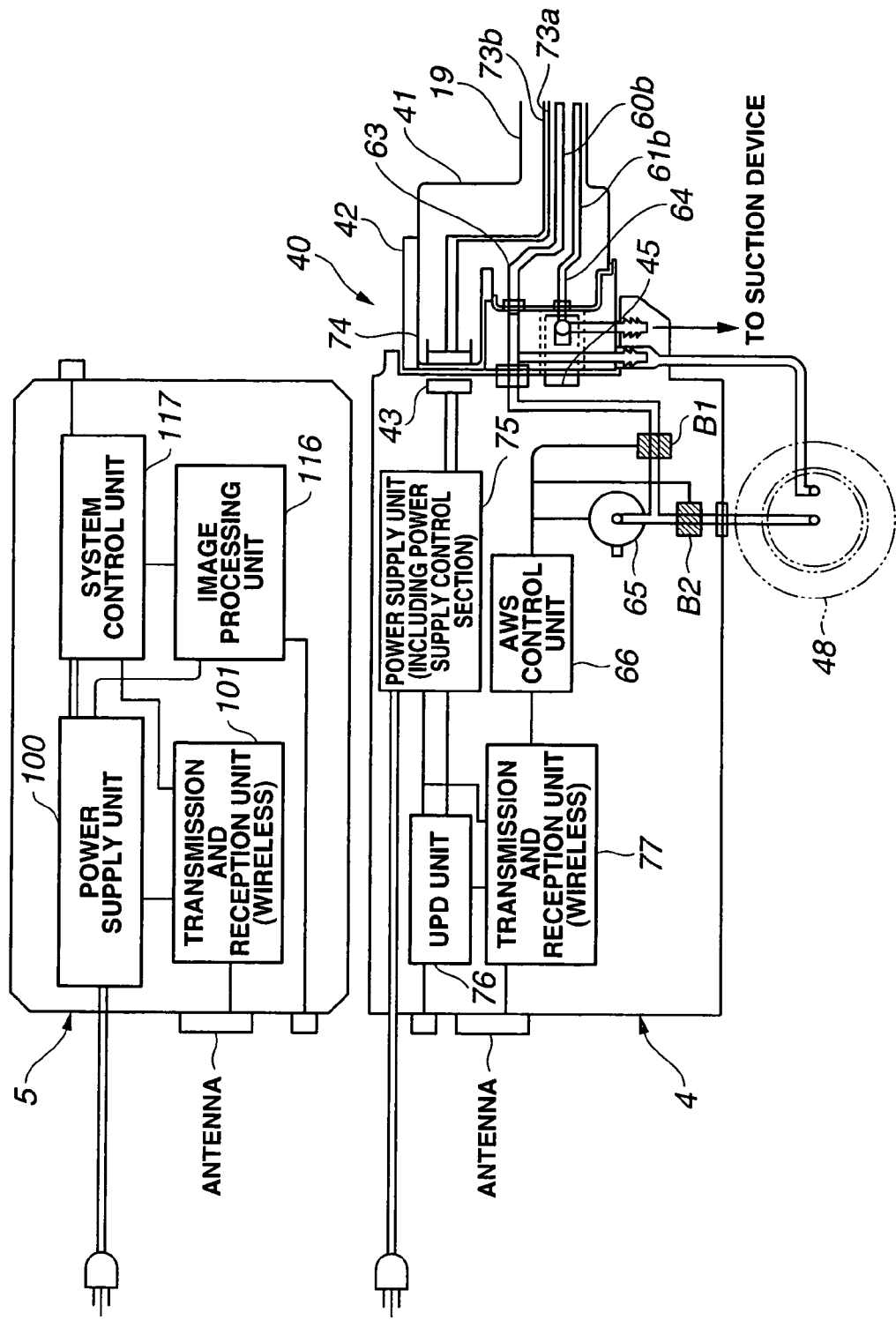

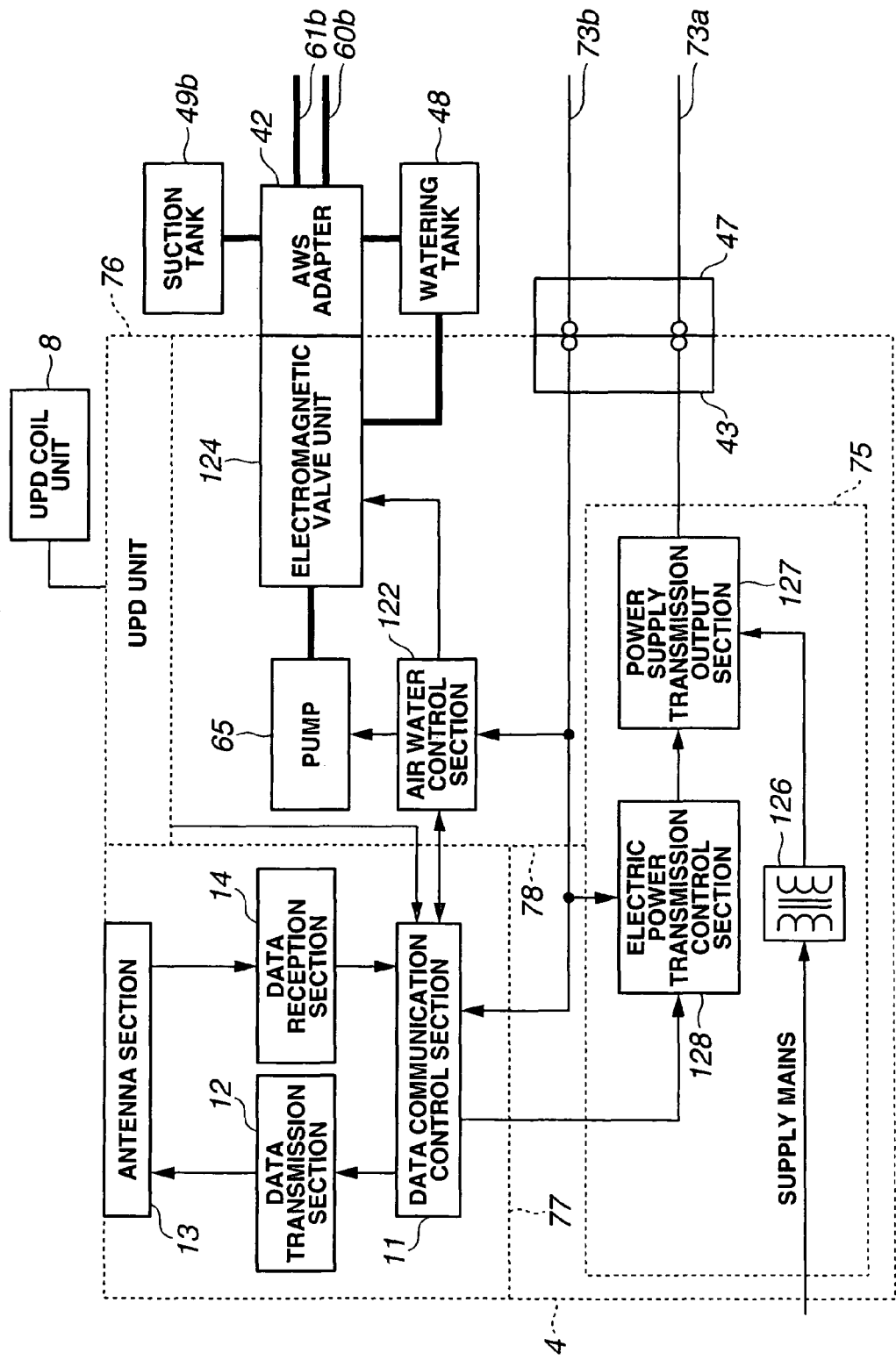

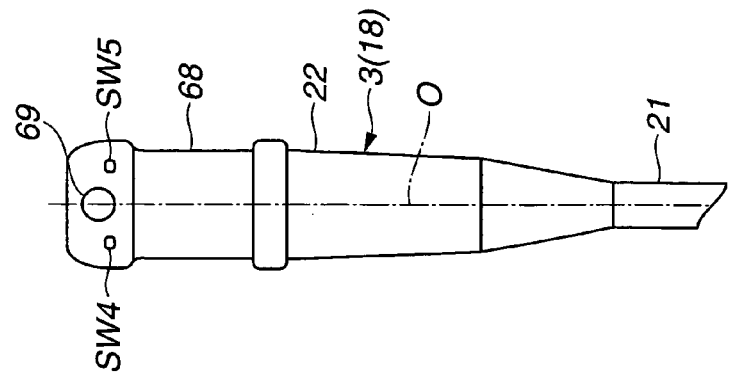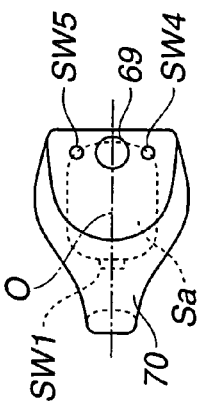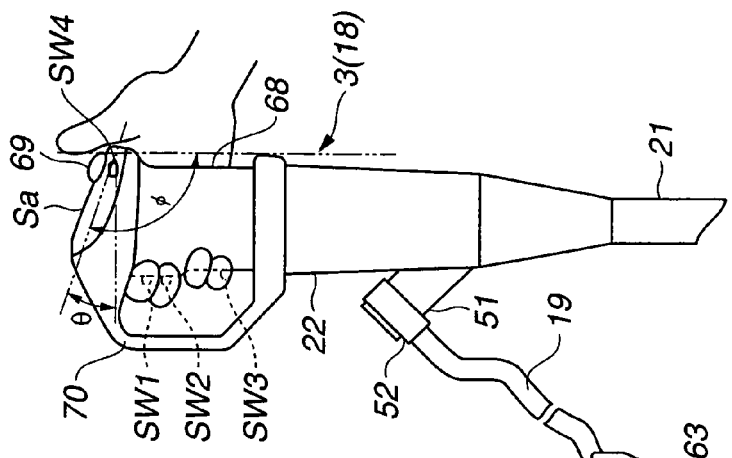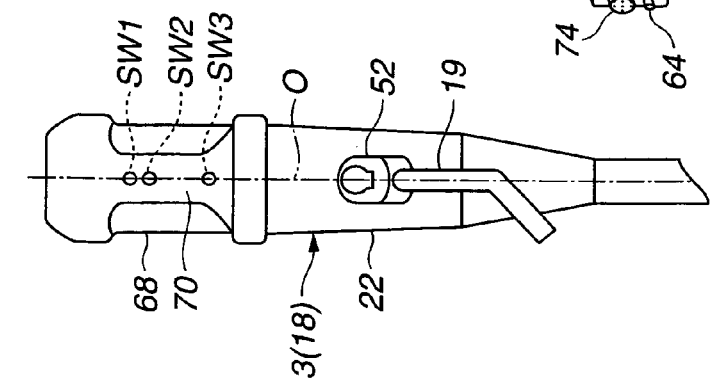

ENLARGED VIEW

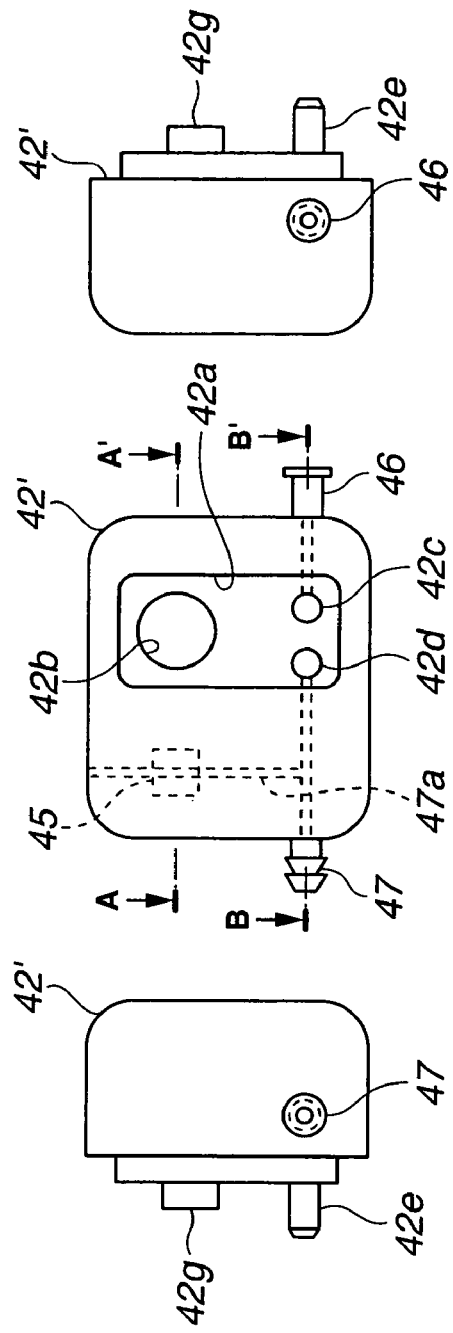

ENDOSCOPE AND ENDOSCOPIC SYSTEM

CROSS REFERENCE TO RELATED APPLICATION

This application is a continuation application of PCT/JP2005/003327 filed on Feb. 28, 2005 and claims benefit of Japanese Applications No. 2004-052327 filed in Japan on Feb. 26, 2004, No. 2004-125758 filed in Japan on Apr. 21, 2004, and No. 2004-125759 filed in Japan on Apr. 21, 2004, the entire contents of which are incorporated herein by their reference.

BACKGROUND OF THE INVENTION

1. Field of the Invention

The present invention relates to an endoscope to be inserted in a body cavity or the like for performing an endoscopy or the like and an endoscopic system having the endoscope.

2. Description of the Related Art

In recent years, endoscopes having an image pickup element built in an insert section are widely used for an inspection of a body cavity, a therapy with use of an endotherapy product, etc.

As an endoscope having such a built-in image pickup element and a flexible insert section, there is known one including a light guide for transmitting illumination light from an operation section provided on a rear end of the insert section and a universal cable through which a signal line connected to the image pickup element is inserted.

Regarding an endoscope of this type, such an endoscope is also known in which by providing to the operation section operation buttons, switches, or the like for performing various control operations, various controls can be performed by the operation section.

However, with the above-mentioned endoscopes, although the various controls can be performed by providing a large number of operations buttons, switches, etc., it is accordingly necessary to insert many signal lines through the universal cable. Thus, the thickness of the universal cable is increased, and this thick universal cable may disturb the operations.

In addition, when the endoscope is provided with numerous various functions, it is necessary to insert signal lines corresponding to the varying functions through the universal cable. Thus, problems arise in that extension is difficult and the production cost is raised.

Meanwhile, for example, as disclosed in Japanese Unexamined Patent Application Publication No. 2002-369789, an endoscope having such a structure that a universal cable through which a light guide for transmitting illumination light is inserted is set detachably connected, and an optical cable is inserted together with this light guide, whereby an image pickup signal or the like captured by an image pickup element is transmitted to a signal processing device outside the endoscope. However, a function of supplying a fluid through a duct line, such as an air water process, cannot be realized, so there is a problem of significantly decreasing an observation function, and the like.

Also, in general, an endoscope including a flexible insert section is provided with a bending section at a distal end of the insert section for allowing insertion into a bending body or the like and observation in a desired direction, and a bending operation section in the operation section at hand side for performing a bending operation (articulation operation) on the bending section.

By bending the bending section in this way, it becomes easier to insert the insert section in a bending body cavity.

Then, in order to improve the insertability, it is convenient if a state where the bending section is pressed against an inner wall or the like can be detected. In this case, the bending section may include an electric pressure-sensitive sensor. The endoscope always needs an illumination section, if a part of the illumination light can be used, this becomes an extremely useful application method.

In an electronic endoscope of Japanese Unexamined Patent Application Publication No. 7-124104, a pressure-sensitive sensor composed of a warpage gauge for detecting a pressure is provided at a bending section, and a bending operation by a bending operation section is regulated on the basis of an output of this pressure-sensitive sensor.

According to the example of Japanese Unexamined Patent Application Publication No. 7-124104, the pressure detection is electrically performed, and therefore the above-mentioned illumination light is not effectively used.

An endoscope for a medical field is especially used by being inserted in a body cavity for the purpose of inspection and therapy, and thus the endoscope needs to be cleaned and disinfected. When the endoscope is cleaned and disinfected, an endoscope washer is used. The endoscope is set in a cleaning tank of the endoscope washer, for cleaning, disinfection, rinsing, and draining.

In addition, the endoscope accommodates a plurality of duct lines including an air water duct line and a biopsy port. A cleaning solution and a disinfectant solution need sufficiently pass through these duct lines, and cleaning, disinfection, and the like need to be reliably performed for the duct lines.

An endoscope washer for detecting whether or not cleaning and disinfection are appropriately performed for the various duct lines provided inside the endoscope is proposed, for example, in Japanese Unexamined Patent Application Publication No. 2001-299697.

However, in the endoscope washer disclosed in the above-mentioned publication, whether or not the duct lines in the endoscope are appropriately subjected to cleaning and the like is determined on the basis of a flow amount value detected by a flow amount sensor provided to the endoscope washer. As the sensor for detecting the contamination is provided to the endoscope washer, the contamination inside the endoscope can be detected only when cleaning and the like are conducted.

SUMMARY OF THE INVENTION

The present invention has been made in view of the above-mentioned problems and it is therefore an object to provide an endoscope with which a satisfactory operability can be ensured without decreasing an observation function even when operation parts such as a bending operation switch and an air water switch are provided to an operation section.

An endoscope according to an aspect of the present invention includes an insert section inserted in a subject body, an operation section provided at a base end of the insert section, a control process section provided in the operation section, for controlling an image pickup section for capturing a subject body image and a predetermined function in the operation section, a signal circuit extending from the control process section, and a connection section provided to the operation section, for allowing detachable connection of a tube unit through which at least one duct line is inserted.

BRIEF DESCRIPTION OF THE DRAWINGS

FIG. 7A is a front view showing a structure of the AWS adapter in the endoscopic system according to the first embodiment.

FIG. 7B is a side view showing a structure of the AWS adapter in the endoscopic system according to the first embodiment.

FIG. 7C is another side view showing a structure of the AWS adapter in the endoscopic system according to the first embodiment.

FIG. 7D is a cross-sectional view showing a structure of the AWS adapter in the endoscopic system according to the first embodiment.

FIG. 7E is another cross-sectional view showing a structure of the AWS adapter in the endoscopic system according to the first embodiment.

FIG. 8 shows a structure of the AWS adapter in the endoscopic system according to the first embodiment.

FIG. 15 is a block diagram showing an electric structure of an AWS unit in the endoscopic system according to the first embodiment.

FIG. 46A is a side view showing a specific outer appearance shape of the endoscope in the endoscopic system according to the seventh embodiment.

FIG. 46B is a front view showing the specific outer appearance shape of the endoscope in the endoscopic system according to the seventh embodiment.

FIG. 46C is a back view showing the specific outer appearance shape of the endoscope in the endoscopic system according to the seventh embodiment.

FIG. 46D is a plan view showing the specific outer appearance shape of the endoscope as seen from the front in the endoscopic system according to the seventh embodiment.

FIG. 46E is a main part enlarged view showing an example of a nearly optimal angle range of an inclined surface in the endoscope in the endoscopic system according to the seventh embodiment.

FIG. 50A is a front view of a structure of the AWS adapter in the endoscopic system according to the seventh embodiment.

FIG. 50B is a side view of the structure of the AWS adapter in the endoscopic system according to the seventh embodiment.

FIG. 50C is another side view of the structure of the AWS adapter in the endoscopic system according to the seventh embodiment.

FIG. 50D is a cross-sectional view of the structure of the AWS adapter in the endoscopic system according to the seventh embodiment.

FIG. 50E is another cross-sectional view of the structure of the AWS adapter in the endoscopic system according to the seventh embodiment.

DESCRIPTION OF THE PREFERRED EMBODIMENTS

Hereinafter, a description will be given of preferred embodiments of the present invention with reference to the drawings.

Figure 1:
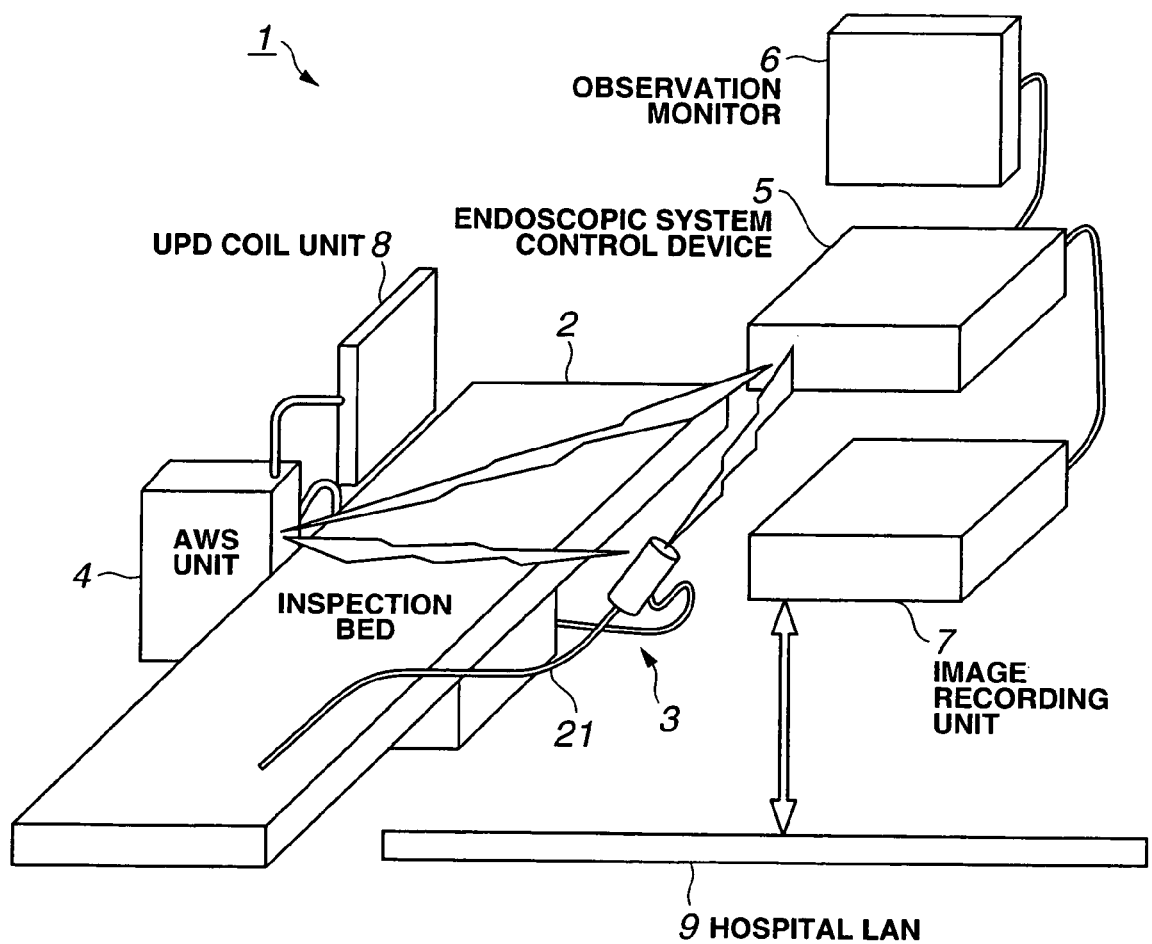
FIG. 1 shows a schematic structure of an endoscopic system according to a first embodiment of the present invention.
Figure 2A:
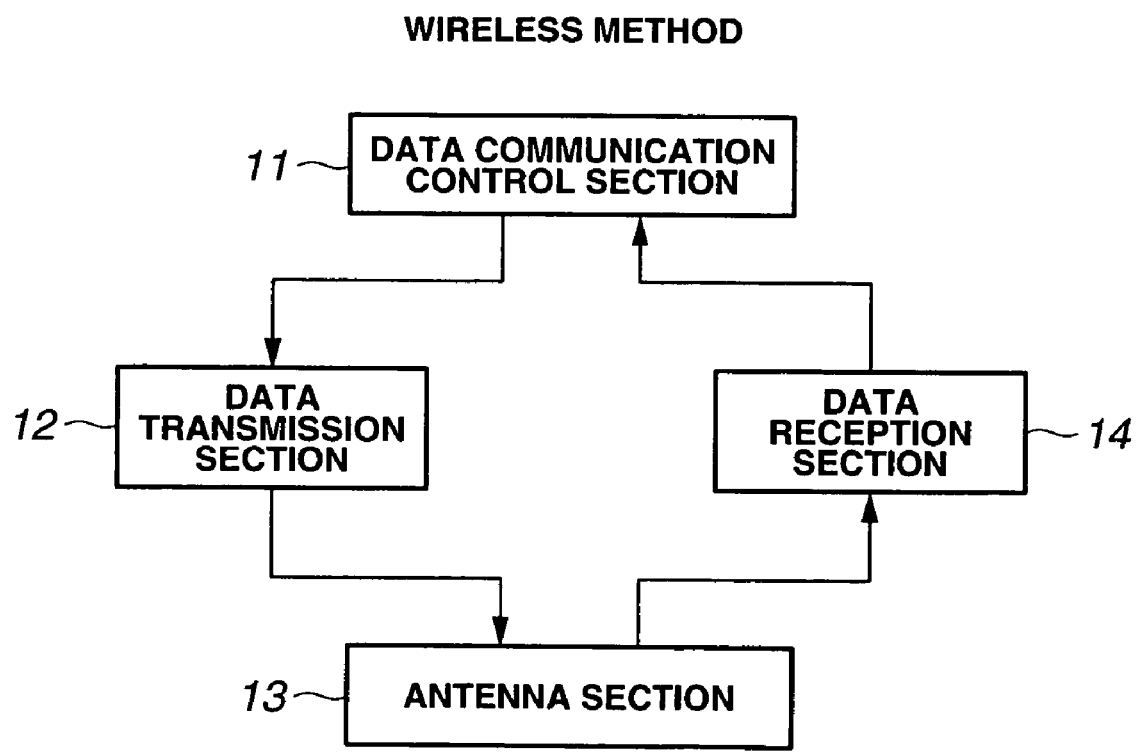
FIG. 2A is a block diagram showing an example of data communication mode in the endoscopic system according to the first embodiment.
Figure 2B:
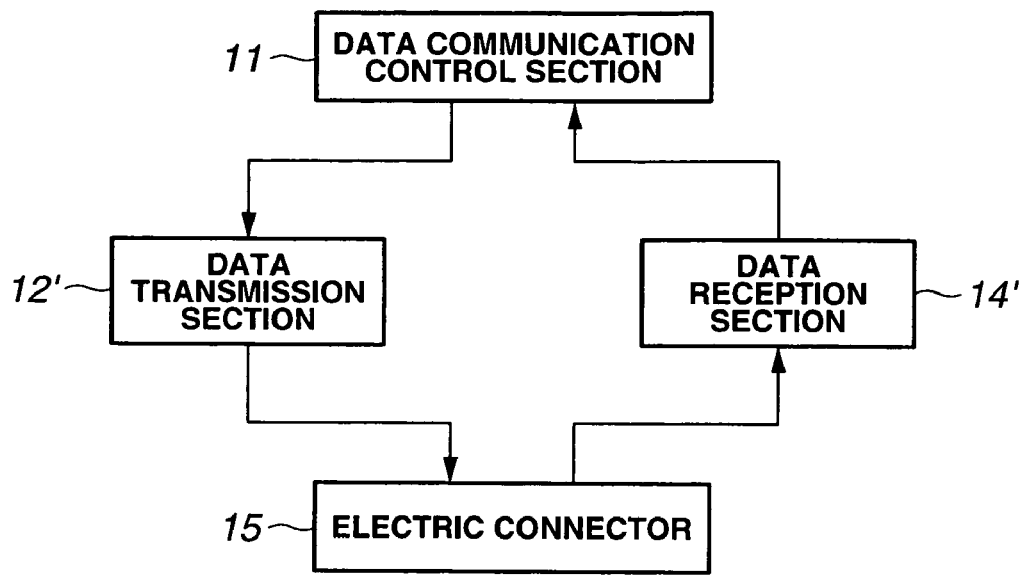
FIG. 2B is a block diagram showing an example of the data communication mode in the endoscopic system according to the first embodiment.
Figure 2C:
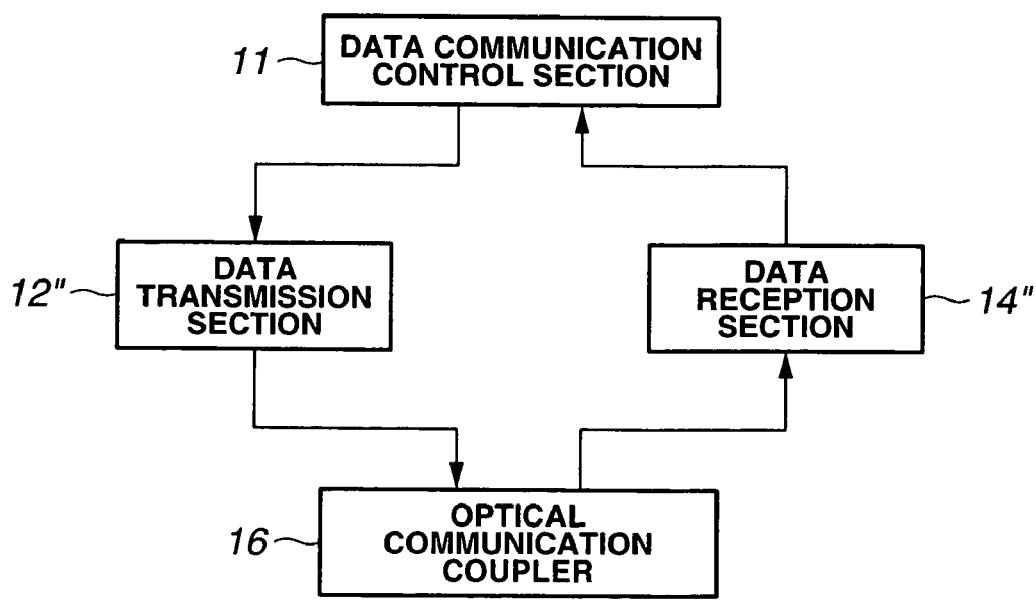
FIG. 2C is a block diagram showing an example of the data communication mode in the endoscopic system according to the first embodiment.
Figure 3:
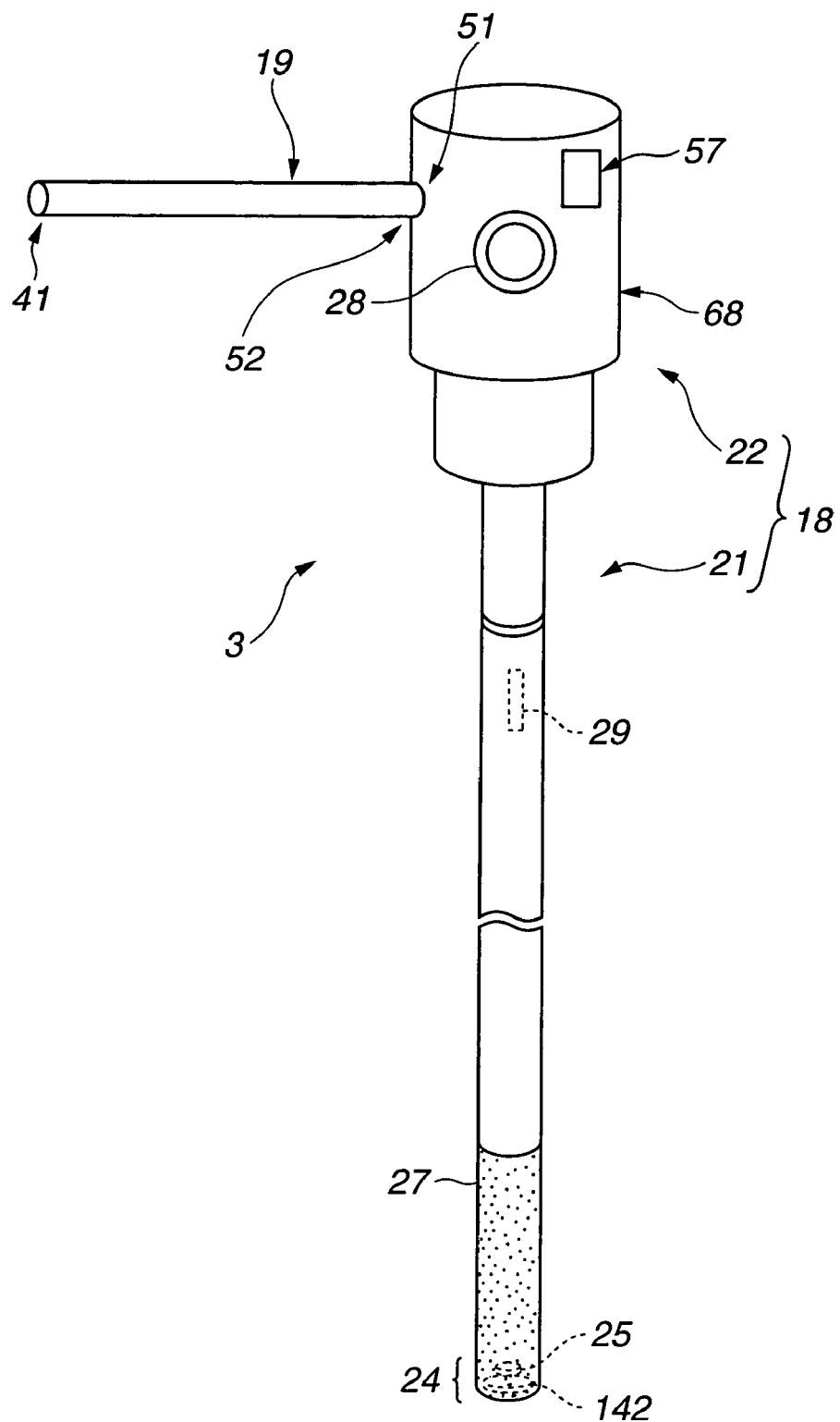
FIG. 3 is an outer appearance perspective view showing a schematic structure of the endoscope in the endoscopic system according to the first embodiment.

Before a specific structure of an endoscopic system according to a first embodiment of the present invention is described, a description is first given of a schematic structure of the endoscopic system with reference to FIGS. 1 to 3.

FIG. 1 shows a schematic structure of an endoscopic system according to the first embodiment of the present invention, FIGS. 2A to 2C are block diagrams showing each example of data communication mode in the endoscopic system according to the first embodiment, and FIG. 3 is an outer appearance perspective view showing a schematic structure of the endoscope in the endoscopic system according to the first embodiment.

As shown in FIG. 1, an endoscopic system 1 includes a flexible endoscope (also referred to as scope) 3 for performing an endoscopic inspection by inserting the endoscope in a body cavity of a patient (not shown) lying on an inspection bed 2. The endoscopic system 1 includes air water supply/suction unit having functions of airing, watering, and suction (hereinafter, abbreviated as AWS unit) 4, an endoscopic system control device 5 for performing a part of signal process on an image pickup element built in the endoscope 3 and a part of control process, on various operation sections provided to the endoscope 3, and an observation monitor 6 for displaying a video signal generated by the endoscopic system control device 5 such as a liquid crystal monitor, which are connected to the endoscope 3.

In addition, the endoscopic system 1 further includes an image recording unit 7 for filing digital video signals, for example, generated by the endoscopic system control device 5, and a UPD coil unit 8 connected to the AWS unit 4, for displaying, when shape detecting coils (hereinafter, abbreviated as UPD coil) are built in the insert section of the endoscope 3, a shape of the insert section of the endoscope 3 by detecting each position of the UPD coils while a signal of a magnet field is received by the UPD coil.

Then, the image recording unit 7 is connected to a LAN 9 in a hospital where the endoscopic system 1 is provided. With use of the respective terminal devices connected to the LAN 9 in a wired or wireless way, images and the like filed in the image recording unit 7 can be referenced to.

Also, as shown in FIG. 1, the AWS unit 4 and the endoscopic system control device 5 wirelessly perform transmission and reception of predetermined information. It should be noted that in FIG. 1, the endoscope 3 is connected to the AWS unit 4 via a cable, but may wirelessly perform transmission and reception (bidirectional transmission) of information. Then, the endoscopic system control device 5 may wirelessly perform direct transmission and reception with the endoscope 3.

FIGS. 2A to 2C show three methods in a transmission and reception unit (communication section) for performing data transmission and reception between a unit and a device in the endoscopic system 1 or between the endoscope 3 and a unit or a device. In FIG. 2A, as a specific example, the case of the AWS unit 4 and the endoscopic system control device 5 will be described.

FIG. 2A shows a wireless method, in which with a data communication control section 11 built in the AWS unit 4, transmission data is modulated via a data transmission section 12 and wirelessly sent to the endoscopic system control device 5 from an antenna section 13.

Then, the AWS unit 4 receives the wirelessly transmitted data from the endoscopic system control device 5 side at the antenna section 13, and sends the data which is demodulated by a data reception section 14, to the data communication control section 11. According to the present invention, when the data is transmitted in the wireless method, a wireless LAN is formed which has the maximum data communication speed of 54 Mbps on the basis of the IEEE802.1 lg standard, for example.

FIG. 2B shows a wired method. As a specific example, a case of performing data transmission and reception between the endoscope 3 and the AWS unit 4 will be described. With the data communication control section 11 built in the endoscope 3, the data transmitted from the endoscope 3 is received via a data transmission section 12' by the AWS unit 4 from an electric connector 15 in a wired way. Then, the data transmitted from the AWS unit 4 is sent via the electric connector 15 and a data reception section 14' to the data communication control section 11.

FIG. 2C shows an optical communication system. As a specific example, a case of performing data transmission and reception between the AWS unit 4 and the endoscopic system control device 5 will be described. The data communication control section 11 built in the AWS unit 4 is connected via a data transmission section 12" and a data reception section 14" for performing transmission and reception by using light, to an optical communication coupler 16 provided in the AWS unit 4, and performs data transmission and reception via an optical communication coupler on the endoscopic system control device 5 side.

As shown in FIG. 3, the endoscope 3 includes an endoscope main body 18 and a tube unit 19 one end of which is detachably connected to the endoscope main body 18 and the other end of which is connected to the AWS unit 4.

The endoscope main body 18 includes a flexible insert section 21 inserted in the body cavity, and an operation section 22 provided at a rear end of the insert section 21.

The operation section 22 includes a grasping section 68. Then, the grasping section 68 accommodates a control circuit 57 for governing a part of controls such as various operations in the operation section 22. It should be noted that a predetermined power supply line and a signal line are extended from the control circuit 57.

In addition, a predetermined tube extended from the insert section 21 is arranged in the operation section 22.

Furthermore, an overall connecter section 52 and a connector section 51 to be connected to the overall connecter section 52 in the tube unit 19 are arranged in the operation section 22 of the endoscope main body 18.

On the other hand, the tube unit 19 has at one end, the overall connecter section 52 connected to the connector section 51 arranged, which can be connected in a characteristic connection status to the connector section 51. Also, the tube unit 19 has at the other end, an endoscope connector 41 arranged and thus can be connected to the AWS unit 4.

Inside the tube unit 19, a plurality of predetermined tubes, electric lines, and signal lines unique to the endoscope device are arranged.

The endoscope main body 18 and the tube unit 19 are, as described above, connected via the connector section 51 and the overall connecter section 52. With the mutual connection of these connectors, the above-mentioned tubes are mechanically connected to each other, and the power supply lines and the signal lines characteristically have so-called electromagnetic coupling connection.

Also, in this embodiment, the tube unit 19 adopts a disposal tube having a diameter smaller than a conventional universal cable.

It should be noted that a detailed description will be given of the endoscope 3, including the connection between the connector section 51 and the overall connecter section 52 which can be connected in a characteristic connection status, with reference to FIG. 9.

Then, an image pickup unit using a CCD 25 for varying a gain inside the image pickup element is arranged at a distal end section 24 of the insert section 21 as the image pickup element. In addition, a contact sensor 142 for detecting a state in which the distal end section 24 contacts (is pressuring against) an inner wall or the like of the body cavity is arranged at the distal end section 24.

A bending section 27 which can be bent with a small power is provided at a rear end of the distal end section 24. By operating an articulation/remote control operator 28 provided at the operation section 22, the bending section 27 can be bent. The articulation/remote control operator 28 is structured so as to perform an articulation operation (bending operation), operations for airing, watering, suction, and the like, remote operations as a remote control operation for the endoscopic system control device 5, etc. (specifically, a freeze instruction operation and a release instruction operation). Also, a portion where the consistency can be varied is formed in the insertion section 21, whereby the insertion or the like can be smoothly performed.

Moreover, a washing level detecting section 29 is provided inside the insert section 21, making it possible to detect a washing level or the like of the duct line.

Next, with reference to FIGS. 4 to 8 and the like, a further specific structure of the endoscopic system 1 will be described.

Figure 4:
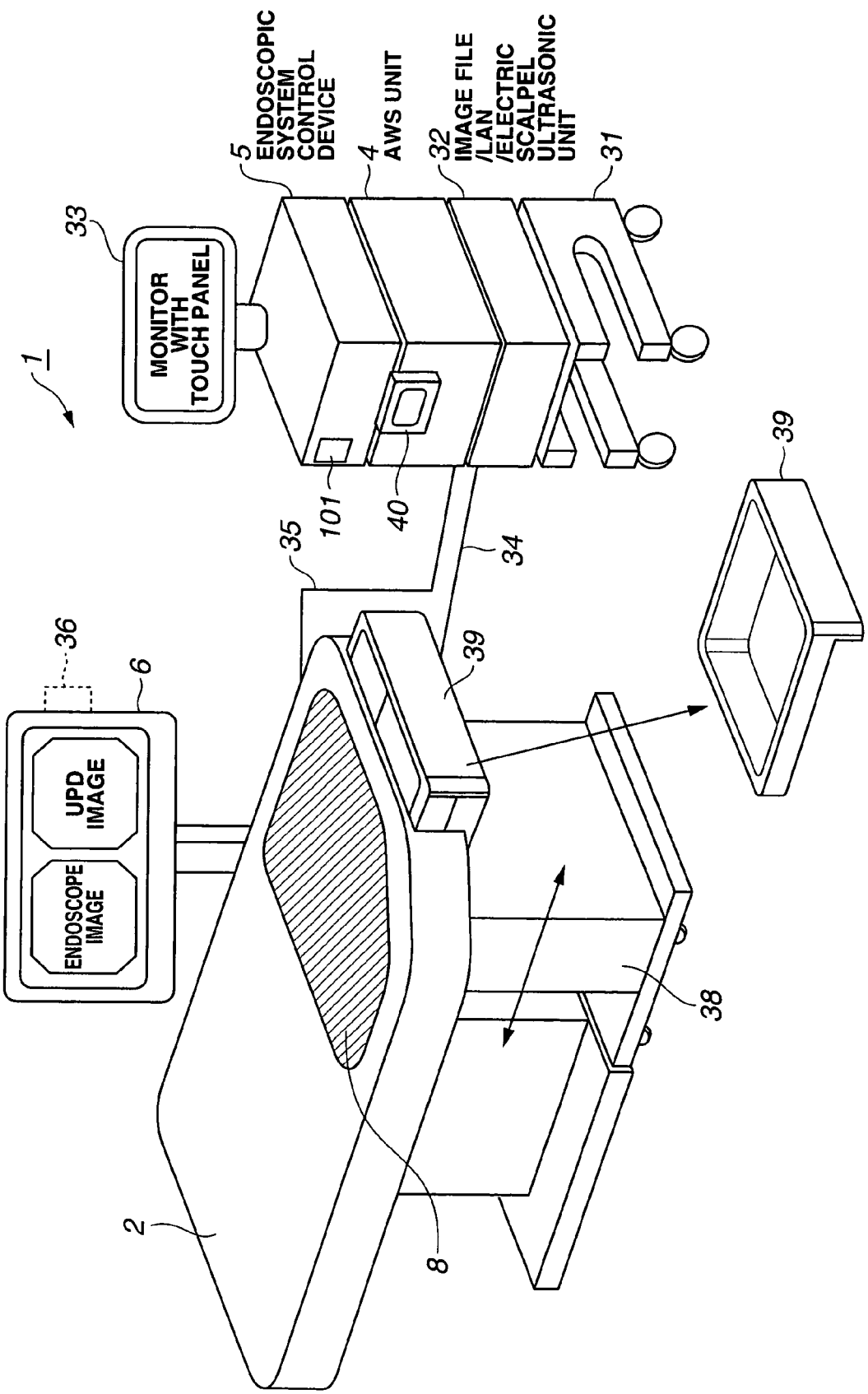
FIG. 4 is an outer appearance perspective view showing a further detailed structure of the endoscopic system according to the first embodiment.
Figure 5:
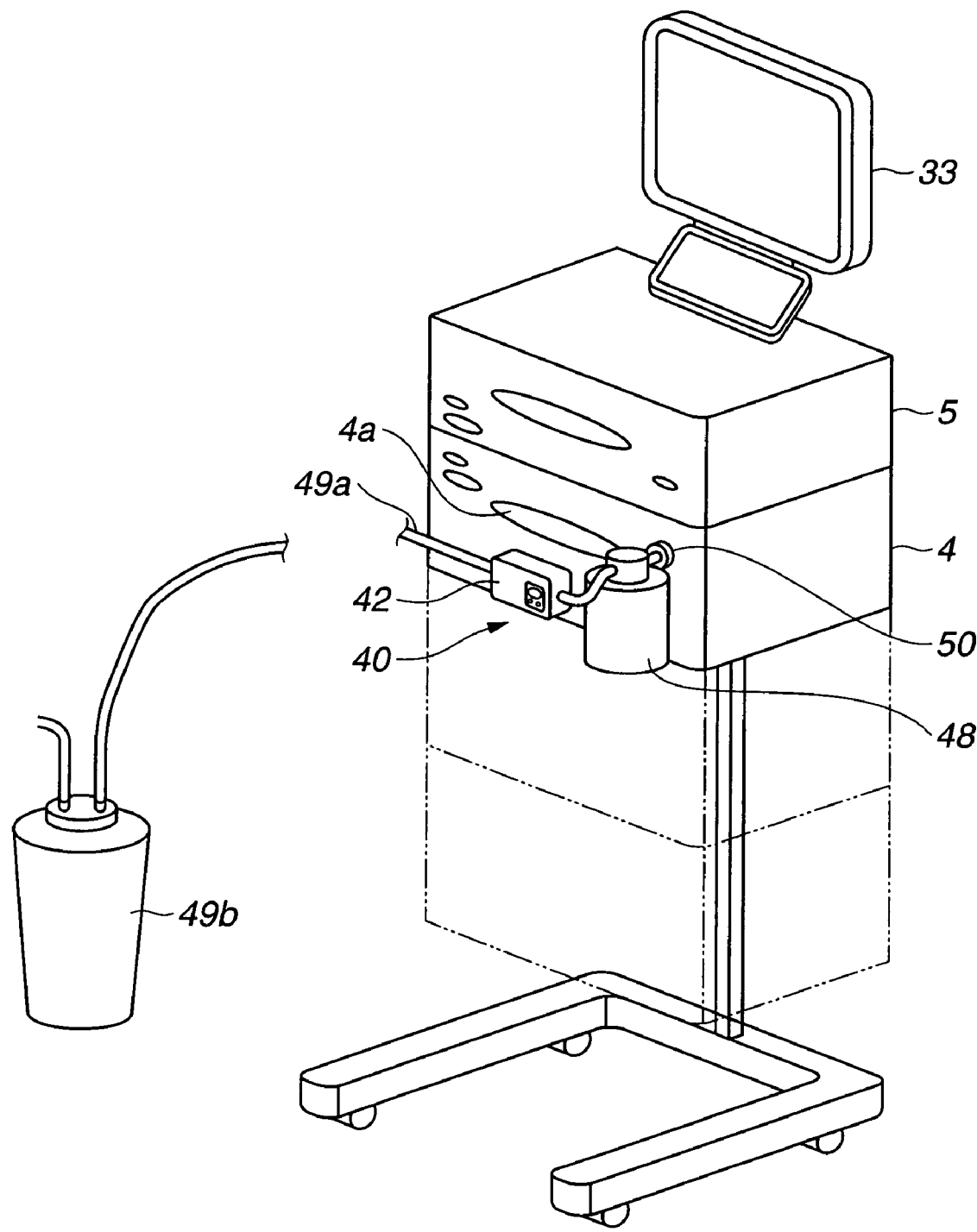
FIG. 5 is a perspective view showing a specific appearance shape of an AWS unit periphery section in the endoscopic system according to the first embodiment.

FIG. 4 is an outer appearance perspective view showing a further detailed structure of the endoscopic system according to the first embodiment. FIG. 5 is a perspective view showing a specific appearance shape of an AWS unit periphery section in the endoscopic system according to the first embodiment. FIGS. 6 are perspective views showing states in which a detachable AWS adapter is attached to and removed from the AWS unit in the endoscopic system according to the first embodiment. FIGS. 7A to 7E show internal structures of a control device and the AWS unit and a structure of a connection section of an endoscope connecter in the endoscopic system according to the first embodiment. FIG. 8 is a view showing a structure of the AWS adapter in the endoscopic system according to the first embodiment.

An observation monitor 6 composed of a liquid crystal monitor or the like is arranged adjacent to a side surface of the inspection bed 2. On a cart 31 arranged freely movable in the vicinity of one end section in a longitudinal direction of the inspection bed 2, the endoscopic system control device 5, the AWS unit 4, an image file/LAN/electric scalpel/ultrasonic unit (an image file unit, a wireless LAN or wired LAN, an electric scalpel device, an ultrasonic unit, and the like are abbreviated for representation) 32 are arranged, and on a top section thereof, the monitor 33 with the touch panel is arranged.

The UPD coil unit 8 is embedded in an upper surface part where a patient is lying in the inspection bed 2. The UPD coil unit 8 is connected via a UPD cable 34 to the AWS unit 4.

The AWS unit 4 and the endoscopic system control device 5 in this embodiment perform, as shown in FIG. 8, for example, data transmission and reception with wireless transmission and reception units 77 and 101. Also, as shown in FIG. 4, the observation monitor 6 is connected to a monitor connector of the endoscopic system control device 5 with a monitor cable 35.

It should be noted that, as shown in FIG. 4, transmission and reception units 101 and 36 may be attached to the endoscopic system control device 5 and the observation monitor 6, respectively, so that video signals are transmitted from the endoscopic system control device 5 to the observation monitor 6 to display an endoscope image corresponding to the respective video signals on the display screen.

As will be described later, image data captured by a CCD 25 from the AWS unit 4 side and image data of the insert section shape of the endoscope 3 detected by using the UPD coil unit 8 (the UPD image) are transmitted to the endoscopic system control device 5. Thus, the endoscopic system control device 5 transmits video signals of the image data to the observation monitor 6, whereby the UPD image can be also displayed on the display screen together with the endoscope image.

The observation monitor 6 is composed of a high definition TV (HDTV) monitor so that plural types of images in this way can be displayed on the display screen.

Also, in this embodiment, accommodating concave portions are formed at one end section in the longitudinal direction of the inspection bed 2 and a position below the end section, whereby the tray conveyance trolley 38 can be slidably accommodated. An endoscope tray 39 for accommodating the endoscope 3 is placed on an upper part of the tray conveyance trolley 38 as shown in FIG. 9.

Then, the endoscope tray 39 accommodating the endoscope 3 after sterilization or disinfection can be conveyed by the tray conveyance trolley 38 and can be accommodated in the accommodating concave portion of the inspection bed 2 the surgeon can use the endoscope 3 by removing it from the endoscope tray 39 and also accommodate the endoscope 3 again in the endoscope tray 39 after the end of the endoscopic inspection. After that, with use of the tray conveyance trolley 38, by conveying the endoscope tray 39 accommodating the endoscope 3 after use, sterilization or disinfection can be performed smoothly as well.

As shown in FIG. 4, for example, the AWS unit 4 includes an endoscope connector 40. Then, an endoscope connector 41 (of the endoscope 3) is detachably connected to the endoscope connector 40, as shown in FIG. 8.

In this case, FIGS. 5 and 6 show a specific outer appearance shape of the endoscope connector 40 on the AWS unit 4 side.

Then, FIGS. 7A to 7E show a structure of an AWS adapter 42 detachably attached to the endoscope connector 40 of the AWS unit 4, and FIG. 8 shows internal structures of the endoscope connector 40 on the AWS unit 4 side and the endoscope connector 41 on the endoscope 3 side by way of connection status.

Figure 6A:
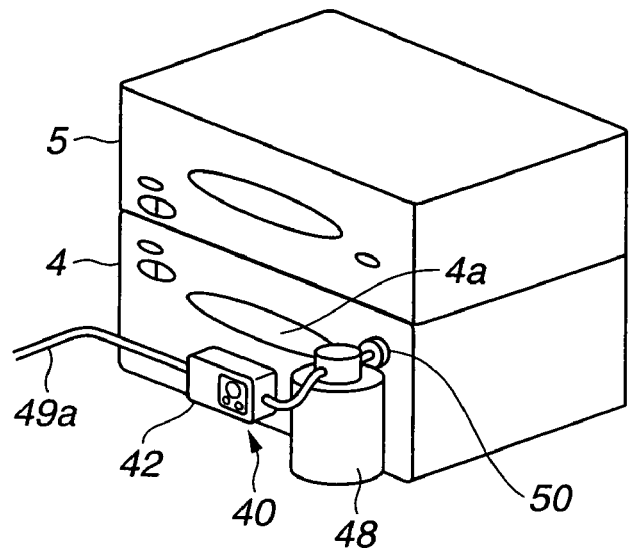
FIG. 6A is a perspective view showing a state in which a detachable AWS adapter is attached to the AWS unit in the endoscopic system according to the first embodiment.
Figure 6B:
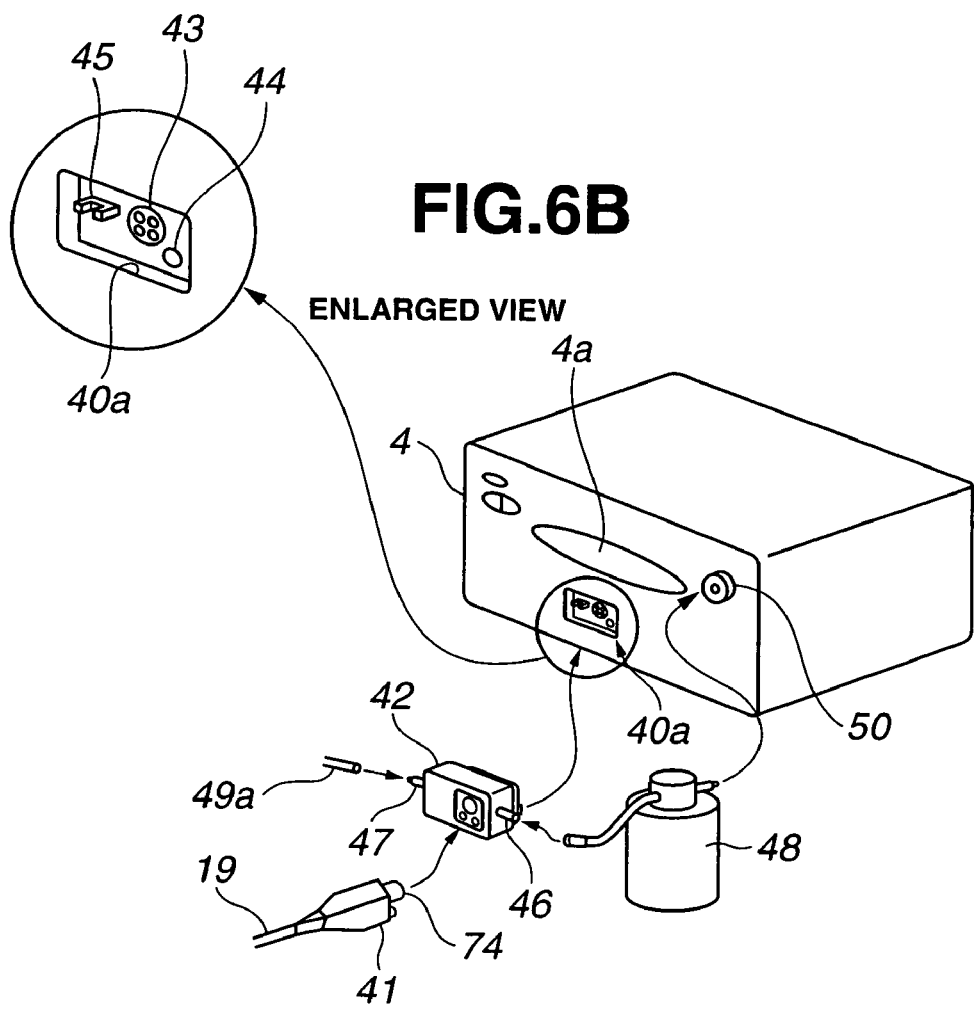
FIG. 6B is a perspective view showing a state in which the detachable AWS adapter is removed from the AWS unit in the endoscopic system according to the first embodiment.

In actuality, as shown in FIG. 6B, a concave AWS adapter attachment section 40a is provided on the front face of the AWS unit 4. An AWS adapter (duct line connection adapter) 42 shown in FIGS. 7A to 7E is attached to the AWS adapter attachment section 40a, thereby forming the endoscope connector 40, and the endoscope connector 41 on the endoscope 3 side is connected to the endoscope connector 40.

The AWS adapter attachment section 40a includes an endoscope electric connector 43, an airing connector 44, and a pinch valve 45. An inner end surface of the AWS adapter 42 is detachably attached to the AWS adapter attachment section 40a, and from an outer end surface side, the endoscope connector 41 of the endoscope 3 is connected.

A detail of the AWS adapter 42 is shown in FIGS. 7A to 7E. FIG. 7A is a front view of the AWS adapter 42, FIG. 7B and FIG. 7C are left and right side views, and FIG. 7D and FIG. 7E are cross-sectional views taken along the lines A-A' and B-B' in FIG. 7A.

The endoscope connector 41 is inserted to a concave portion 42a on the front face of the AWS adapter 42. In that case, an electric connector section of the endoscope connector 41 is inserted to a through hole 42b provided in the concave portion and connected to the facing endoscope connector 43 in the through hole 42b provided in the AWS unit 4.

An air water connecter 42c and a suction connecter 42d are provided on a lower side of the through hole 42b, to which an air water connecter 63 and a suction connecter 64 in the endoscope connector 41 (refer to FIGS. 8 and 9) are connected, respectively.

It should be noted that a concave portion 42f is provided on a base end surface side of the AWS adapter 42 for accommodating the pinch valve 45 protruding from the AWS adapter attachment section 40a.

As shown in FIG. 7E, the air water connecter 42c provided to the AWS adapter 42 has an internal duct line in communication therewith is branched, thereby forming an air connecter 42e connected to the airing connector 44 of the AWS unit 4 and a water connecter 46 protruding to the side direction. Also, in the suction connecter 42d, a duct line in communication therewith is bent to protrude from the side to form a suction connecter 47 and a relief duct line 47a is also formed by being branched towards the upper side in the middle way, for example. After the relief duct line 47a is pinched by the pinch valve 45 in the middle way, the upper end is opened.

When a suction pump not shown forming the suction section is set in a regular operation status, the relief duct line 47a is normally set in a released status by the pinch valve 45, and when a suction operation is performed, the pinch valve 45 is driven. Then, as the relief duct line 47a is closed by the pinch valve 45, the release is cancelled, and the suction operation can be performed.

The water connecter 46 and the suction connecter 47 are connected, as shown in FIG. 5 or the like, to a watering tank 48 and a suction device (inserted by a suction tank 49b via a suction tube 49a), respectively. The watering tank 48 is connected to a watering tank connecter of the AWS unit 4. It should be noted that an operation panel 4a is provided on the upper side of the endoscope connector 40 in the front face of the AWS unit 4.

Next, a specific structure of the endoscope of the first embodiment of the present invention will be described with reference to FIG. 9.

Figure 9:
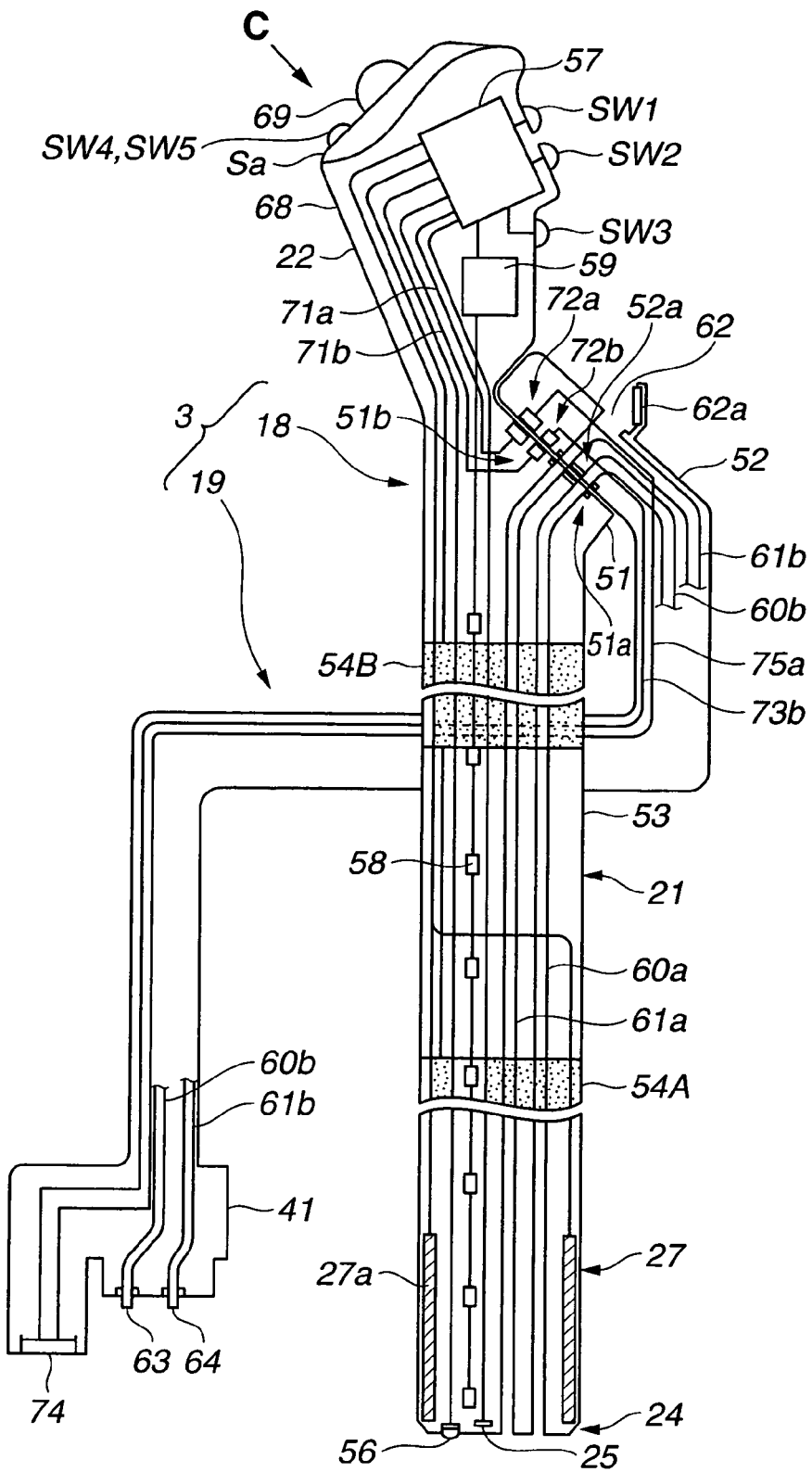
FIG. 9 is a side view with a see-through of a part of an internal structure component of an endoscope in the endoscopic system according to the first embodiment.

FIG. 9 is a side view with a see-through of a part of an internal structure component of the endoscope in the endoscopic system according to the first embodiment. It should be noted that FIG. 9 is a view of the endoscope 3 as seen from one side, showing main components provided inside the endoscope through cutting off a part of the surface.

In FIG. 3, as the detail has been described, the flexible endoscope 3 includes the endoscope main body 18 having the flexible insert section 21 and the operation section 22 provided at the rear end, and the tube unit 19 (a disposal type is adapted in this embodiment) which has a (tube unit connection) connecter section 51 in the vicinity of a base end (front end) of the operation section 22 in the endoscope main body 18, to which the overall connecter section 52 at the base end is detachably connected.

The endoscope connector 41 detachably connected to the AWS unit 4 described above is provided to a tail end of the tube unit 19.

The insert section 21 includes the rigid distal end section 24 provided at the distal end of the insert section 21, the freely bendable bending section 27 provided at the rear end of the distal end section 24, and an elongated flexible portion (corrugated tube section) 53 extending from the rear end of the bending section 27 to the operation section 22. The consistency varying actuators 54A and 54B formed of an electro-conductive polymer artificial muscle (abbreviated as EPAM) or the like which expands upon voltage application while the consistency can be changed) are provided at plural positions, to be specific, two locations, in the middle way to the flexible portion 53.

For example, a light emitting diode (abbreviated as LED) 56 is arranged as the illumination section on an inner side of an illumination window provided to the distal end section 24 of the insert section 21. The illumination light of the LED 56 is output forward via an illumination lens integrally attached to the LED 56 for illuminating a subject such as an affected area. It should be noted that the LED 56 may be an LED for generating a white light or may be composed by using a R-LED, a G-LED, and a B-LED for emitting lights in wavelengths of red (R), green (G), and blue (B), respectively. The illumination section can be formed by using an LD (laser diode) or the like.

An objective lens not shown is attached to the observation window adjacently provided to this illumination window, and the CCD 25 including the gain varying function is arranged at the image forming location, thereby forming the image pickup section for capturing the subject. The CCD 25 according to this embodiment has a gain varying function build in the CCD element itself. With the gain varying function, the gain of the CCD output signal can be easily varied to about several 100 fold. Thus, even under the illumination of the LED 56, a bright image with low reduction in S/N can be obtained. Also, the LED 56 has the sufficient light emitting efficiency as compared with the lamp, thereby suppressing the temperature rise in the vicinity of the LED 56.

One end of the signal line that is inserted in the insert section 21 and whose the other ends are connected to the LED 56 and the CCD 25, respectively, is provided in the operation section 22 and connected to the control circuit 57 for performing a central control process (collective control process).

The UPD coils 58 are arranged at plural positions along the longitudinal direction in the insert section 21 with a predetermined interval, and the signal line connected to each of the UPD coils 58 is connected to the control circuit 57 via a UPD coil driver unit 59 provided in the operation section 22.

Also, the articulation actuators 27a formed by arranging EPAM in the longitudinal direction are arranged at four locations in the circumferential direction on the inner side of an outer skin in the bending section 27. The articulation actuator 27a and the consistency varying actuators 54A and 54B are also connected the control circuit 57 via the signal line.

Figure 10A:
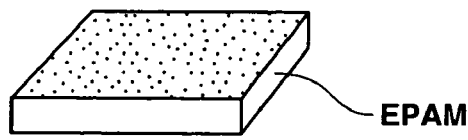
FIG. 10A is an outer appearance perspective view showing a schematic structure of an electroconductive polymer artificial muscle used in the endoscope in the endoscopic system according to the first embodiment.
Figure 10B:
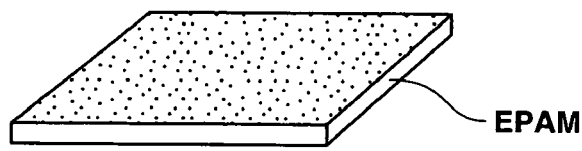
FIG. 10B is an outer appearance perspective view showing a schematic structure of the electroconductive polymer artificial muscle used in the endoscope in the endoscopic system according to the first embodiment.
Figure 10C:
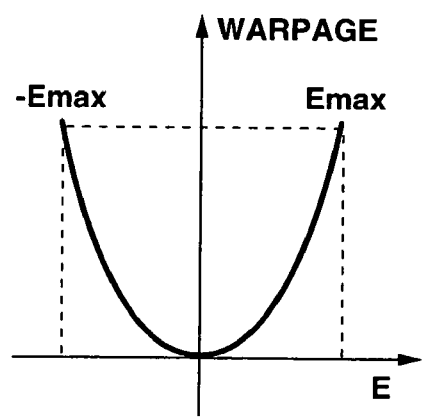
FIG. 10C is a graph showing a warpage of the electroconductive polymer artificial muscle used in the endoscope in the endoscopic system according to the first embodiment.

The EPAM used for the articulation actuator 27a and the consistency varying actuators 54A and 54B has, as shown in FIG. 10A, for example, electrodes attached on board-shaped both sides. With the application of a voltage, contraction in a thickness direction is caused, whereby expansion in the longitudinal direction can be achieved. It should be noted that, as shown in FIG. 10C, this EPAM can vary a warpage thereof in proportion to approximately a square of electric field intensity E generated by the applied voltage, for example.

When used as the articulation actuator 27a, the EPAM is formed into a wire to expand on one side and contract on the other side, thereby bending the bending section 27 similarly to the normal wire function. Also, with the expansion or contraction, the consistency can be varied. By using the functions, the consistency varying actuators 54A and 54B can vary, the consistency of that part.

On the other hand, the air water duct line 60a and the suction duct line 61a are inserted through the insert portion 21. Rear end sections of the air water duct line 60a and the suction duct line 61a are extended to a duct line connector 51a formed at the opening end of the connector section 51, which have openings at the connecter section 51a.

Meanwhile, the air water duct line 60b and the suction duct line 61b are inserted through the tube unit 19. Rear end sections of the air water duct line 60b and the suction duct line 61b are extended to a tube connector section 52a formed at the opening end of the overall connecter section 52, which have openings at the tube connecter section 52a.

It should be noted that the suction duct line 61b is branched inside the tube connecter section 52a to be opened to the outside.

The duct line connector section 51a in the connector section 51 and the tube connecter section 52a in the overall connecter section 52 are mechanically connected to each other when the connector section 51 is mounted to the overall connecter section 52. At this time, the opening ends of the air water duct line 60a and the suction duct line 61a are connected to the opening ends of the air water duct line 60b and the suction duct line 61b. It should be noted that the suction duct line 61a is connected to the suction duct line 61b inserted through the tube unit 19, and further is in communication with an insertion port (also referred to as biopsy port) 62 for allowing insertion of an endo-therapy product such as forceps, which is branched inside the tube connecter section 52a to be opened to the outside. The biopsy port 62 is closed by a forceps valve 62a when not used.

The rear ends of the air water duct line 60b and the suction duct line 61b on a side close to the hand function as the air water connecter 63 and the suction connecter 64 in the endoscope connector 41.

The air water connecter 63 and the suction connecter 64 are connected to the air water connecter 42c and the suction connecter 42d of the AWS adapter 42 shown in FIGS. 6A AND 6B and FIGS. 7A to 7E and the like, respectively. Then, as shown in FIGS. 7A to 7E, the air water connecter 42c is branched into the air duct and the water duct line inside the AWS adapter 42, the air duct is connected to an airing watering pump 65 in the AWS unit 4 via an electromagnetic valve B1, whereas the water duct line is connected to the watering tank 48. Also, the watering tank 48 is connected to the airing watering pump 65 via an electromagnetic valve B2 in the middle way. The airing watering pump 65, and the electromagnetic valves B1 and B2 are connected to the AWS control unit 66 through a control line (driver line). With the AWS control unit 66, closing and opening are controlled, whereby airing and watering can be conducted. It should be noted that the AWS control unit 66 performs an operation control for suction by the control of opening and closing of the pinch valve 45.

Then, as shown in FIG. 9, the operation section 22 of the endoscope main body 18 includes a grasping section 68 grasped by the surgeon. The periphery section including the grasping section 68 has, for example, three endoscope switches SW1, SW2, and SW3 for performing remote control operations such as release and freeze (abbreviated as remote control operations) arranged in the axis of the longitudinal direction of the operation section 22, which are connected to the control circuit 57.

The track ball 69 of a water proof structure for performing the articulation operation (bending operation) and setting of other remote control operation by switching from the articulation operation is provided at a position where the operations can be performed by the hand grasping the grasping section 68 on an inclined surface section Sa formed so as be inclined as an upper surface of the opposite side to the locations where the endoscope switches SW1, SW2, and SW3 in the operation section 22 are provided.

Figure 11:
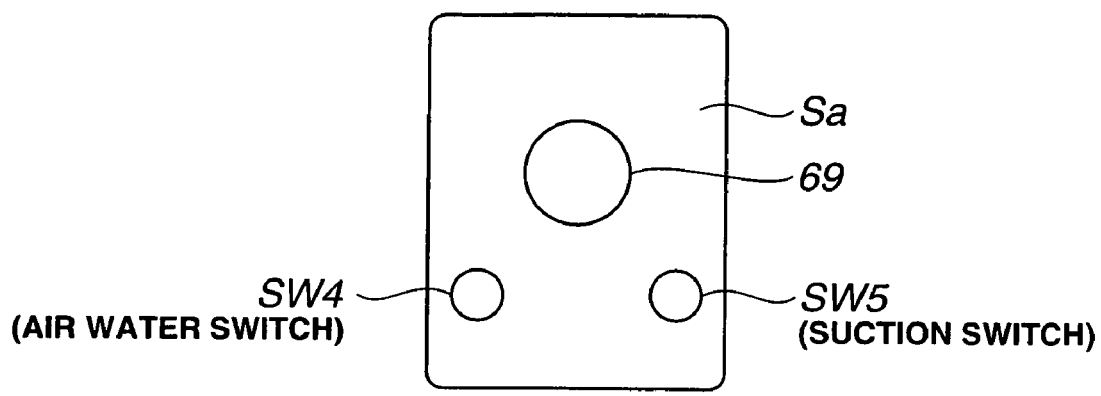
FIG. 11 is a front view showing a track ball provided to the operation section and a peripheral section of the endoscope in the endoscopic system according to the first embodiment.

FIG. 11 is a front view showing the track ball provided to the operation section and a peripheral section of the endoscope in the endoscopic system according to the first embodiment, and is a view as taken by the arrow C in FIG. 9.

As shown in FIG. 11, two endoscope switches SW4 and SW5 are bilaterally symmetrically arranged at locations on both sides of the track ball 69 on the inclined surface section Sa in the longitudinal direction of the operation section 22, to which functions of the air water switch and the suction switch are normally allocated.

When the case of seeing the operation section 22 of the endoscope 3 from the arrow C direction in FIG. 9, the track ball 69 is on the center line in the longitudinal direction to the operation section 22 or the longitudinal direction of the insert section 21. At the same time, the two endoscope switches SW4 and SW5 are bilaterally symmetrically arranged, and the endoscope switches SW1, SW2, and SW3 are arranged along the center line on the back side.

In this manner, the various operation parts such as the track ball 69 are bilaterally symmetrically arranged to the center axis in the longitudinal direction in the operation section 22. When the surgeon grasps the grasping section 68 of the operation section 22 for operations, even when a left hand or a right hand grasps the grasping section, the same satisfactory operability can be ensured.

The track ball 69 and the endoscope switches SW4 and SW5 are also connected to the control circuit 57. The track ball 69 and the endoscope switches SW1 to SW5 correspond to articulation/remote control operator 28 shown in FIG. 3.

Next, the connection relation between the connector section 51 and the overall connecter section 52, which enable the connection in a characteristic way in the endoscope 3 will be described with reference to FIG. 9 and FIG. 12.

Figure 12:
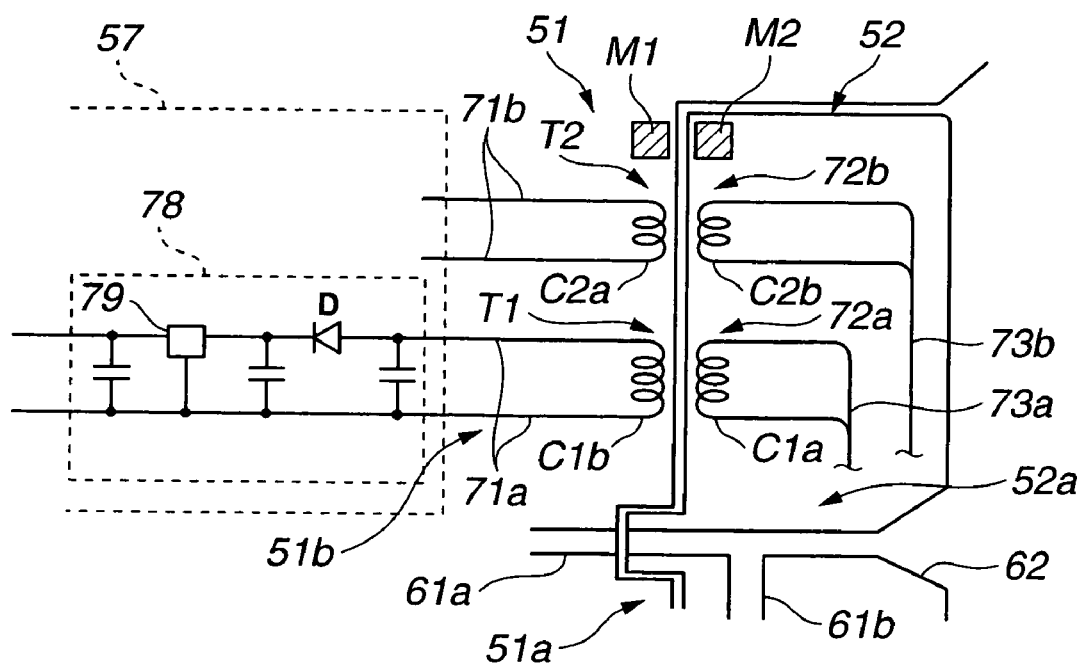
FIG. 12 is a circuit diagram showing an electric structure of a connection section between the operation section and a tube unit of the endoscope in the endoscopic system according to the first embodiment.

FIG. 12 is a circuit diagram showing an electric structure of the connection section between the operation section and the tube unit of the endoscope in the endoscopic system according to the first embodiment.

One ends of a power supply line 71a and a signal line 71b are connected to the control circuit 57. Then, the other ends of the power supply line 71a and the signal line 71b are respectively connected to electromagnetic connection sections 72a and 72b in the connector section 51. Meanwhile, a power supply line 73a and a signal line 73b are inserted through the tube unit 19. One ends of the power supply line 73a and a signal line 73b are connected to an electric connector 74 having a power supply and a signal contact in the endoscope connector 41. Then, the other ends of the power supply line 73a and the signal line 73b are respectively connected to the electromagnetic connection sections 72a and 72b in the overall connecter section 52. It should be noted that the electromagnetic connection sections 72a and 72b on the connector section 51 side are referred to as a transmission unit 51b.

When the overall connecter section 52 is mounted to the connector section 51, the electromagnetic connection sections 72a and 72b supply the power supply line 71a with the electric power from the power supply line 73a without so-called metal electrode junction, and enable the transmission of the signal between the signal line 71b and the signal line 73b.

That is, a primary side coil C1a is arranged at the other end of the power supply line 73a in the tube unit 19 and a secondary side coil C1b is arranged at the opposing other side of the power supply line 71a. While these coils are arranged adjacent to each other, a transformer T1 having an electromagnetic coupling in a low magnetic flux leakage is formed.

Similarly, a coil C2a is arranged at the other end of the signal line 71b, and a coil C2b is arranged at the opposing other end of the signal line 73b. Then, while these coils are arranged adjacent to each other, a transformer T2 having an electromagnetic coupling in a low magnetic flux leakage is formed. It should be noted that the detail will be described later.

While the user connects the endoscope connector 41 to the AWS unit 4, as shown in FIG. 8, the power supply line 73a is connected to the power supply unit 75 via the endoscope electrical connector 43 of the AWS unit 4, and the signal line 73b is connected (via the power supply unit 75) to the UPD unit 76, the transmission and reception unit 77, and the AWS control unit 66. It should be noted that the transmission and reception unit 77 is connected to the antenna section for performing wireless transmission and reception of radio waves.

The alternating electric power supplied by the power supply line 73a inserted through the tube unit 19 from the power supply unit 75 is supplied to the primary side coil C1a in the connector section 52. The secondary side coil C1b is arranged inside an outer case of the connector section 51, and the primary side coil C1a and the secondary side coil C1b are adjacent to each other to form the transformer T1 having an electromagnetic coupling in a low magnetic flux leakage.

Then, with the electromagnetic coupling, the alternating electric power supplied to the coil C1a is efficiently transmitted to the secondary side coil C1b. The coil C1b is connected to a power supply circuit 78 in the control circuit 57, and with the power supply circuit 78, a direct current electric power necessary for the control circuit 57 side is generated.

The power supply circuit 78 converts a direct current voltage rectified via a rectifying diode D and a smoothing capacitor into a direct current voltage necessary for the operation of the control circuit 57 by, for example, a three terminal power supply IC 79 and the smoothing capacitor to be supplied to the control circuit 57.

The signal line 71b (forming the common signal transmission section) connected to the control circuit 57 is connected to the coil C2a as described above, and the coil C2b adjacently opposing the coil C2a is connected to the signal line 73b inserted through the tube unit 19. In other words, almost similarly to the case of the transformer T1, the transformer T2 with the electromagnetic coupling between the coil C2a and the coil C2b is formed.

Via the coils C2a and C2b causing the electromagnetic coupling, a signal is transmitted from the signal line 71b to the signal line 73b and a signal is transmitted in the opposite direction.

Figure 13:
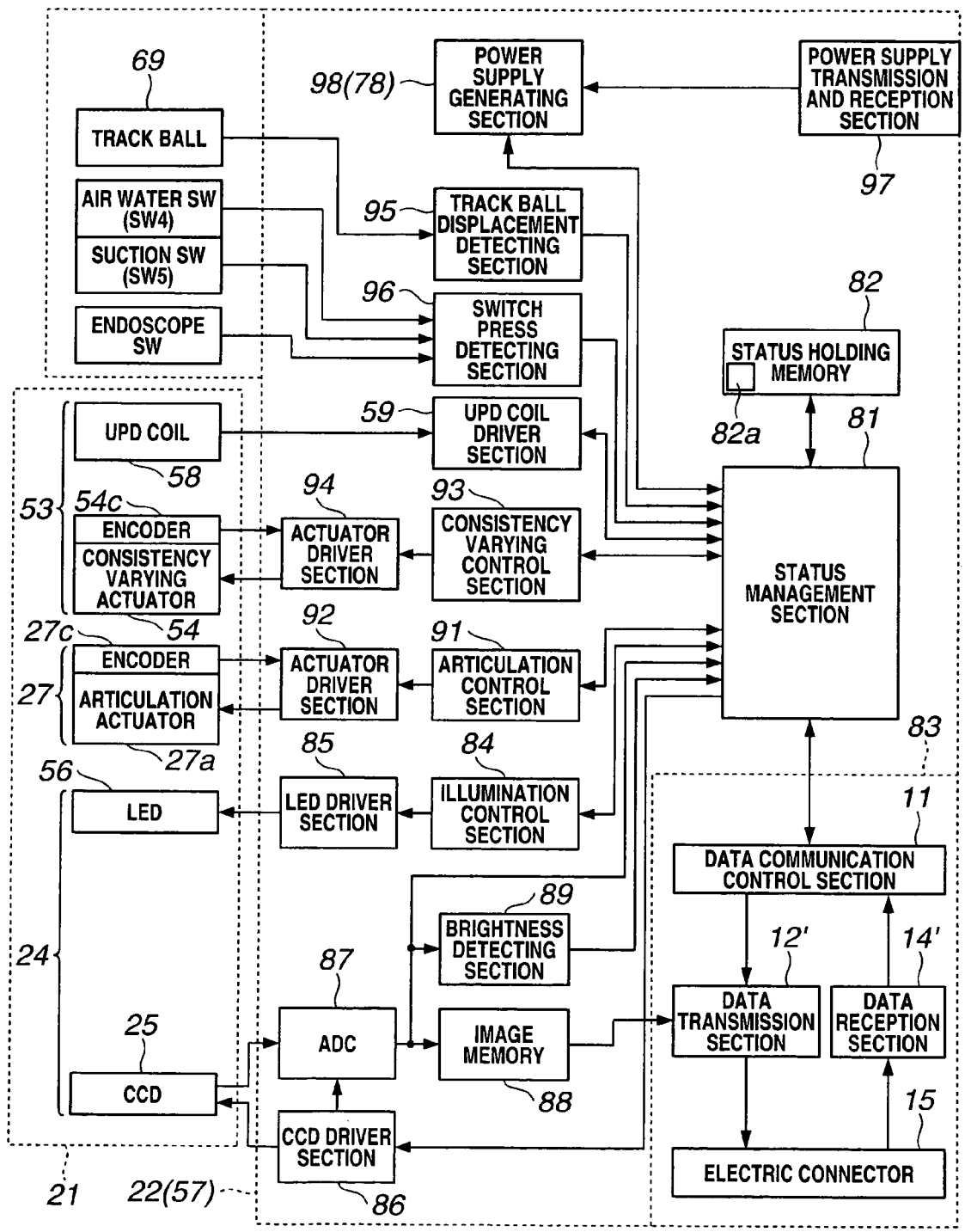
FIG. 13 is a block diagram showing an electric structure of the endoscope in the endoscopic system according to the first embodiment.

In this embodiment, as the internal structure is described in FIG. 13, as the various operation sections and image pickup sections are controlled in a central manner or managed by the control circuit 57, the number of the electric signal lines inserted through the tube unit 19 can be reduced. Also when the functions of the endoscope 3 are changed, the signal line 73b in the tube unit 19 can be used without change. In other words, the signal line 73b forms a common signal transmission section for commonly transmitting various signals.

It should be noted that as shown in FIG. 12, for example, magnets M1 and M2 are arranged adjacent to the transformer T2 with different magnet poles are opposed to each other. When the overall connecter section 52 is connected to the connector section 51, the coils C1a and C1b, and the coils C2a and C2b can be detachably attached while arranged adjacent to each other in the opposing manner. It should be noted that instead of the magnets M1 and M2, concave and convex portions for positioning both the connector sections 51 and 52 to be fitted to each other may be provided.

The endoscope 3 of this embodiment thus allows the tube unit 19 to be detachably attached to the endoscope main body 18, and when the tube unit 19 is mounted to the endoscope main body 18, it is characterized in that the connection section without relying on the mutual metal electrode connection performs transmission and reception of the power supply and signals between the endoscope main body 18 and the tube unit 19.

FIG. 13 is a block diagram showing an electric structure of the endoscope in the endoscopic system according to the first embodiment.

The CCD 25 and the LED 56 are arranged at the distal end section 24 of the insert section 21 shown in the lower section on the left hand side of FIG. 13. The articulation actuator (in this embodiment, specifically, EPAM) 27a and an encoder 27c are arranged at the bending section 27 shown in the upper section in the drawing.

The flexible section 53 has a consistency varying actuator 54 and an encoder 54c (in this embodiment, specifically, which are consistency varying actuators 54A and 54B formed of the EPAM, but one actuator is representing for the sake of simplicity. In addition, the UPD coil 58 is arranged at the flexible section 53.

The track ball 69, the air water SW (SW4), the suction SW (SW5), and the endoscope SW (SW1 to SW3) are arranged on the surface of the operation section 22 in the upper section of the flexible portion 53 in the insert section 21. It should be noted that as will be described later, the track ball 69 is used for selecting and setting of the articulation operation and other functions, etc.

As shown in the left hand side of FIG. 13, these are connected via the signal line to the control circuit 57 provided in the operation section 22 shown on the right hand side (It should be noted that, the UPD coil driver unit 59 is in the operation sections 22), the control circuit 57 performs the drive control for the functions, a signal processing, etc.

The control circuit 57 includes the status management section 81 composed of the CPU for managing the control status and the like. The status management section 81 is connected to the status holding memory 82 for holding (storing) the status of the respective sections. The status holding memory 82 includes a program storing memory 82a as the control information storing section. By rewriting program data as control information stored in the program storing memory 82a, even when the components shown in FIG. 13 are changed, the CPU structuring the status management section 81 can perform control (management) corresponding to the changed structure.

The status holding memory 82 or at least the program storing memory 82a is composed of, for example, a nonvolatile and electrically rewritable flash memory, EEPROM, or the like, whereby program data change can be easily conducted through the status management section 81.

For example, via the signal line 71b, that is, in the following wired way, a command for changing the program data is sent via a transmission and reception unit 83 to the status management section 81, and program data for rewriting is transmitted from the AWS unit 4 side after the command, thereby enabling the program data change. Also, version up etc., can be easily executed via the signal line 71b.

In addition, device model information or use status unique to the respective endoscopes 3 may be written and held in the status holding memory 82 in the following manner, and the information may be effectively used. To be specific, the status holding memory 82 holds, for example, device model information on the endoscope 3 (for example, information on a type of the CCD 25, the length of the insert section of the insertion tube, or the like), and individual information different in each of the endoscopes 3 due to the use status for the endoscopy or the like (for example, information on use time (summed up use time or accumulated use time for the endoscopy), the number of times for performing washing, an adjusted value, a maintenance history, or the like). These pieces of information are used for the system operation decision, information provision to the user, etc.

These pieces of information can be edited from the outside, such as the endoscopic system control device 5, a washing device not shown, or the like.

As a result, it is possible to effectively use the information (data) which the endoscope ID has, while the status holding memory 82 doubles as the function of the existing endoscope ID to be commonly used.

Moreover, with the provision of the status holding memory 82, it is unnecessary to additionally provide a new endoscope ID, so more advanced function than the existing endoscope ID can be achieved, thereby making it possible to perform appropriate setting, adjustment, management, processing, and the like in more detail.

The status management section 81 is connected to the transmission and reception unit 83 of the wired method for performing wired communication with the AWS unit 4 (in this embodiment) (as the transmission and reception unit 83 corresponds to FIG. 2B, the components have the reference numerals of FIG. 2B. It should be noted that the electric connector 15 corresponds to the electromagnetic connection sections 72a and 72b in the operation section 22 and to the electric connector 74 at the end section of the tube unit 19).

Then, the status management section 81 controls via an illumination control section 84 for controlling the illumination an LED driver section 85 that is controlled by the illumination control section 84. The LED driver section 85 applies the LED 56 with the LED driver signal to cause the LED 56 functioning as the illumination section to emit light.

With the light emittance of the LED 56, the illuminated subject such as the affected area is image-focused on an image pickup surface of the CCD 25 located at the image forming location by an objective lens not shown attached to the observation window, and photoelectric conversion is performed by the CCD 25.

In response to the CCD driver signal application from a CCD driver section 86 controlled by the status management section 81, the CCD 25 outputs the signal charge accumulated through the photoelectric conversion in the form of the image pickup signal. The image pickup signal is converted from an analog signal to a digital signal by an A/D converter (abbreviated as ADC) 87 and then input to the status management section 81. At the same time, the digital signal (image data) is stored in an image memory 88. The image data in the image memory 88 is sent to the data transmission section 12' of the transmission and reception unit 83.

Then, the image data is transmitted to the AWS unit 4 side from the electric connector 15 (the transmission unit 51b in this embodiment) via the signal line 73b in the tube unit 19. Furthermore, the image data is wirelessly transmitted from the AWS unit 4 to the endoscopic system control device 5. An output signal of the ADC 87 is sent to a brightness detecting section 89. Information on the image brightness detected by the brightness detecting section 89 is sent to the status management section 81. The status management section 81 performs light intensity adjustment on the basis of this information, so that the illumination quantity by the LED 56 is set to an appropriate brightness via the illumination control section 84.

Then, the status management section 81 controls an actuator driver section 92 via the articulation control section 91 to perform a control for driving the articulation actuator (EPAM) 27a with the actuator driver section 92. It should be noted that the drive amount of the articulation actuator (EPAM) 27a is detected by the encoder 27c so that the drive amount is controlled to match the instructed amount.

The status management section 81 controls the actuator driver section 94 through the consistency varying control section 93. With the actuator driver section 94, the consistency varying actuator 54 is controlled for the drive. It should be noted that the drive amount of the consistency varying actuator 54 is detected by the encoder 54c so that the drive amount is controlled to be a value corresponding to the instructed amount.

The operation signal corresponding to the operation amount from the track ball 69 or the like provided to the operation section 22 is input to the status management section 81 via a track ball displacement detecting section 95.

Furthermore, the switch press operation such as turning ON of the air water SW, the suction SW, and the endoscope SW is detected by a switch press detecting section 96, and the detected information is input to the status management section 81. The EPAM has a characteristic to generate an electromotive force due to deformation by an external force, and the EPAM may be used as an encoder that is arranged in the opposite side to the EPAM.

The control circuit 57 includes a power supply transmission and reception section 97 and a power supply generating section 98. The power supply transmission and reception section 97 specifically is the electromagnetic coupling connection section 72a in the operation section 22. Then, the alternating current power supply transmitted from the power supply generating section 98 is converted into a direct current power supply in the power supply generating section 98. The power supply generating section 98 corresponds to the power supply circuit 78 in FIG. 11. The direct current power supply generated by the power supply generating section 98 supplies the respective sections with necessary electric power in the control circuit 57 for the operation.

Figure 14:
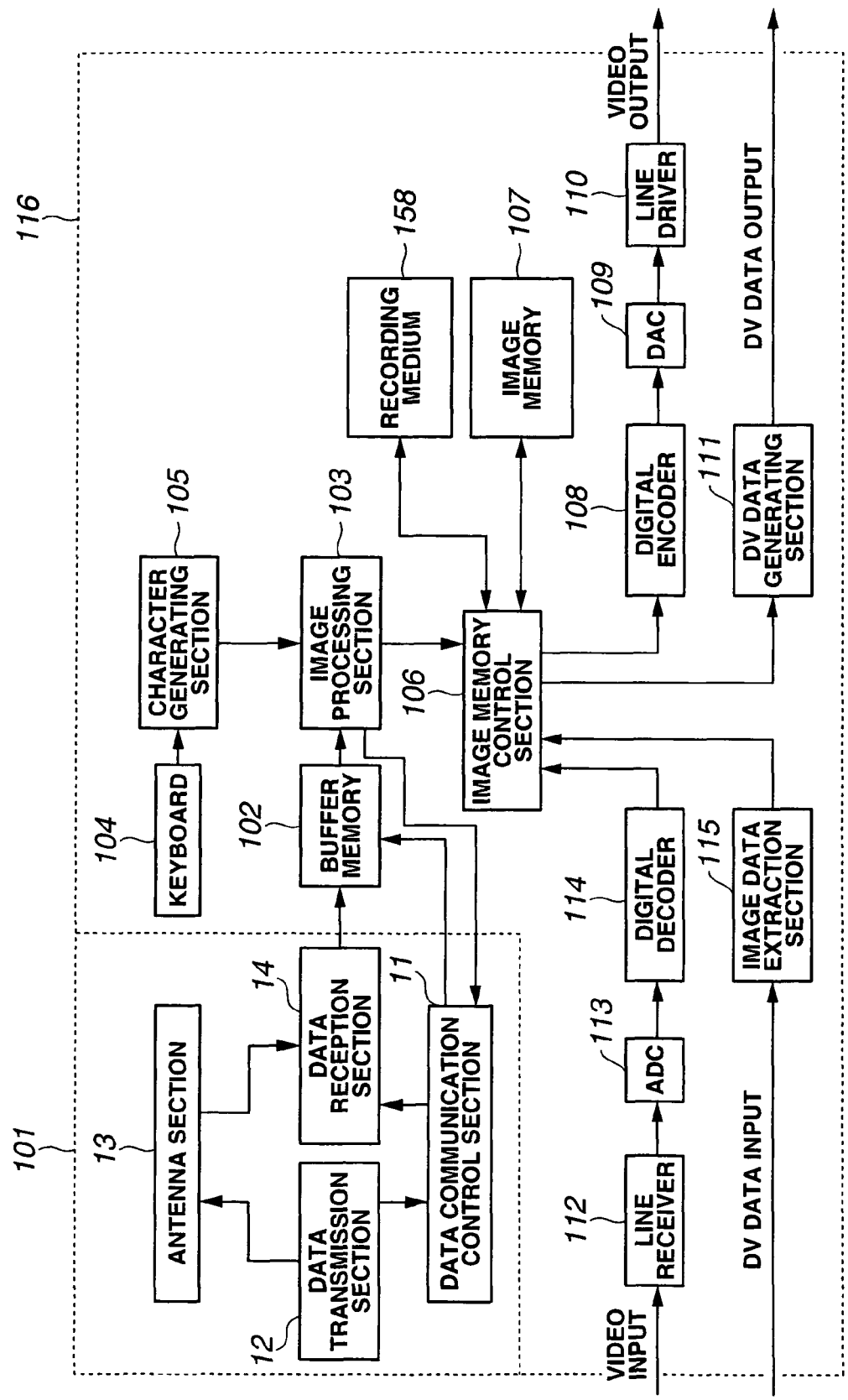
FIG. 14 is a block diagram showing a main electric structure of an endoscopic system control device in the endoscopic system according to the first embodiment.

FIG. 14 shows internal structures of a transmission and reception unit 101 and an image processing unit 116 of FIG. 8 in the endoscopic system control device 5.

The endoscopic system control device 5 includes, for example, the wireless transmission and reception unit 101. Data such as an image signal wirelessly transmitted from the AWS unit 4 is taken in the antenna section 13 to be sent to the data reception section 14. After being amplified, the data is subjected to a demodulation process. The operation of the data reception section 14 is controlled by the data communication control section 11, and the received data is sequentially accumulated in a buffer memory 102.

The image data in the buffer memory 102 is transmitted to an image processing section 103 for processing the image data. Character information from a character generating section 105 for generating character information in response to key input of a keyboard 104 is also input into the image processing section 103 other than the image data from the buffer memory 102, whereby it is possible to superimpose the character information or the like on the image data.

The image processing section 103 sends the input image data or the like to an image memory control section 106. Via the image memory control section 106, the image data or the like is temporarily stored in an image memory 107, and at the same time recorded in a recording medium 158.

The image memory control section 106 reads out the image data temporarily stored in the image memory 107 to be sent to a digital encoder 108. The digital encoder 108 encodes the image data into a predetermined video format and outputs the data to a D/A converter (abbreviated as DAC) 109. The DAC 109 converts a digital video signal into an analog video signal. The analog video signal is further output from a video output terminal to the observation monitor 6 via a line driver 110, and the observation monitor 6 displays an image corresponding to the video signal.

Then, the image data temporarily stored in the image memory 107 is read out to be input to a DV data generating section 111 as well. By the DV data generating section 111, DV data is generated to be output from a DV data output terminal.

The endoscopic system control device 5 includes a video input terminal and a DV data input terminal. A video signal input from the video input terminal passes through a line receiver 112 and an ADC 113. The video signal converted into the digital signal is demodulated by a digital decoder 114 to be input to the image memory control section 106.

From the DV data input to the DV data input terminal, image data is extracted (decoded) by an the image data extraction section 115 to be input to the image memory control section 106.

The image memory control section 106 temporarily stores the video signal (image data) input from the video input terminal or the DV data input terminal in the image memory 107, records in the recording medium 158, or outputs from the video output terminal to the observation monitor 6.

In this embodiment, from the AWS unit 4 side, image data captured by a CCD 25 of the endoscope 3 and the UPD image data generated from the UPD unit 76 are wirelessly input to the endoscopic system control device 5. The endoscopic system control device 5 converts these pieces of the image data into predetermined video signals to be output to the observation monitor 6. It should be noted that the endoscopic system control device 5 may receive UPD coil location data instead of the UPD image data to generate UDP image data in the image processing section 103.

FIG. 15 shows the internal structure of the AWS unit 4.

The image data and the operation data such as the switch input to the endoscope electric connector 43 from the control circuit 57 of the endoscope 3, is output to the data communication control section 11 of the transmission and reception unit 77 to be transmitted to the antennal section 13 of the endoscopic system control device 5 from the antennal section 13 together with the UPD image data from the UPD unit 76.

On the other hand, AWS related information on the operations for the air water switch, the suction switch, and the like, which are provided to the operation section 22 of the endoscope 3 is also sent to an air water control section 122. The air water control section 122 controls the operations of the pump 65 and an electromagnetic valve unit 124 in accordance with the operated information. The air water tubes 60b and 61b are connected to the electromagnetic valve unit 124 via the AWS adapter 42. The watering tank 48 is connected to the electromagnetic valve unit 124 and the AWS adapter 42, and a suction tank 49b is connected to the AWS adapter 42.

The AWS unit 4 is supplied with supply mains, and this alternating current power is sent to a power supply transmission output section 127 via an insulation transformer 126. The power supply transmission output section 127 supplies the alternating current power insulating from the supply mains from the electric connector 43 to the power line 73a of the endoscope 3 connected to the electric connector 43.

Output control for electric power transmission of the power supply transmission output section 127 is controlled by an electric power transmission control section 128 connected to the data communication control section 11.

Figure 16A:
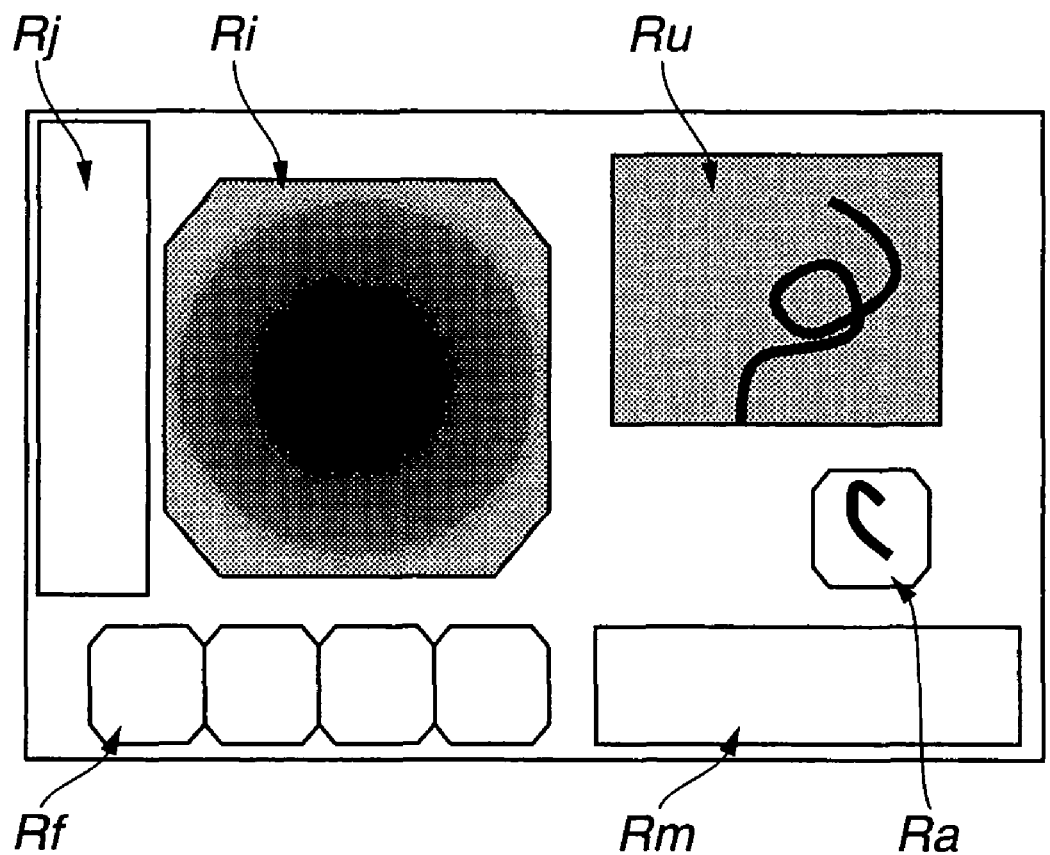
FIG. 16A shows a representative display example of a monitor display screen of an observation monitor in the endoscopic system according to the first embodiment.

In the endoscopic system 1 according to this embodiment, when the power supply is activated, various images shown in, for example, FIG. 16A are displayed on the observation monitor 6. In this case, in addition to an information display area Rj for displaying patient information or the like, a display area Ri of the endoscope image, a display area Ru of the UPD image, a display area Rf of a freeze image, and a display area Ra of an articulation shape, a menu display Rm is provided. A menu is displayed on the menu display Rm. It should be noted that regarding the display area Ra for the articulation shape, the articulation operation amount of the articulation actuator 27a is detected by the encoder 27c, and the articulation shape in that case is displayed.

Figure 16B:
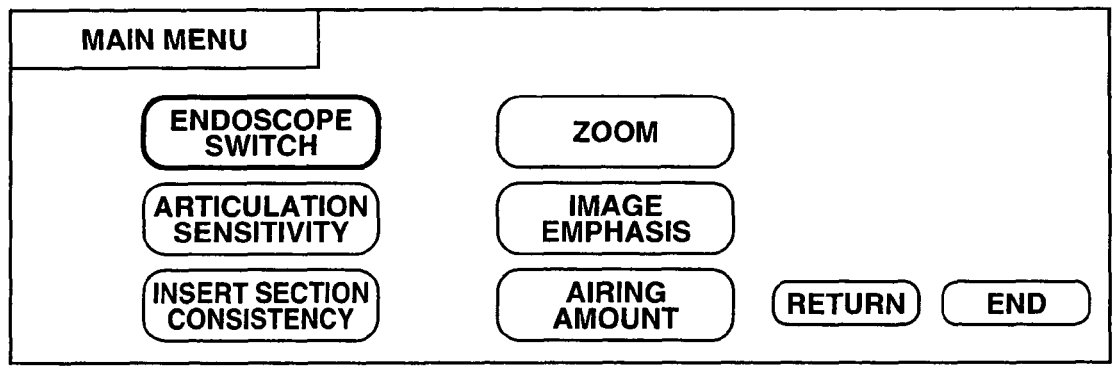
FIG. 16B shows a specific display example of a menu display of the monitor display screen of the observation monitor in the endoscopic system according to the first embodiment.

As a menu displayed on the menu display Rm, a main menu shown in FIG. 16B is displayed. This main menu displays a return item for return operation instruction for returning to the previous menu screen and an end item for end, in addition to items of an endoscope switch, an articulation sensitivity, an insert section consistency, a zoom, an image emphasis, and an airing amount.

Figure 16C:
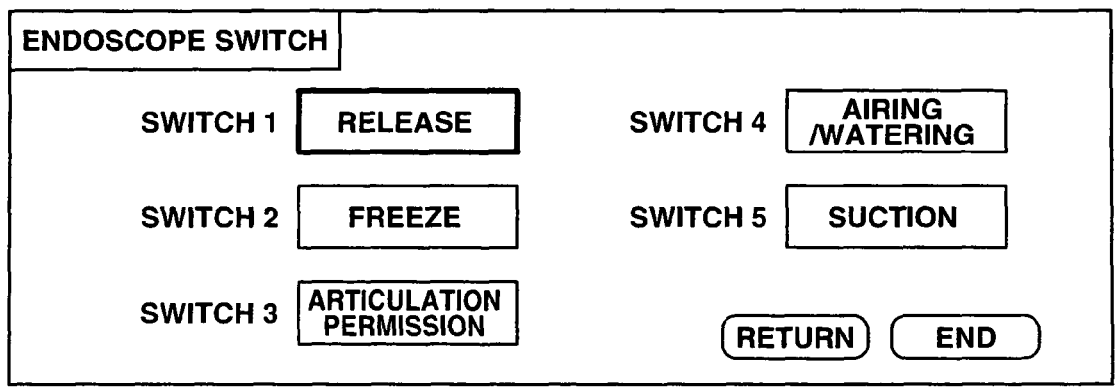
FIG. 16C shows another specific display example of a menu display of the monitor display screen of the observation monitor in the endoscopic system according to the first embodiment.

Then, when the user selects the endoscope switch item with a selection frame through the operation of the track ball 69 or the like, the frame of the endoscope switch item is displayed in bold and the display indicates the selected state. Furthermore, when the track ball 69 is pressed to perform a determined operation, whereby the functions to be allocated to the five switches SW1 to SW5 can be selected and set as shown in FIG. 16C.

Next, operation of the endoscopic system 1 of such a structure will be described.

As a prearrangement for the endoscopic inspection, first of all, the overall connecter section 52 on the disposal tube unit 19 side is connected to the connecter section 51 in the operation section 22 of the endoscope main body 18. In this case, transformers T1 and T2 forming the electromagnetic coupling connection sections 72a and 72b are electromagnetically connected to each other in an insulated and water tight way. With this connection, the preparation of the endoscope 3 is completed.

Next, the endoscope connector 41 of the tube unit 19 is connected to a connector 43 of the AWS unit 4. With one touch connection of this part, various duct lines, the power supply line, the signal line, and optical connection are completed at once. Unlike the prior art endoscopic system, it is unnecessary to perform connection of various duct lines, connection of the electrical connector, and the like on each occasion.

In addition, the user connects the UPD coil unit 8 to the AWS unit 4, and connects the endoscopic system control device 5 to the observation monitor 6. If necessary, the endoscopic system control device 5 is connected to the image recording unit 7 or the like, thereby completing the setup of the endoscopic system 1.

Next, the power supplies of the AWS unit 4 and the endoscopic system control device 5 are turned ON. As a result, the respective sections are activated in the AWS unit 4, the power supply unit 75 can be in a status for supplying the endoscope 3 side with an electric power via the power supply line 73a or the like.

The operations at the time of activation on the AWS unit 4 and the endoscope 3 in this case will be described with reference to FIGS. 17 and 18.

Figure 17:
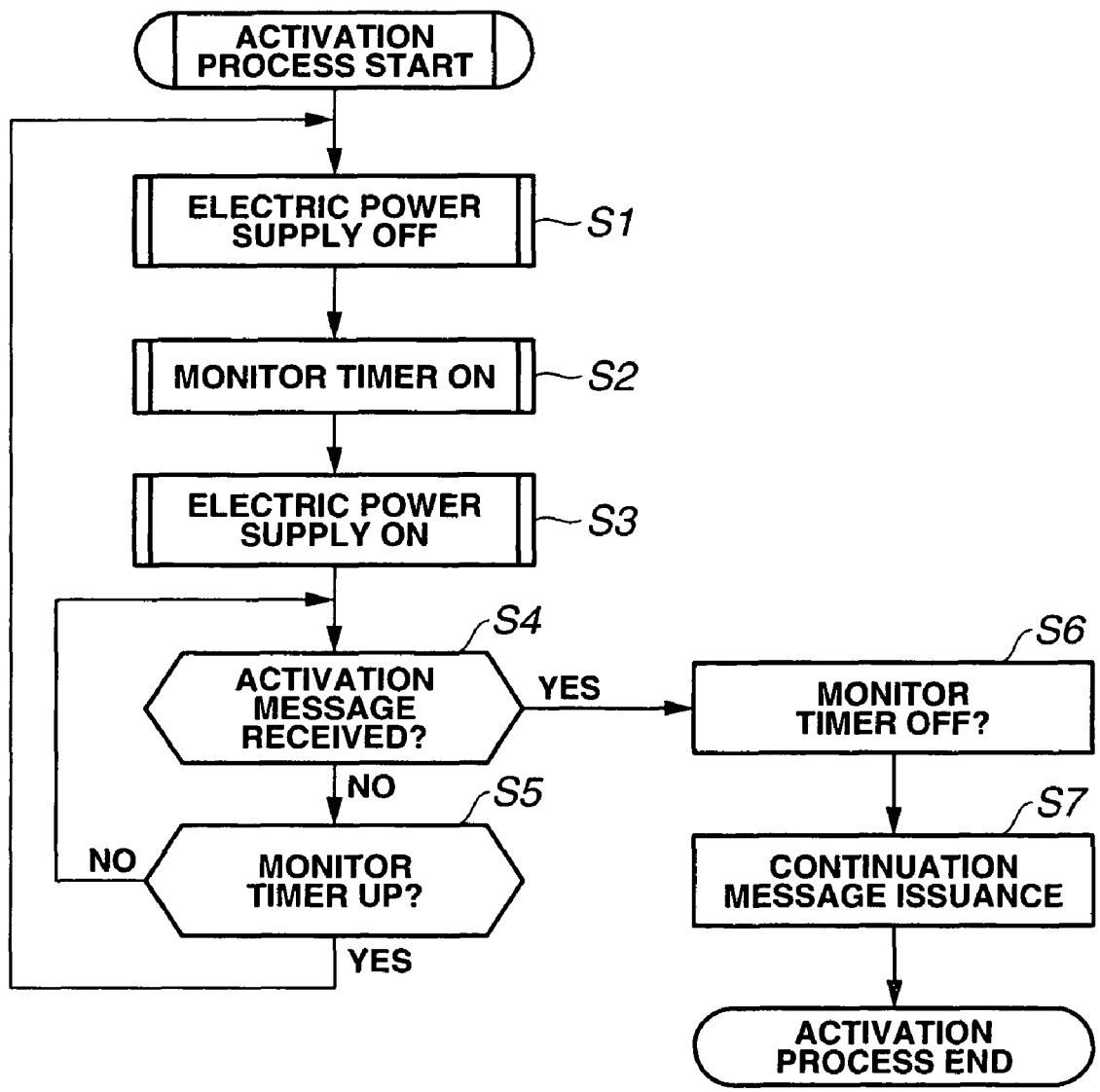
FIG. 17 is a flowchart showing an operation content of an activation process of the AWS unit in the endoscopic system according to the first embodiment.
Figure 18:
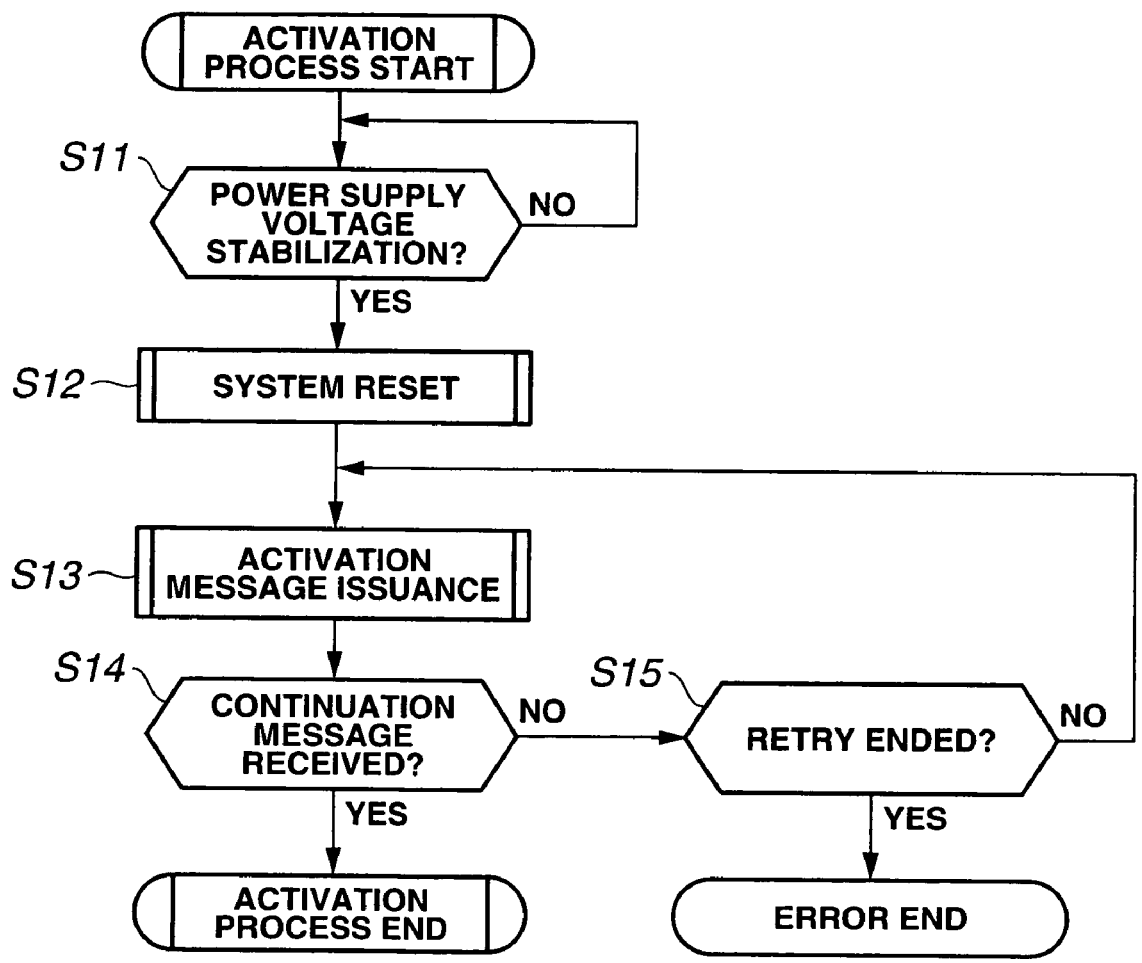
FIG. 18 is a flowchart showing an operation content of an activation process of the endoscope in the endoscopic system according to the first embodiment.

When the activation process is started, as shown in FIG. 17, first of all, in Step S1, the electric power transmission control section 128 in the power supply unit 75 of the AWS unit 4 shown in FIG. 15 puts the power supply transmission output section 127 in the electric power supply stop status, that is, the electric power supply is turned OFF.

After that, in Step S2, a monitor timer is turned ON, and then, as shown in Step S3, the transmission output section 127 is put in the electric power supply status, that is, the electric power supply is turned ON. As the power supply transmission output section 127 is in the electric power supply status, via the power line 73a in the tube unit 19 and further the electromagnetic coupling connection section 72a, the power supply circuit 98 in the control circuit 57 of the operation section 22 is supplied with the alternating current power.

After that, as shown in Step S4, the electric power transmission control section 128 is in a reception waiting status for an activation message via the signal line 73b in the tube unit 19 from the endoscope 3 side. Then, when the activation message is not received, as shown in Step S5, the electric power transmission control section 128 judges whether or not it is running out of time in the monitor timer. In the case where time is not running out, the flow returns to Step S4, and in the case of running out of time, the flow returns to the first Step S1.

On the other hand, in Step S4, when the activation message is received before running out of time, the electric power transmission control section 128 turns the time measurement of the monitor timer OFF as shown in Step S6. Then, as shown in Step S7, the continuance message is issued, and the activation process is ended.

Meanwhile, in the control circuit 57 of the endoscope 3, as the power supply generation section 98 is supplied with the alternating current power, necessary electric power for the operation in the control circuit 57 is supplied, and the activation process is started. Then, the status management section 81 shown in FIG. 13 waits, first of all, in Step S11, for stabilization of the power supply voltage in the power supply generation section 98.

When the power supply voltage is stabilized, in the next Step S12, the status management section 81 performs system resetting of the respective sections in the control unit 57. After the system reset, as shown in Step S13, the status management section 81 transmits the activation message via the transmission and reception unit 83 and further the signal line 73b in the tube unit 19 to the electric power transmission control section 128.

After the transmission of this activation message, as shown in Step S14, the status management section 81 waits for reception of a continuation message from the electric power transmission control section 128 side. When the continuation message is received, the activation operation is ended. On the other hand, when the continuation message is not received, as shown in Step S15, if a retry end condition (for example, a condition for the previously set number of retry times) is not met, the flow returns to Step S13, where the status management section 81 issues the activation message again. When the retry end condition is met, the error end is effected.

When the above-mentioned activation process is normally ended, image pickup by the CCD 25 is started. The user can perform airing/watering and suction operations, articulation operation, consistency varying operation, and the like through an operation part of the operation section 22.

Figure 19:
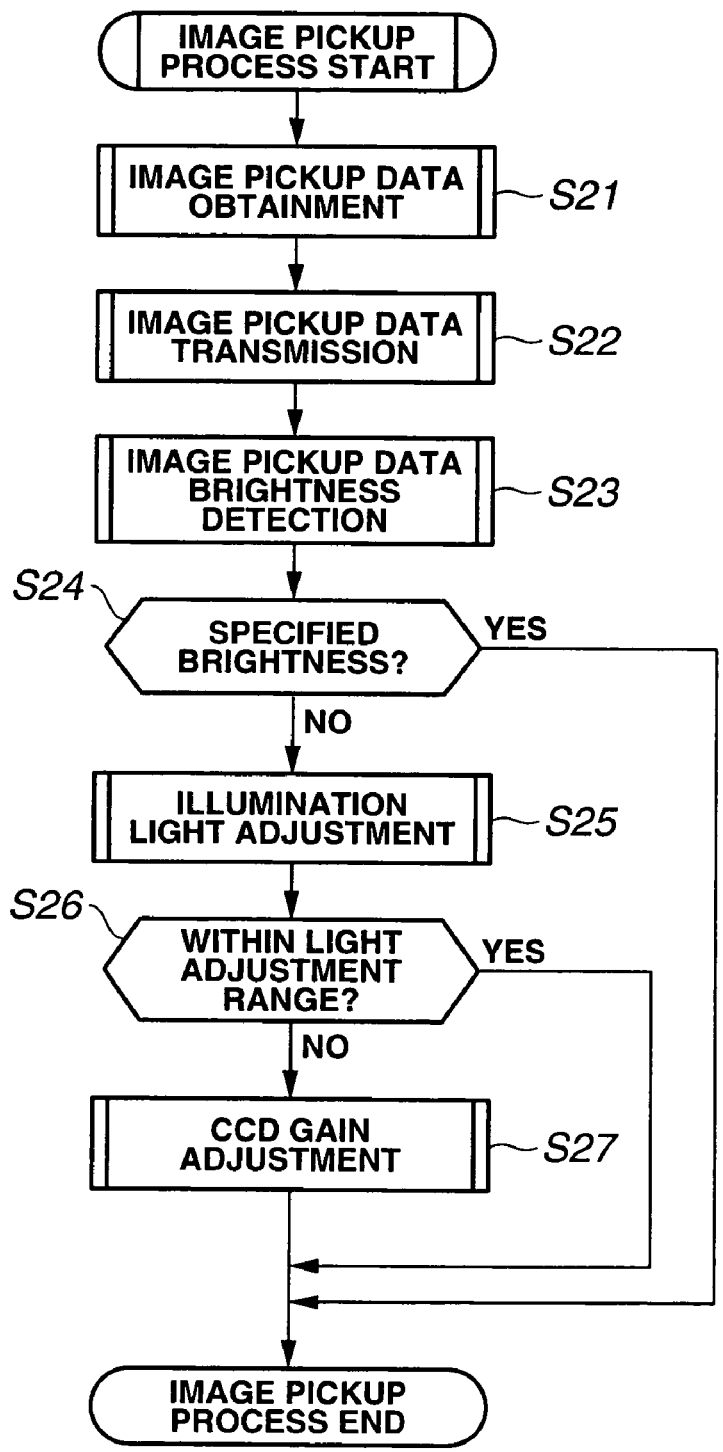
FIG. 19 is a flowchart showing an operation content of an image pickup control process in the endoscopic system according to the first embodiment.

Representative process operations regarding these various operations will be described with reference to FIG. 19 to FIG. 22. FIG. 19 shows an operation content of the image pickup control process.

As shown in FIG. 19, when the image pickup process is started, as shown in Step S21, the endoscope 3 obtains the image pickup data. To be specific, under the management (control) of the status management section 81, the LED 56 emits light, and at the same time the CCD driver section 86 starts an operation for driving the CCD 25. An image pickup signal captured by the CCD 25 is converted by the ADC 67 into a digital signal (image pickup data). The image pickup data (image data) is sequentially stored in the image memory 88, and the image pickup data is obtained.

The thus obtained image data is sequentially transmitted as shown in Step S22. The image data read from the image memory 88 is transmitted in a wired way from the transmission and reception unit 83 to the AWS unit 4, and further wirelessly transmitted from the transmission and reception unit 77 of the AWS unit 4 to the endoscopic system control device 5 side to be converted into a video signal inside the endoscopic system control device 5 and displayed on the observation monitor 6.

Then, the image pickup data of the ADC 87 is input to the brightness detecting section 89. As shown in Step S23, the brightness detecting section 89 calculates a mean value of the brightness data in the image pickup data over an appropriate time period or the like to detect the brightness in the image pickup data.

The detected data of the brightness detecting section 89 is input, for example, to the status management section 81, where it is judged whether or not the brightness is the instructed brightness (Step S24). Then, when the brightness is the instructed brightness, the image pickup process is ended, the flow shifts to the next image pickup process.

On the other hand, in Step S24, the status management section 81 judges that the brightness is not the instructed brightness, as shown in Step S25, an instruction signal for illumination light adjustment (control signal) is sent to the illumination control section 84, and the illumination control section 84 adjusts the illumination light quantity. For example, the illumination control section 84 adjusts the illumination light quantity by increasing or reducing a driving current for causing the LED 56 to emit the light, or the like. The illumination control section 84 returns the adjustment result to the status management section 81.

Thus, the status management section 81 judges whether or not the brightness is in the brightness adjustment range by the illumination control section 84 on the basis of information on the adjustment result. Then, when the brightness adjustment based on the illumination control section 84 can be performed, a process in Step S27 is not performed, and the image pickup process control is ended. On the other hand, when the brightness is out of the brightness adjustment range by the illumination control section 84, as shown in Step S27, the status management section 81 outputs a CCD gain adjustment signal to the CCD driver section 86 to adjust the gain of the CCD, thereby adjusting the brightness of the image pickup data. Then, the image pickup process is ended.

Next, an air water process of FIG. 20 will be described. As shown in FIG. 11, in general, functions of the air water switch and the suction switch are allocated on both sides of the track ball 69 in the operation section 22.

Figure 20:
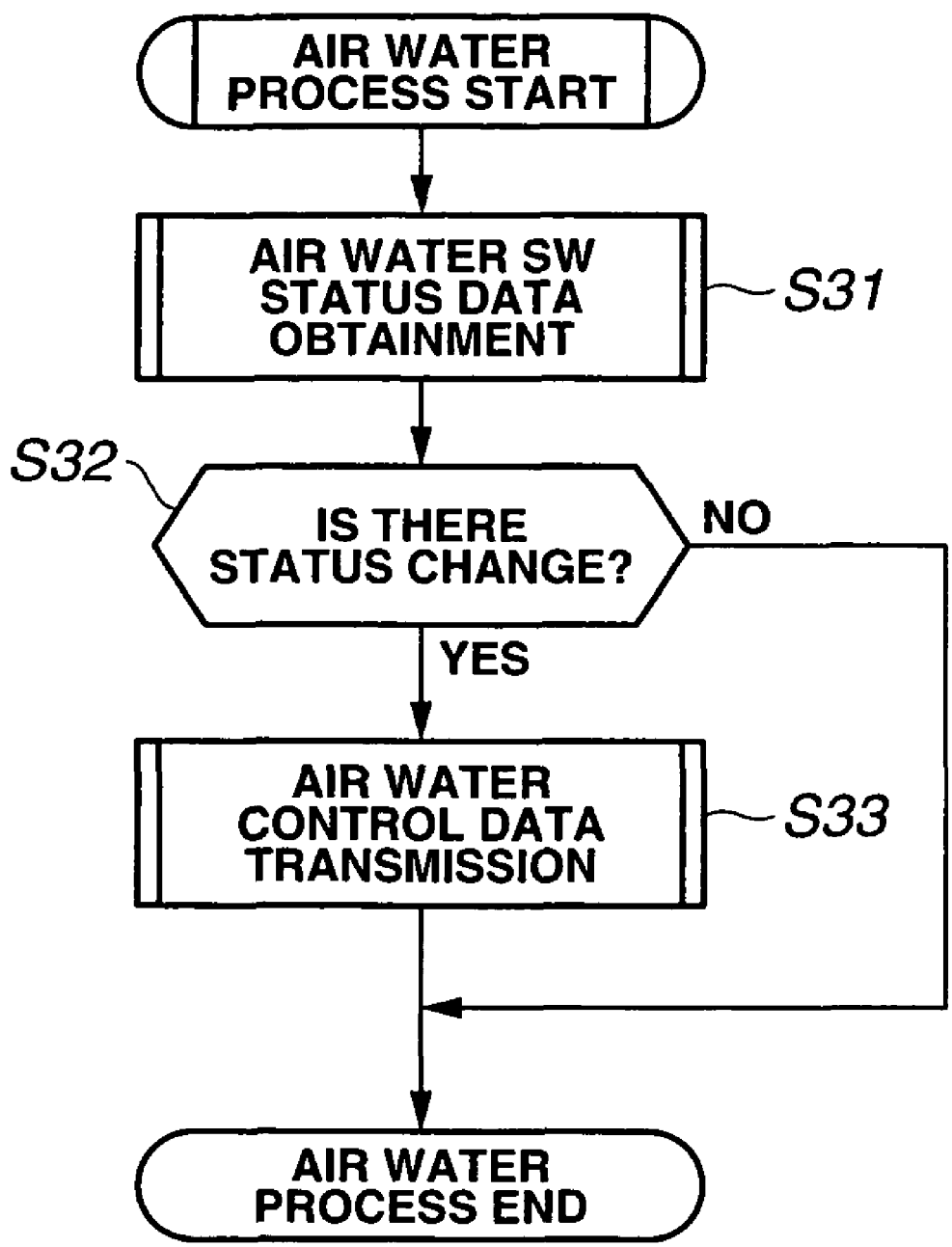
FIG. 20 is a flowchart showing an operation content of an air water control process in the endoscopic system according to the first embodiment.

When the air water process is started, as shown in Step S31 of FIG. 20, the status management section 81 of the control circuit 57 obtains the status data of the air water switch.

The operation of the air water switch is detected by the switch press detecting section 96 shown in FIG. 13. As the detection result information is input, the status management section 81 obtains the status data of the air water switch.

Then, as shown in Step S32, the status management section 81 judges whether or not there is a status change in the air water switch. In Step S32, when it is judged that there is a status change in the air water switch, as shown in Step S33, the status management section 81 sends the air water control data corresponding to the instruction of the air water switch operated by the user to the AWS unit 4 side via the transmission and reception unit 83.

The air water control section 122 in the AWS unit 4 performs the control operation for the pump 65 or the electromagnetic valve unit 124 in accordance with the air water control data. Then, the air water process operation is ended. On the other hand, in Step S32, when it is judged that there is no status change in the air water switch, a process in Step S33 is not performed, and the air water process operation is ended. It should be noted that the suction process is substantially the same as the air water process, so the process is omitted.

Next, with reference to FIG. 21, the articulation operation control process will be described. When the articulation control process is started, as shown in Step S41, the status management section 81 judges whether or not the articulation control is enabled.

According to this embodiment, regarding the track ball 69, the status management section 81 judges whether or not the articulation control is enabled as shown in Step S41 on the basis of whether or not the track ball 69 is pressed. To be specific, the status management section 81 can detect the displacement operation and the press operation of the track ball 69 on the basis of the output of the track ball displacement detecting section 95. It should be noted that when the track ball 69 is pressed, the articulation control is turned OFF.

The status management section 81 judges whether or not the articulation control is enabled on the basis of the output of the track ball displacement detecting section 95.

Then, when it is judged that the articulation control is not enabled, the flow shifts to Step S45, where the previous instructed value is held. On the other hand, when it is judged that the articulation control is enabled, the flow proceeds to the next Step S42, where the status management section 81 obtains the status data based on the operation of the track ball 69. Then, in the next Step S43, the status management section 81 judges whether or not there is a further status change on the basis of the output of the track ball displacement detecting section 95.

In this case, regarding the status management section 81, when it is judged that there is no status change, the flow shifts to Step S45. On the other hand, when it is judged that there is a status change, in the next Step S44, an instructed value corresponding to the rotation direction and the rotation amount of the track ball 69 is calculated.

After the process in Step S44 or S45, as shown in Step S46, the status management section 81 sends the instructed value to the actuator driver section 92 via the articulation control section 91 to perform the servo process on the articulation actuator.

That is, the actuator driver section 92 drives the articulation actuator so that an articulation angle (bending direction) corresponding to the instructed value is obtained on the basis of the instructed value. At that time, the articulation status of the articulation actuator is detected by the encoder, and, The actuator driver section 92 drives the articulation actuator so that the detected value matches the instructed value. In this way, this articulation control process is ended.

Figure 21:
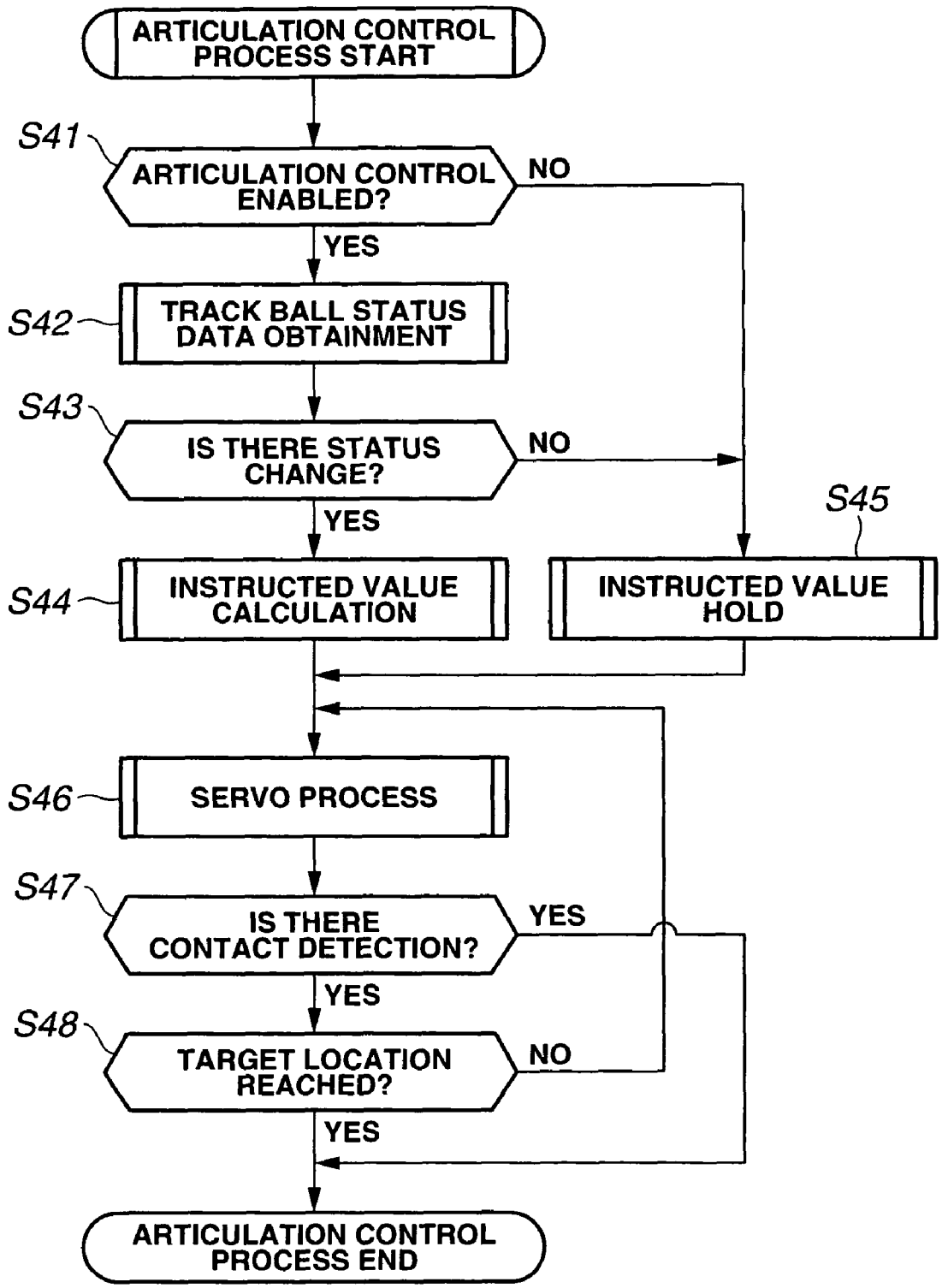
FIG. 21 is a flowchart showing an articulation operation control process in the endoscopic system according to the first embodiment.

It should be noted that FIG. 21 also shows process operations (in Steps S47 and S48) in the case where a contact sensor to be described in a second embodiment is provided at the time of the serve process in Step S46. The processes in Steps S47 and S48 will be described in the second embodiment.

Figure 22:
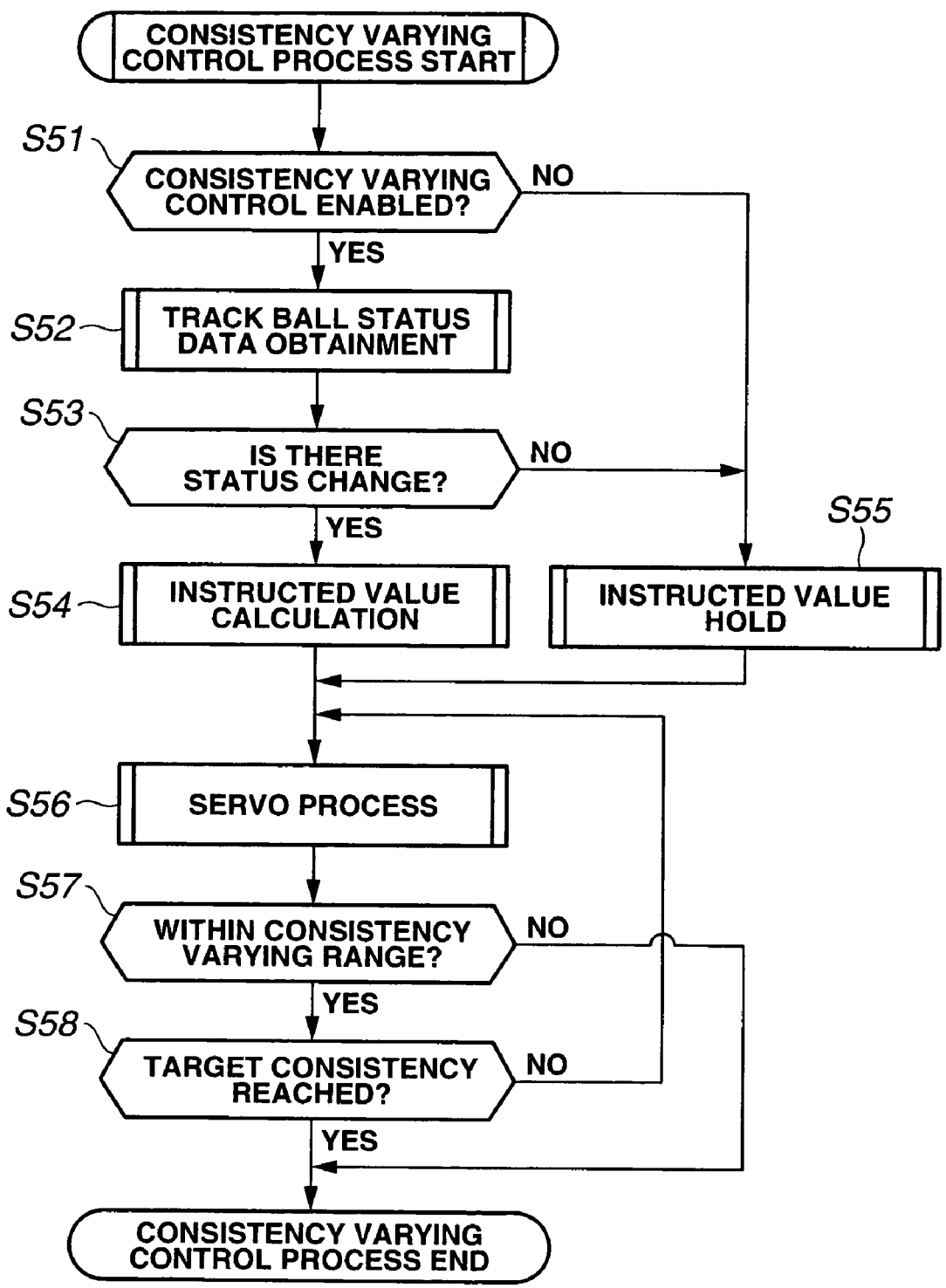
FIG. 22 is a flowchart showing a control operation for a consistency varying operation in the endoscopic system according to the first embodiment.

Next, with reference to FIG. 22, a control process for varying the consistency will be described. In this control process, basically the same control process as in FIG. 21 is performed.

When the control process for varying the consistency is started, as shown in Step S51, the status management section 81 judges whether or not the consistency varying control is enabled.

To be specific, as shown in FIG. 16B, from the main menu, the insert section consistency is allocated to one of the function switches SW1 to SW5. The status management section 81 judges whether or not the function switch of the insert section consistency is pressed to be enabled. When it is judged that the consistency varying control is not enabled, the flow shifts to Step S55, where the status management section 81 holds the previous instructed value. On the other hand, when it is judged that the consistency varying control is enabled, the flow proceeds to the next Step S52, where the status management section 81 obtains the status data by the operation of the track ball.

Then, in the next Step S53, the status management section 81 judges whether or not there is a further status change on the basis of the output of the track ball displacement detecting section 95.

In this case, when it is judged that there is no status change, the process shifts to Step S55, and on the other hand when it is judged that there is a status change, in the next Step S54, the status management section 81 calculates the instructed value corresponding to the rotation direction and the rotation amount of the track ball 69.

After the process in Step S54 or S55, as shown in Step S56, the status management section 81 sends the instructed value via the consistency varying control section 93 to the actuator driver section 94, for performing the servo process on the consistency varying actuator 54A or 54B.

In other words, the actuator driver section 94 drives the consistency varying actuator 54A or 54B so that the target consistency corresponding to the instructed value is obtained on the basis of the instructed value. At that time, the consistency variable status of the consistency varying actuator 54A or 54B is detected by the encoder 54c, and the actuator driver section 94 drives the consistency varying actuator 54A or 54B so that the value detected by the encoder 54c reaches the target consistency.

In Step S57 which is in a midway for performing such a servo process, the consistency varying control section 93 or the status management section 81 judges whether or not this value is in the variable range of the consistency varying actuator 54A or 54B on the basis of the actuator driver section 94. When this value is out of the variable range, the consistency varying control process is ended.

Also, in Step S57, when this value is in the variable range of the consistency varying actuator 54A or 54B, further in the next Step S58, the consistency varying control section 93 or the status management section 81 judges whether or not the value reaches the target consistency. When the value does not reach the target consistency, the flow returns to Step S56 to continue the servo process. In this way, when the value reaches the target consistency, the consistency varying control process is ended.

Then, the UPD unit 76 detects the positions of the UPD coils 58 arranged in the insertion section 21 of the endoscope 3 by the UPD coil unit 8 to calculate the insertion shape of the insertion section 21. The shape of the insertion section, in other words, the UPD image is displayed on a display screen of the observation monitor 6.

FIGS. 23A to 23D show a state in which menu screens on the right hand side respectively correspond to UPD images on the left hand side. Consistency parts of the consistency varying actuators 54A and 54B provided at plural positions (two positions in the specific example) in the case in which the user selects and sets the consistency of the consistency varying actuators 54A and 54B from the menu screen are displayed in a color corresponding to the set consistency, whereby the consistency of the part becomes easy to distinguish.

Figure 23A:
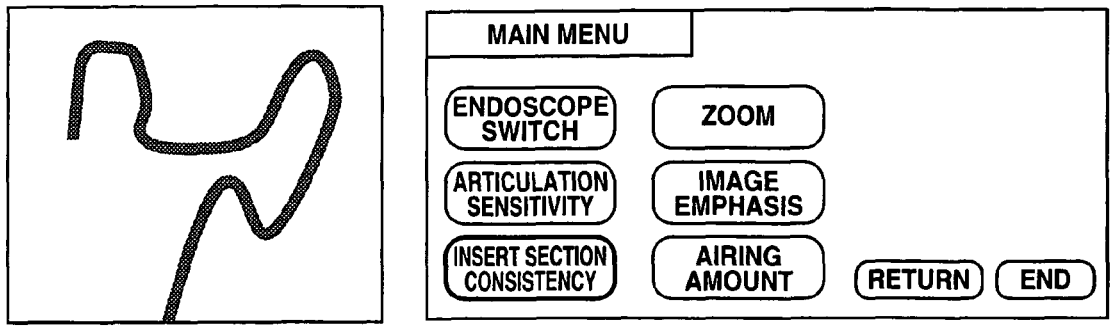
FIG. 23A is an operation explanatory diagram showing a consistency variable setting operation and a UPD image corresponding to the operation in the endoscopic system according to the first embodiment.

FIG. 23A shows a display state of the main menu. FIG. 23A shows the case in which the user in this display state selects the insert section consistency variable. In this case, the UPD image is displayed in a state in which sections A and B of the consistency varying actuators 54A and 54B are displayed in a color which is not distinguished from sections other than the sections A and B, as immediately before the insert section consistency variable is selected.

Figure 23B:
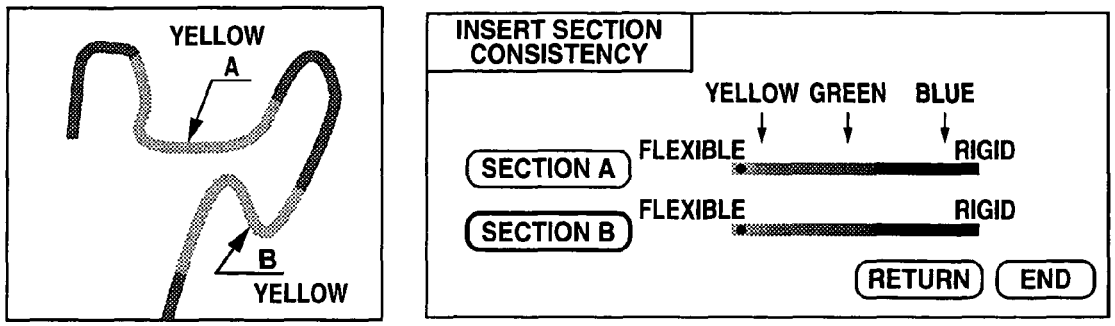
FIG. 23B is an operation explanatory diagram showing the consistency variable setting operation and the UPD image corresponding to the operation in the endoscopic system according to the first embodiment.

As shown in FIG. 23B, when the insert section consistency variable is selected, section ranges regarding the consistency set to the sections A and B of the consistency varying actuators 54A and 54B at the two positions are shown. A consistency setting screen is displayed in which the consistency is set between a flexible state to a rigid state in the sections A and B. The current consistency is indicated by a circle in the respective sections. In this case, the flexible state to the rigid state are displayed in different colors.

Therefore, the corresponding UPD image is displayed in a display color corresponding to the consistency at which the consistency varying actuator is set, with the part of the consistency varying actuator being displayed in color. In the state of FIG. 23B, the consistency section is set close to the flexible state. The sections A and B of the consistency varying actuator 54A and 54B in the UPD image in this case are shown in yellow.

Figure 23C:
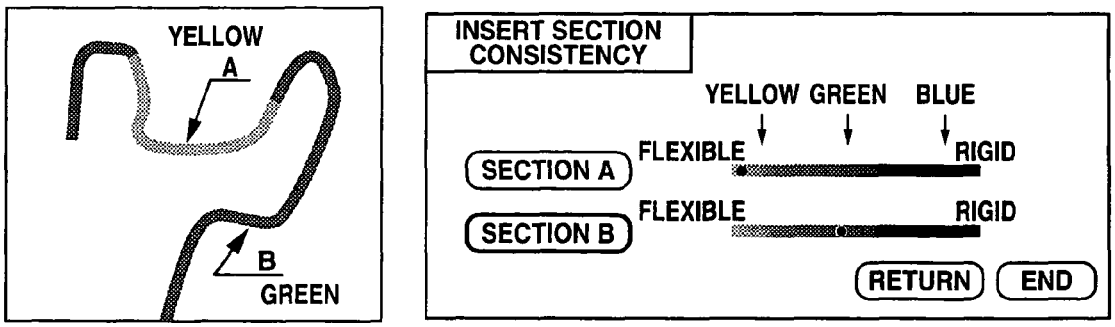
FIG. 23C is an operation explanatory diagram showing the consistency variable setting operation and the UPD image corresponding to the operation in the endoscopic system according to the first embodiment.

FIG. 23C shows the case in which the consistency of the section B of the consistency varying actuator 54B is set in the vicinity of the center in the state of FIG. 23B, for example. The section B of the consistency varying actuator 54B in the UPD image in this case is shown in green.

Figure 23D:
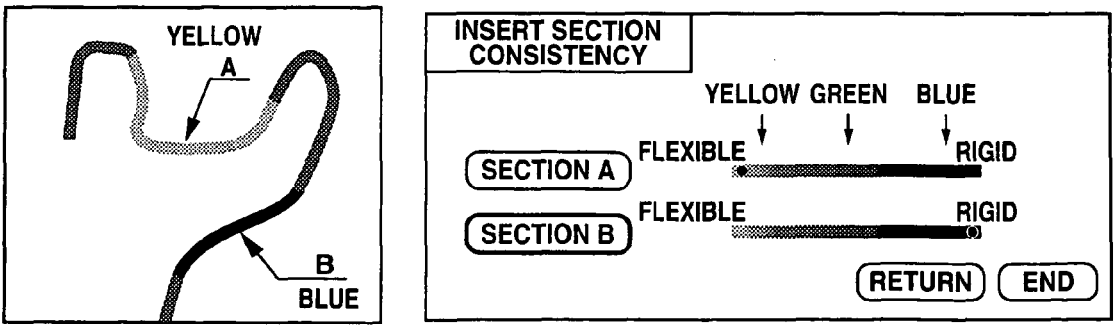
FIG. 23D is an operation explanatory diagram showing the consistency variable setting operation and the UPD image corresponding to the operation in the endoscopic system according to the first embodiment.

Then, FIG. 23D shows the case in which the consistency of the section B of the consistency varying actuator 54B is set to the rigid state (a value showing the rigid state) in the state of FIG. 23B or 23C, for example. The section B of the consistency varying actuator 54B in the UPD image in this case is displayed in blue.

By displaying in this way, the user can freely set the consistency of the consistency varying actuators 54A and 54B, and the thus set sections A and B of the consistency varying actuators 54A and 54B are displayed in a display color corresponding to the set consistency. Thus, the user can easily distinguish the consistency of the consistency varying actuators 54A and 54B.

Also, the shape of the insert section 21 can be displayed with use of the UPD coils 58, and thus the surgeon can easily conduct the insertion operations and the like.

Next, the process content of a human interface for realizing the remote control operations by the user on the endoscope 3 side and on the endoscopic system control device 5 side will be described with reference to FIGS. 24 and 25. It should be noted that in FIGS. 24 and 25, the human interface is abbreviated as HMI.

Figure 24:
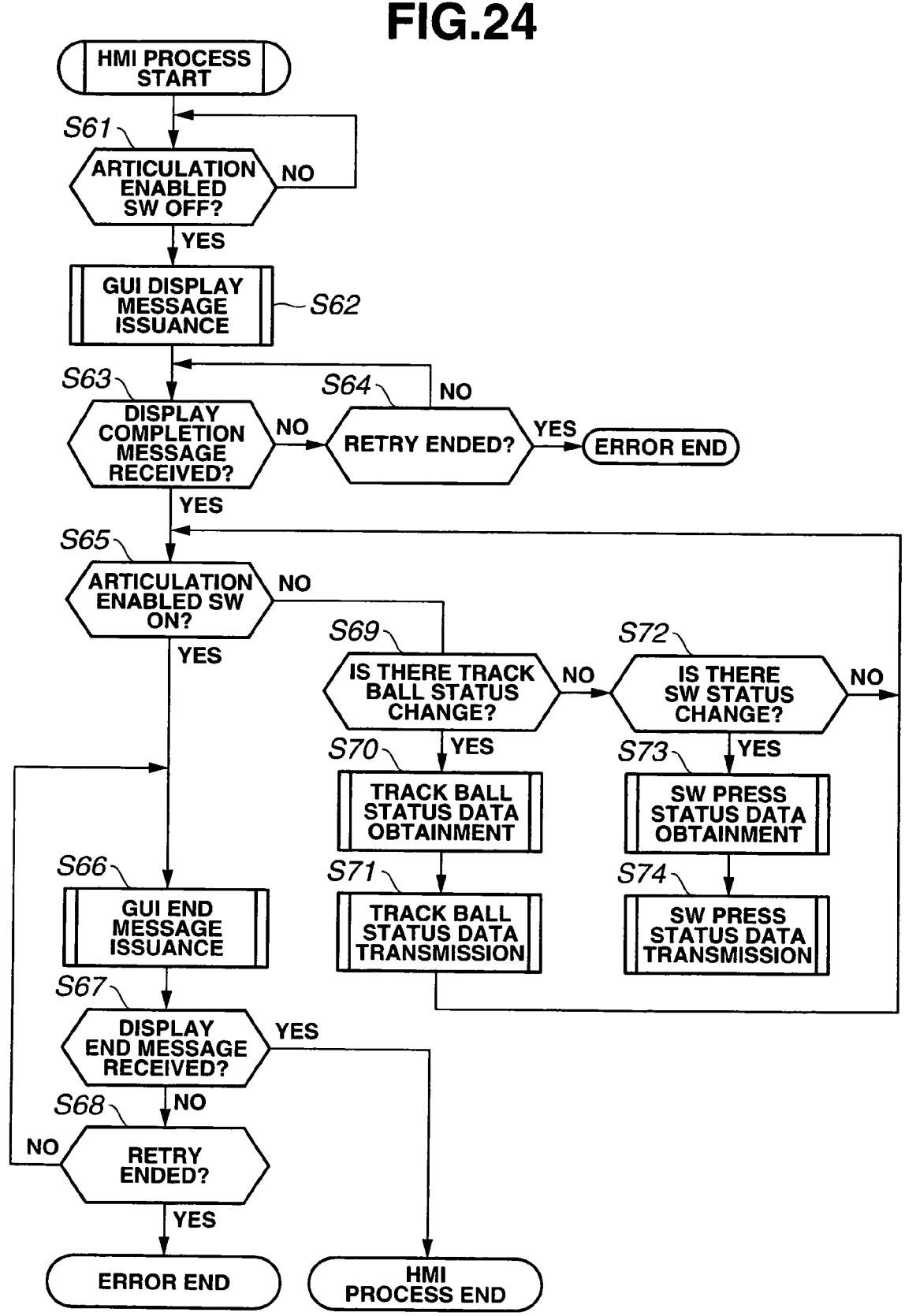
FIG. 24 is a flowchart showing a content of a human interface process on the endoscope side in the endoscopic system according to the first embodiment.

As shown in FIG. 24, when the human interface process is started, the status management section 81 waits a moment in which an articulation enabled switch is turned OFF. That is, the status management section 81 waits a moment in which the articulation enabled switch is turned OFF after the track ball 69 is pressed.

Then, when the articulation enabled switch is turned OFF, as shown in the next Step S62, the status management section 81 issues a GUI (graphical user interface) display message. This GUI display message is wirelessly sent from the endoscope 3 via the AWS unit 4 to a CPU (control CPU) in a system control unit 117 of the endoscopic system control device 5.

After the status management section 81 issues the GUI display message, in the next Step S63, the status management section 81 waits for the GUI display completion message reception from the endoscopic system control device 5 side. Then, when the GUI display completion message cannot be received, the flow proceeds to Step S64, where the status management section 81 judges whether or not this is corresponding to a retry end condition. When this is not corresponding to the retry end condition, the flow returns to Step S63, and on the other hand when this is corresponding to the retry end condition, the error end is effected.

In the process in Step S63, the status management section 81 judges whether or not the articulation enabled switch is turned ON when the display completion message is received, and the flow shifts to Step S65. When the articulation enabled switch is turned ON the status management section 81 issues a GUI end message as shown in Step S66.

The GUI end message is sent wirelessly via the AWS unit 4 to the endoscopic system control device 5 similar to the case of the GUI display message from the endoscope 3. Then, after issuing the GUI end message, the status management section 81 waits for a GUI display end message reception from the endoscopic system control device 5 side in the next Step S67. When this GUI display end message is received, the status management section 81 terminates this human interface process.

On the other hand, when this GUI display end message cannot be received, the flow proceeds to Step S68, where the status management section 81 judges whether or not this is corresponding to the retry end condition. When this is not corresponding to the retry end condition, the flow returns to Step S66, and on the other hand when this is corresponding to the retry end condition, the error end is effected.

Furthermore, in Step S65, when the articulation enabled switch is not turned ON, the flow shifts to the process in the menu screen on the Step S69 side. In this Step S69, the status management section 81 judges whether or not there is a status change in the track ball 69 on the basis of whether or not there is a change amount equal to or larger than a certain threshold from the output of the track ball displacement detecting section 95.

Then, as shown in Step S70, when it is judged that there is a change regarding the status in the track ball 69, the status management section 81 obtains the status data of the track ball 69 (change data).

In this case, the user can select and instruct a desired function of the item with use of a cursor moving in accordance with the operation of the track ball 69 on the menu screen in FIG. 16B.

Then, as shown in Step S71, the status management section 81 transmits the status data corresponding to the operation of the track ball 69 by the user. The status data is transmitted as packet data in sync with the image pickup data of the CCD 25 from the endoscope 3 via the AWS unit 4 to the endoscopic system control device 5. After the transmission of the status data, the flow returns to the process in Step S65.

In Step S69, when it is judged that there is no change in the status of the track ball 69, as shown in Step S72, the status management section 81 judges whether or not there is a change in the switch status (the switches SW1 to SW5) on the basis of the detection output from the switch press detecting section 96.

In Step S72, when there is no change in the switch status, the flow returns to Step S65, and on the other hand when there is a change in the switch status, as shown in Step S73, the status management section 81 obtains the switch press status data. Furthermore, in the next Step S74, the thus obtained switch press data is transmitted, whereby the flow returns to the process in Step S65.

Figure 25:
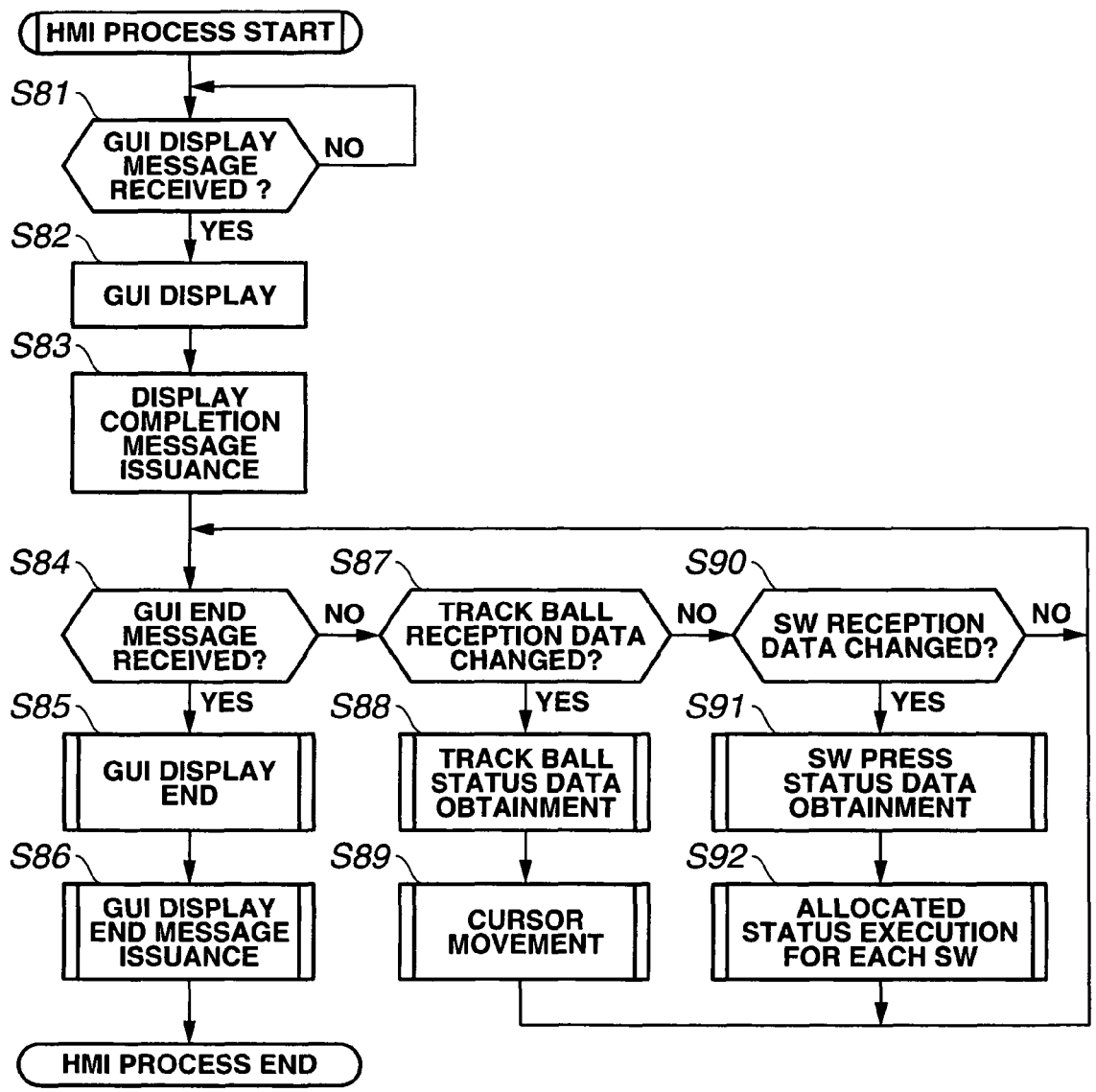
FIG. 25 is a flowchart showing a content of the human interface process on the endoscopic system control device side in the endoscopic system according to the first embodiment.

On the other hand, as shown in FIG. 25, when the human interface process is started, the CPU of the system control unit 117 in the endoscopic system control device 5, in the first Step S81, waits for the GUI display message reception from the endoscope 3 side. The CPU waits for the wireless GUI display message reception via the transmission and reception unit 101 of FIG. 8 or 14.

Then, as shown in Step S82, the CPU of the system control unit 117 performs the control process for the GUI display when the GUI display message is received. That is, the CPU performs the control for the GUI display with respect to the image processing unit 116.

After the GUI display process in Step S82, as shown in Step S83, the CPU issues a display completion message. The CPU transmits this display completion message via the transmission and reception unit 101. In the next Step S84, the CPU judges whether or not the GUI end message is received from the endoscope 3 side. Then, when the GUI end message is received, in Step S85, the CPU performs a process for ending the GUI display. After that, in the next Step S86, the CPU further issues a GUI display end message, and thereafter the human interface process is ended.

In Step S84, when the GUI end message is not received, the flow shifts to Step S87, where the CPU judges whether or not there is a change in the reception data of the track ball 69. The judgment as to whether or not there is a change in the reception data of the track ball 69 is performed in response to reception of the judgment result of the endoscope 3 side as to whether or not there is a status change in the track ball 69. When it is judged that there is a change in the reception data, as shown in Step S88, the status data of the track ball 69 is obtained. Furthermore, in the next Step S89, the CPU moves the cursor by the movement amount corresponding to the thus obtained status data of the track ball 69 (change data). Then, the flow returns to the process in Step S84.

On the other hand, in the process in Step S87, when it is judged that there is no change in the reception data of the track ball 69, the CPU judges whether or not there is a change in the reception data of the switch as shown in Step S90, on the basis of the transmitted information on the judgment result on the endoscope 3 side.

When there is a change in the reception data of the switch as shown in Step S91, the CPU obtains the switch press status data on the basis of the transmitted information from the endoscope 3 side. Furthermore, as shown in Step S91, the CPU performs a process for executing the function allocated to the switch, which has been pressed, and the flow returns to the process in Step S84. Also there is no change in the reception data of the switch in Step S90, the flow returns to the process in Step S84.

Regarding the endoscope 3 according to this embodiment which forms the endoscopic system 1 for performing the above-mentioned operations, the endoscope 3 is set to be separated into the endoscope main body 18 and the tube unit 19 in the operation section 22 to provide the disposal tube unit 19, thereby easily conducting washing or sterilization of the endoscope main body 18.

That is, the air water duct line 60a and the suction duct line 61a in the endoscope main body 18 are made much shorter than the conventional case where a universal cable corresponding to the tube unit 19 is integrally formed and thus the washing and sterilization can also be easily performed.

At this time, in the conventional case where a universal cable corresponding to the tube unit 19 is integrally formed, the universal cable is adjacently provided to the operation section 22 so as to be bent. In the connector section 51 of the operation section 22 of this embodiment, the duct line connector section 51a is only slightly bent, and the other parts are composed of the air water duct line 60a and the suction duct line 61a, which extend in a substantially straight manner. Therefore, the processes for the washing, sterilization, and drying inside the duct line can be performed easily in a short period of time. Thus, the state in which the endoscope inspection becomes executable can be set in a short period of time.

Also, in this embodiment, the endoscope main body 18 and the tube unit 19 are detachably attached with the connection section without relying on the mutual metal electrode connection. Even when the endoscope main body 18 is subjected to repeated washing or sterilization, no contract conduction failure or the like is generated, thereby improving the reliability.

Moreover, in this embodiment, the operation section 22 has a large number of operation sections such as the articulation operation section, the air water operation section, the suction operation section, the consistency varying operation section, the freeze operation section, and the release operation section, and at the same time these operation sections are structured to be collectively (in a concentrate manner) controlled by the control circuit 57 provided in the operation section 22. In addition, the control circuit 57 has the collective control structure along with the light emitting section for outputting the illumination light for image pickup and the image pickup section for performing the image pickup.

In this way, according to this embodiment, the various functions provided to the endoscope main body 18 are collectively controlled by the control circuit 57 provided inside the operation section 22, and also the various functions for the AWS unit 4 connected to the endoscope main body 18 and the operation section for the endoscope system control device 5 for wirelessly performing the transmission and reception of information are collectively controlled, so the user (more specifically, the surgeon) can freely perform the various operations with the various operations sections provided to the operation section 22, thus greatly improving the operability.

In particular, in this embodiment, as the control circuit 57 for performing the collective control is provided inside the operation section 22, from the control circuit 57, the image data captured by the CCD 25 and the various signals of the operation sections are commonly transmitted by the pair of the signal lines 71b in the form of packet. Thus, it is possible to reduce the number of the electric signal lines (to be specific, the number is reduced to two for the signal transmission lines and two electric power transmission lines. If one of the signal lines and one of the transmission lines are commonly used, the number can be three in total).

Thus, the number of the signal lines necessary be to inserted through the tube unit 19 to be connected in the connection section in the operation section 22 can also be reduced, and the tube unit 19 side can be used for disposal application.

Also, by reducing the number of the signal lines inserted through the tube unit 19, the tube unit 19 can have a smaller diameter and be easily bent. When the user operates the tube unit, the operability can be improved.

Figure 26:
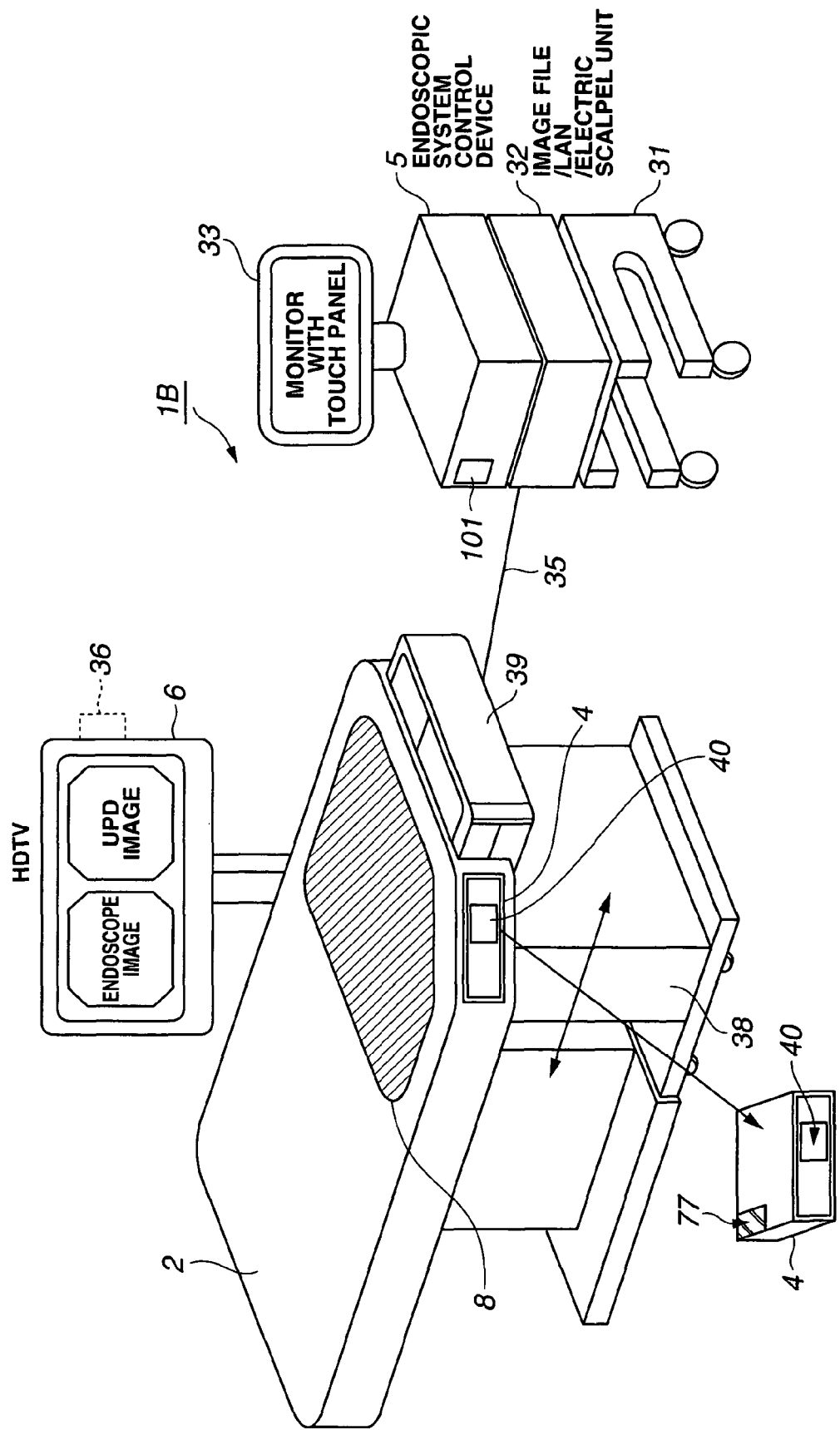
FIG. 26 is an outer appearance perspective view showing a structure of a modified example of the endoscopic system according to the first embodiment.

It should be noted that an endoscopic system 1B having a structure shown in FIG. 26 may be used as a modified example of the endoscopic system of the first embodiment according to the present invention.

The endoscopic system 1B accommodate the AWS unit 4 in the concave section provided to the upper end surface of the inspection bed 2, in the endoscopic system shown in FIG. 4.

The AWS unit 4 has the wireless transmission and reception unit 77 shown in FIG. 8, for example, on the upper surface. When the AWS unit 4 is accommodated in the concave section, as the endoscope connector 40 is provided on the front face exposed to the outside, the endoscope connector 41 of the endoscope 3 can be detachably connected.

The other structure is the same as that in the case of FIG. 4. In the case of this structure, when the endoscope inspection or the like is performed with the endoscope 3, as the AWS unit 4 is attached to the inspection bed 2, without so much extending the tube unit 19 from the endoscope 3, the connection to the AWS unit 4 can be achieved, thereby providing an environment for the facilitated operation to the surgeon. The other structure has the same effect as that in the case of the endoscopic system 1.

Next, the second embodiment of the present invention will be described.

Figure 27:
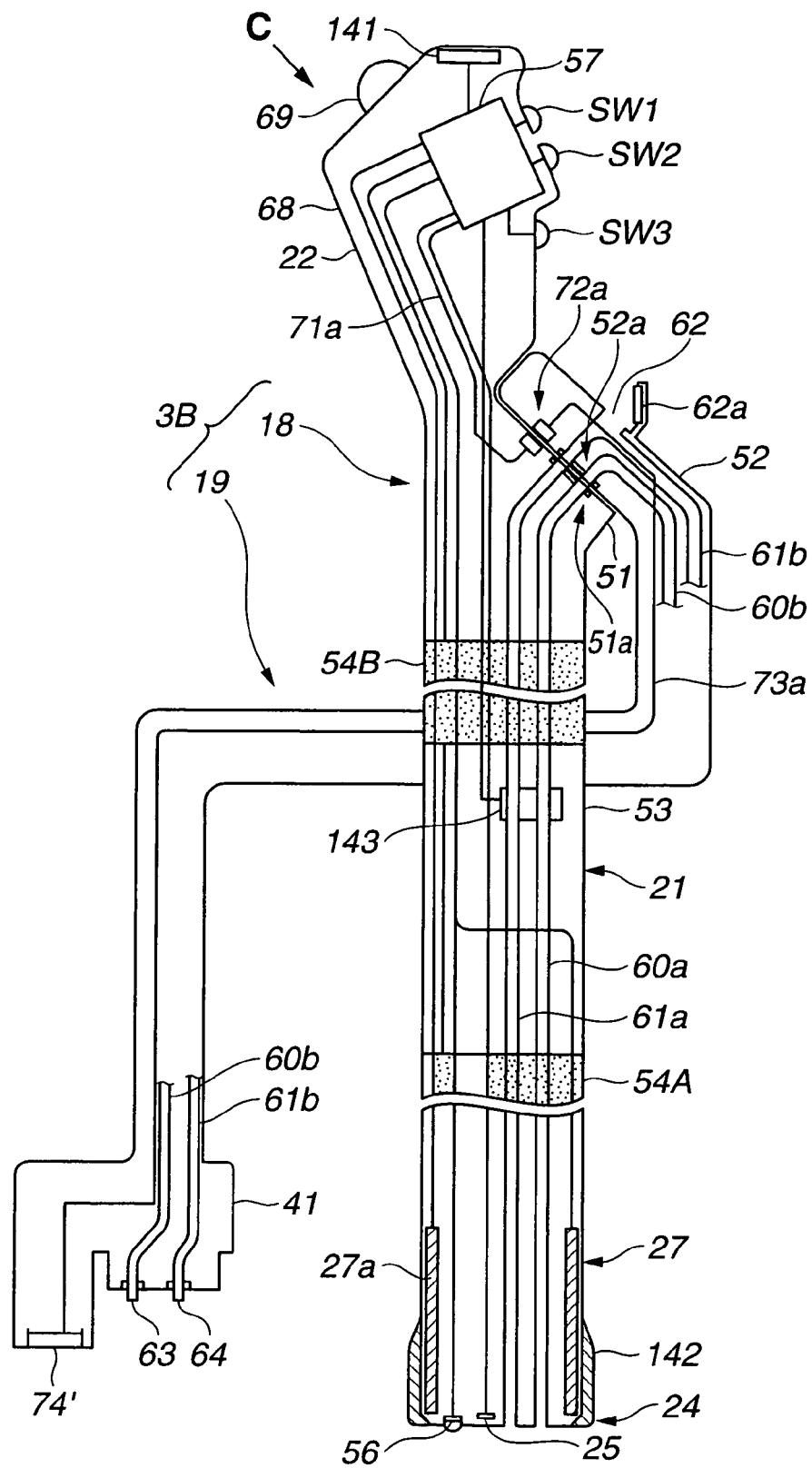
FIG. 27 is a side view with a see-through of a part of internal components of the endoscope in the endoscopic system according to a second embodiment of the present invention.
Figure 28A:
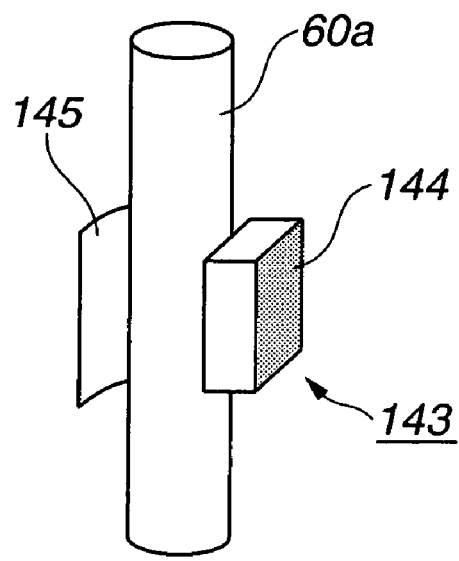
FIG. 28A shows a structure of a transparency sensor of the endoscope in the endoscopic system according to the second embodiment.
Figure 28B:
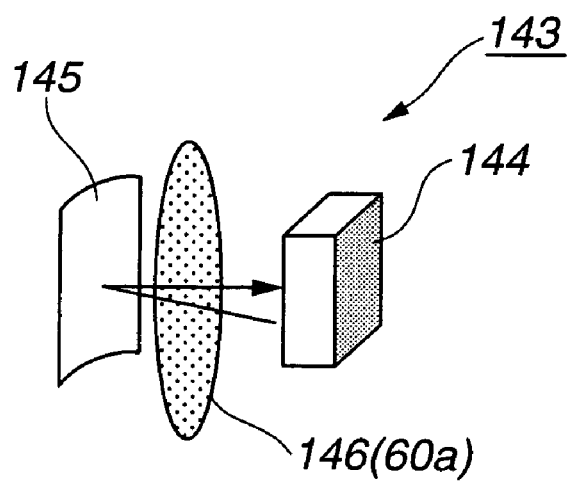
FIG. 28B shows an operation of the transparency sensor of the endoscope in the endoscopic system according to the second embodiment.
Figure 29:
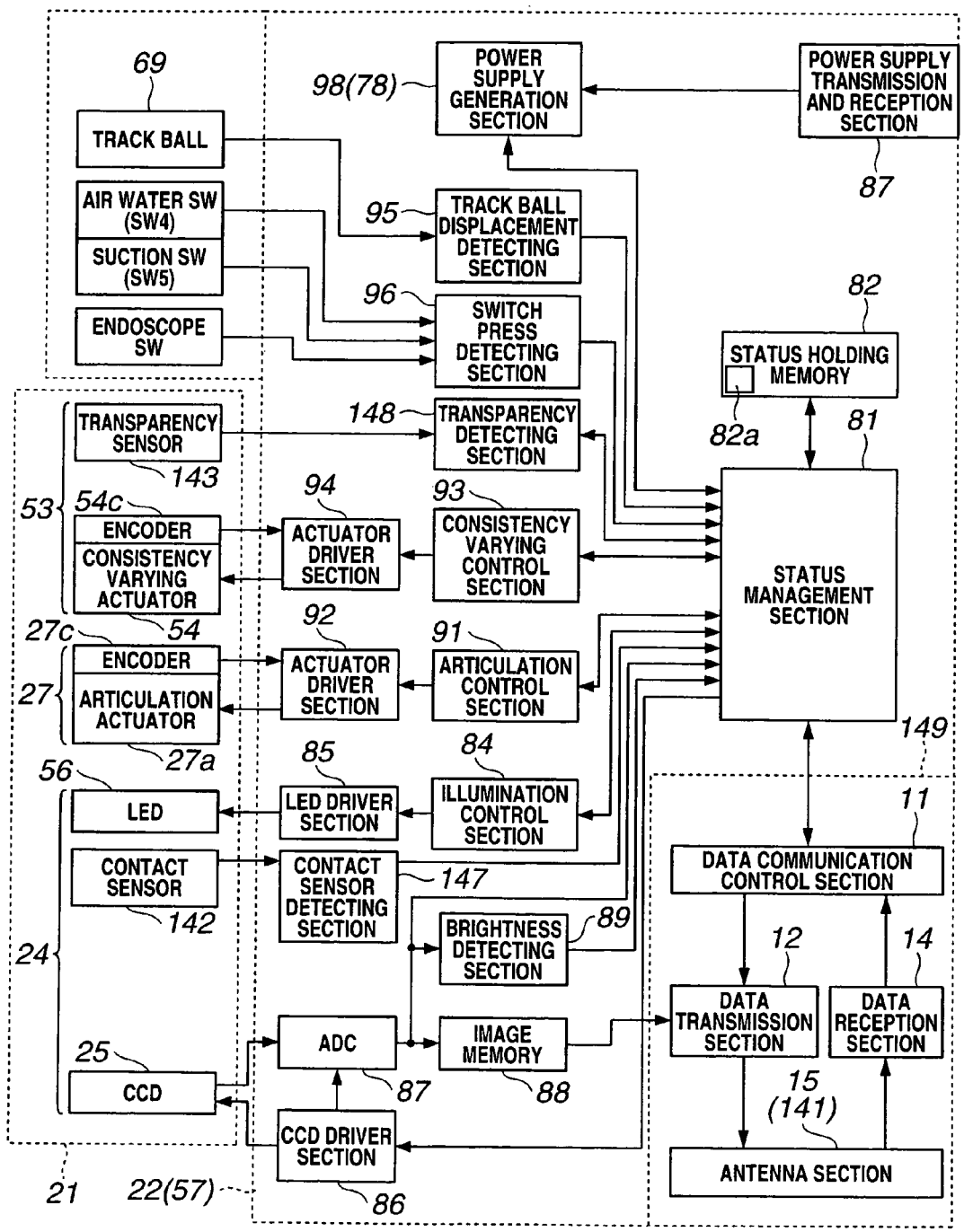
FIG. 29 is a block diagram showing an electric structure of the endoscope in the endoscopic system according to the second embodiment.

FIG. 27 is a side view with a see-through of a part of internal components of the endoscope in the endoscopic system according to the second embodiment of the present invention. FIGS. 28A and 28B are main part perspective views showing a transparency sensor of the endoscope in the endoscopic system according to the second embodiment. FIG. 29 is a block diagram showing an electric structure of the endoscope in the endoscopic system according to the second embodiment.

As shown FIG. 27, the endoscope 3B of this embodiment does not have a section corresponding to the signal line 71b of the endoscope 3 in the first embodiment. With an antenna section 141 provided in the operation section 22, the image pickup data by the CCD 25, various data, and the like are wirelessly transmitted and received with the AWS unit 4. That is, in the endoscope of the first embodiment, the signal line 71b functions as the wired common signal transmission section for various signals. Whereas in the second embodiment, the antenna section 141 that forms a wireless common signal transmission section for various signals is adopted.

For this reason, the connector section 51 in the operation section 22 of the endoscope main body 18 according to this embodiment does not have the electromagnetic connection section 72b connected to the signal line 71b in the first embodiment. In addition, the signal line 73b is not inserted through the tube unit 19 side (in the tube unit 19 in the case of FIG. 9).

Therefore, the air water duct line 60b, the suction duct line 61b, and the power supply line 73a are inserted through the tube unit 19. For this reason, the electric connector 74' in the connector 41 has only a connection section of the power supply line 73a.

According to this embodiment, the structure inside the tube unit 19 can be simplified as compared with that of the first embodiment, so the lower cost can be achieved, and also the tube unit 19 can be suitable to the disposal application.

Also, in this embodiment, a contact sensor 142 is provided to the outer peripheral surface of the distal end section 24. The contact sensor 142 is connected to the control circuit 57 via a signal line. Then, when an articulation operation is performed, on the basis of a detection result from the contact sensor 142, a control is performed to regulate the bending of the bending section 27 at that time. With this control being performed, the bending section 27 does not impart unnecessary stress on the inner wall of the body cavity for reducing the pain. For example, when the insert section is inserted in the body cavity, the smooth insertion can be performed while the pain on the patient is reduced.

Furthermore, in this embodiment, a transparency sensor 143 for detecting the transparency of a fluid inside the air water duct line 60a and the suction duct line 61a is provided at an appropriate position in the midway in the longitudinal direction of the insert section 21. A detection signal from the transparency sensor 143 is sent to the control circuit 57. It should be noted that according to the second embodiment, such a structure is adopted that the UPD coil 58 in the first embodiment is not arranged.

FIGS. 28A and 28B are an explanatory diagram for the operation of the washing level detection by the transparency sensor 143.

As shown in FIG. 28A, a photo reflector 144 and the reflection mirror 145 are arranged so as to oppose to each other on the outer periphery of the air water duct line 60a (same in the suction duct line 61a) formed of a transparent tube, thereby forming the transparency sensor 143.

Then, as shown in FIG. 28B, the light emitted by the light emitting element forming the photo reflector 144 is output to the reflection mirror 145 side, and the reflection light reflected by the reflection mirror 145 is received by a light reception element forming the photo reflector 144.

In this case, in actuality, as a transmittance detection body 146 such as the air water duct line 60a formed of a transparent tube is arranged between the photo reflector 144 and the reflection mirror 145, when a transparent washing liquid is poured into the inner wall side of the air water duct line 60 to wash the air water duct line 60a, once the inner wall surface is in a clean state, the light reception element of the photo reflector 144 receives larger light quantity, so the washing degree can be detected.

Therefore, with this function, the washing level of the inner wall surface of the air water duct line 60a and that of the inner wall surface of the suction duct line 61a can be quantitative detected.

It should be noted that with the description in this case, the effect in the washing with the washing liquid is described, but during the endoscopic inspection or the like, by referring to the detection output from the transparency sensor 143, it is also possible to find out the contamination degree of the inner wall of the air water duct line 60a and that of the inner wall of the suction duct line 61a.

FIG. 29 shows an electric structure in the case of the endoscope 3B according to this embodiment.

According to the second embodiment, as compared with the first embodiment, the contact sensor 142 is further provided at the distal end section 24 to be connected to the status management section 81 via a contact sensor detection section 147 for conducting contact detection on the basis of the detection output from the contact sensor 142.

Also, for example, the flexible portion of the insert section 21 further includes the transparency sensor 143 to be connected to the status management section 81 via a transparency detection section 148 for detecting the transparency on the basis of the detection output from the transparency sensor 143.

Moreover, in this embodiment, instead of the wired transmission and reception unit 83 shown in FIG. 13, a transmission and reception unit 149 for wirelessly performing transmission and reception is adopted. In the first embodiment, the image data and operation data such as the switch input to the electric connector 43 of the AWS unit 4 are all received in the data communication control section 11 of the endoscopic system control device 5 similarly to the first embodiment.

In the data communication control section 11 of the AWS unit 4, the AWS related information such as the operations of the air water switch or the suction switch is only received, and then sent to the air water control section 122 to control the pump 65 and the electromagnetic valve unit 124. It should be noted that this embodiment does not include the UPD coil 58.

According to the second embodiment, when the status management section 81 performs the articulation operation control for the articulation operation, as shown in FIG. 21, during the servo process activation in Step S46, the status management section 81 takes in the detection result from the contact sensor 142 via the contact sensor detection section 147 as shown in Step S47, where a detection (judgment) as to whether or not the distal end section 24 contacts the inner wall in the body cavity or the like in a pressure equal to or larger than an appropriate value is conducted.

Then, when the status management section 81 judges that the contact is not in a pressure equal to or larger than the appropriate value, the flow proceed to the next Step S48, where it is judged on the basis of the encoder detection value whether or not the target position corresponding to the articulation instructed value is reached. When the target position is not reached, the flow returns to Step S46, and when the target position is reached, the control process for the articulation operation is ended.

On the other hand, in Step S47, when the status management section 81 judges that the contact is in a pressure equal to or larger than the appropriate value, the process in the next Step S48 is not performed, and the control process for the articulation operation is ended.

In this way, when the articulation operation is performed, the status management section 81 conducts the control process so that the bending section 27 is bent to the target position corresponding to the instructed value of the articulation operation. When the distal end section 24 contacts the inner wall in the body cavity or the like in a pressure equal to or larger than a set value, the control is conducted to suppress the bending any further.

Thus, when the user inserts the insert section 21 in the body cavity, even when the articulation operation is performed to insert along the bending duct line, the contact in a pressure equal to or larger than a set value can be avoided, so the pain on the patient can be abbreviated and the smooth insertion can be enabled.

It should be noted that on the basis of the detection output of the contact sensor 142, the control may be performed to change the consistency through the consistency varying actuator.

The other operation and the effect in the second embodiment are almost the same as those in the first embodiment.

Next, a third embodiment of the present invention will be described.

Figure 30:
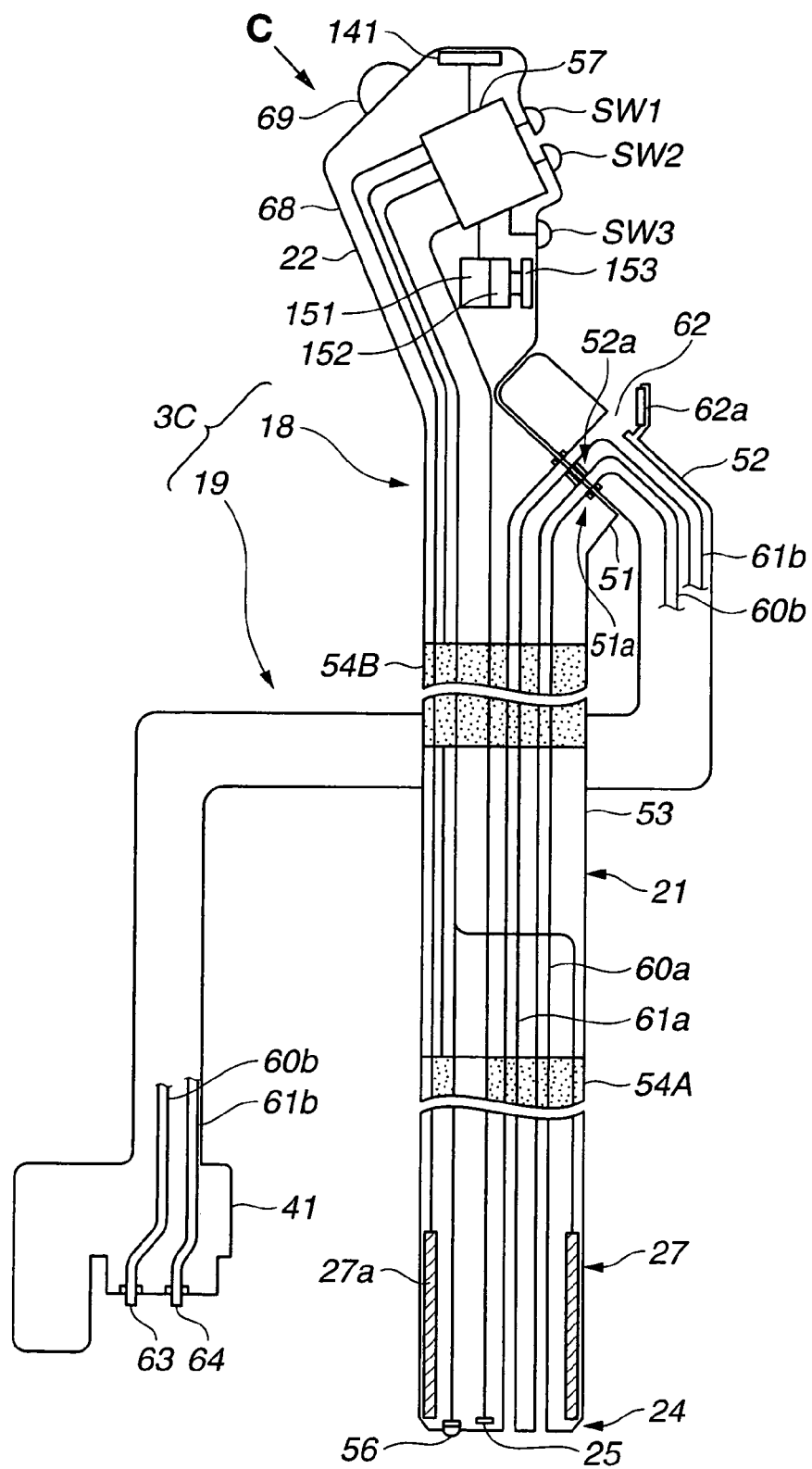
FIG. 30 is a side view with a see-through of a part of internal components of the endoscope in the endoscopic system according to a third embodiment of the present invention.

FIG. 30 is a side view with a see-through of a part of internal components of the endoscope in the endoscopic system according to the third embodiment of the present invention.

As shown in FIG. 30, the endoscope 3C of the third embodiment does not have the signal line 71b as in the second embodiment, but instead has the antenna section 141 to perform signal data transmission and reception through the antenna section 141. Without the provision of the power supply line 71a, the endoscope 3C further includes a battery 151, a charging circuit 152 connected to the battery, and a noncontact charging coil 153 in the operation section 22.

The connector section 51 in the operation section 22 of the third embodiment includes the duct line connector section 51a having the air water connector and the suction connector.

For this reason, the tube unit 19 detachably connected to the endoscope main body 18 of the third embodiment does not have the power supply line 73a and the signal line 73b as in the first embodiment, but has a structure in which the air water duct line 60b and the suction duct line 61b are inserted.

The battery 151 is composed of a secondary battery which is rechargeable such as a lithium battery, and the battery 151 is connected via the charging circuit 152 to the water tight noncontact charging coil 153 built in the vicinity of the outer surface of the operation section 22. Then, a facing noncontact power feed coil not shown in arranged on the outer surface at a part where the noncontact charging coil 153 is built in. By supplying the noncontact power feed coil with an alternating current, the battery 151 can be charged.

That is, by supplying the noncontact power feed coil arranged on the outer surface side of the operation section 22 with the alternating electric power, the alternating electric power can be transmitted to the noncontact charging coil 153 inside the operation section 22 through electromagnetic coupling. The alternating electric power is then converted by the charging circuit 152 into a direct current voltage for charging the battery 151 to be supplied to the battery 151, whereby the battery 151 is charged.

According to the third embodiment, as has been described in the first embodiment, the LED 56 is adopted as the illumination section, so the consumed electric power can be reduced significantly as compared to the case of using a lamp. Also, the ultrahigh sensitive CCD 25 (having the gain varying function) is adopted as the image pickup element, a sufficiently bright image can be obtained even when the illumination light quantity is small. For this reason, even when the battery 151 is adopted, the endoscope inspection can be performed for much longer time as compared with the conventional example. In addition, the battery 151 can adopt a small and light battery as compared with the conventional example, and therefore the operation section 22 is lightened to ensure the satisfactory operability.

The electric system structure inside the endoscope 3C of the third embodiment has a structure in which the contact sensor 142, the transparency sensor 143, and the like are removed in FIG. 29. The power supply transmission and reception section 97 has a structure including the battery 151, the charging circuit 152 connected to the battery, and a noncontact charging coil instead, so a drawing thereof will be omitted.

According to the third embodiment, the tube unit 19 is composed of only the duct line system, which is the structure suited to the disposal use. Also, in the case of recycle (reuse), no power line is arranged inside the tube unit 19, so the recycle is facilitated. In addition, according to the third embodiment, when the duct line system is not used, the endoscope can be used while the tube unit 19 is removed from the endoscope main body 18. In other words, in this case, the tube unit 19 is unnecessary, so the operation disturbance by the tube unit 19 can be eliminated, thereby improving the operability.

The other operations and effects are almost the same as those in the case described in the first embodiment or the second embodiment.

Next, a fourth embodiment of the present invention will be described.

Figure 31:
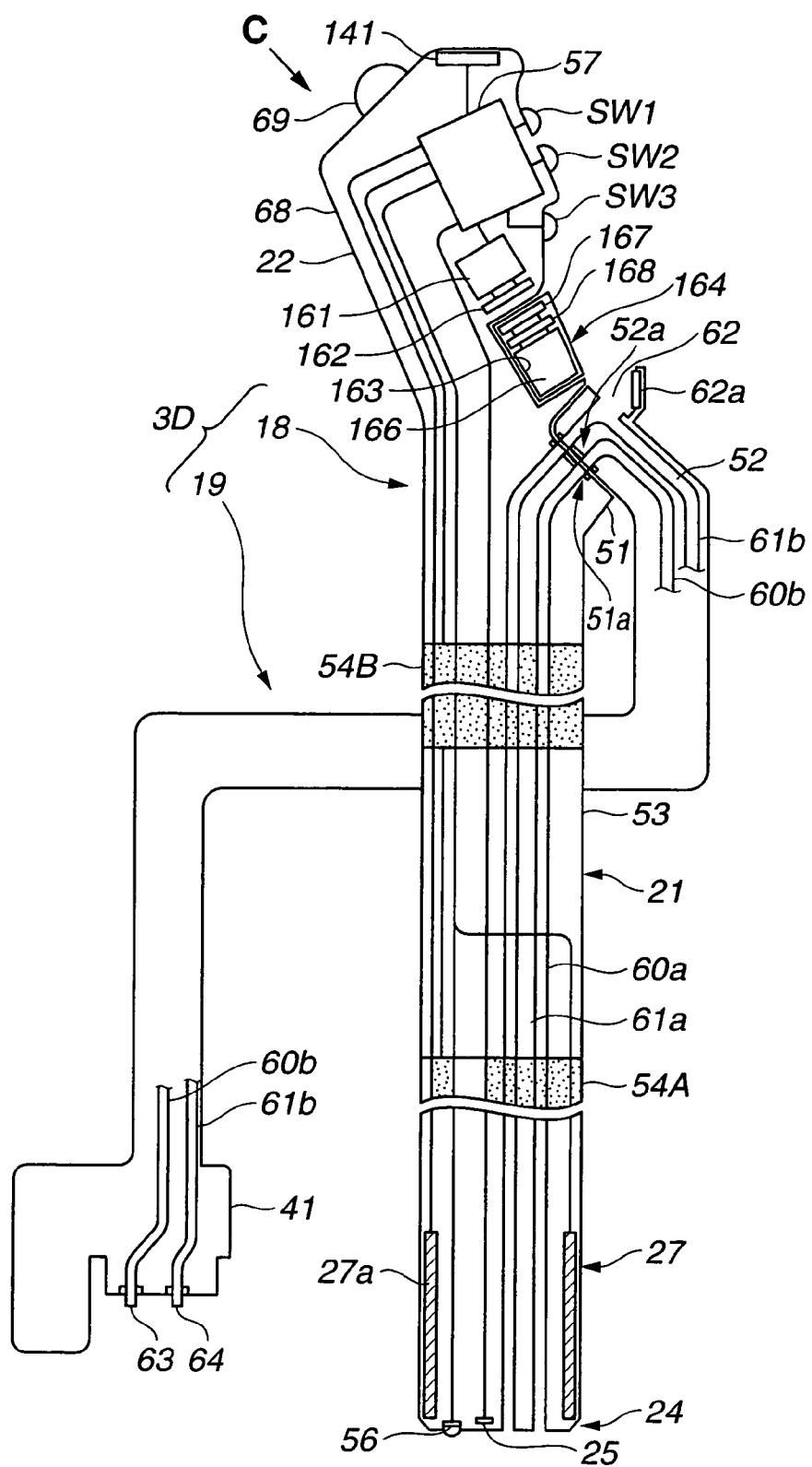
FIG. 31 is a side view with a see-through of a part of internal components of the endoscope in the endoscopic system according to a fourth embodiment of the present invention.
Figure 32A:
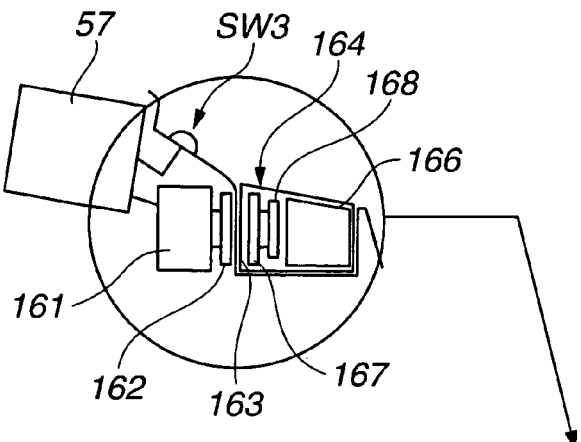
FIG. 32A is a main part side view showing a battery unit and a peripheral section of the endoscope in the endoscopic system according to the fourth embodiment.
Figure 32B:
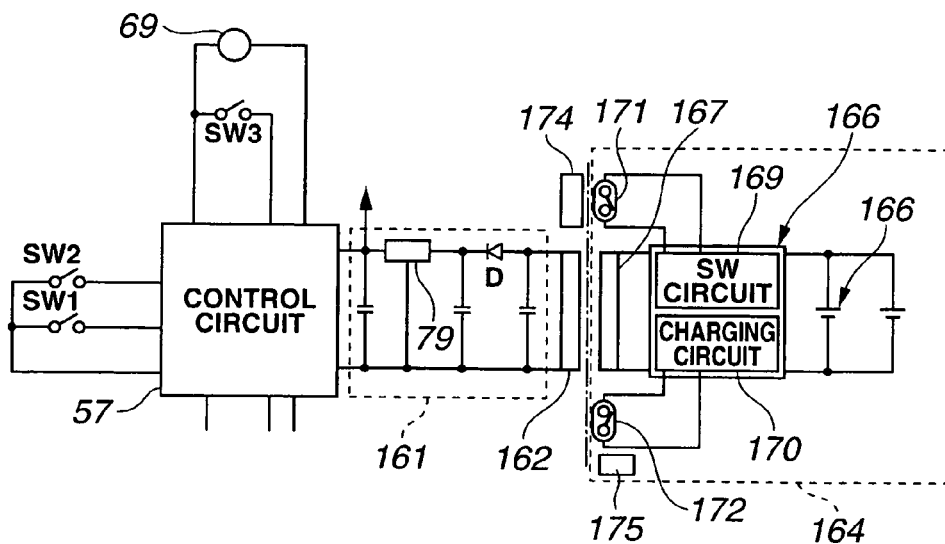
FIG. 32B is an electric circuit view showing a structure of the battery unit and its peripheral section of the endoscope in the endoscopic system according to the fourth embodiment of the present invention.
Figure 32C:
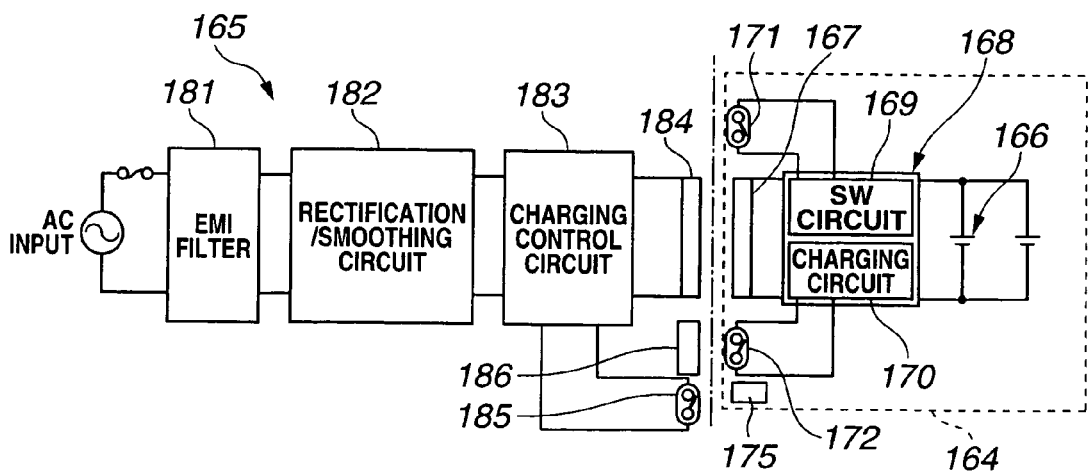
FIG. 32C is an electric circuit view showing a structure of a charging section relating to the battery unit of the endoscope in the endoscopic system according to the fourth embodiment.

FIG. 31 is a side view with a see-through of a part of internal components of the endoscope in the endoscopic system according to the fourth embodiment of the present invention. FIGS. 32A to 32C are main part side view showing a battery unit and a peripheral section of the endoscope in the endoscopic system, and electric circuit views showing an electric circuit and a charging section of the battery unit of the endoscope in the endoscopic system according to the fourth embodiment.

As shown in FIG. 31, the endoscope 3D of the fourth embodiment has a power supply circuit 161 instead of the battery 151 built in the operation section 22 and the charging circuit 152 in the endoscope 3C of the third embodiment. Also, such a structure is provided in which the noncontact power feed coil 162 is connected to the power supply circuit 161, a concave section 163 is formed at a position opposing the part where the noncontact power feed coil 162 is built in the operation section 22, and a noncontact battery unit 164 can be detachably mounted to the concave section 163.

FIG. 32A is an enlarged view in the vicinity of the battery unit 164, FIG. 32B shows an internal structure of FIG. 32A, and FIG. 32C shows a circuit configuration in which the battery unit 164 is connected to a charging device 165, the charging device 165 charges a battery 166.

As shown in FIG. 32A, inside the battery unit 164 having the water tight outer case, which is mounted to the concave section 163 provided to the operation section 22, at a position opposing the noncontact power feed coil 162 on the power supply circuit 161 side, the noncontact power feed coil 167 is arranged. The noncontact power feed coil 167 is connected to the battery 166 via a power supply circuit 168.

As shown in FIG. 32B, the noncontact power feed coil 167 is connected to a switching circuit 169 and a charging circuit 170 which structure the power supply circuit 168, and the switching circuit 169 and the charging circuit 170 are respectively connected to reed switches 171 and 172 which function as magnetic sensitive switches to turn ON/OFF in response to magnetic force (magnetic field). The battery unit 164 is accommodated in the outer case to have the water tight structure.

The power supply circuit 161 connected to the other noncontact power feed coil 162 has the same structure as that shown in, for example, FIG. 12. The alternating electric power transmitted to the noncontact power feed coil 162 is rectified by a rectifying diode D and smoothed while the pulsating flow component is removed after passing through the smoothing capacitor. Then, the power is input to a three-terminal power supply IC 79, and is converted into a predetermined voltage value by the three-terminal power supply IC 79.

The direct current electric power of a predetermined voltage value generated by the power supply circuit 161 is supplied to the respective sections in the control circuit 57.

Also, a magnet 174 is arranged at a position in the vicinity of the reed switch 171 in the operation section 22. As shown in FIG. 32A, when the battery unit 164 is attached to the concave section 163, the reed switch 171 is turned ON with use of the magnetic power of the magnet 174.

Meanwhile, the magnet 175 is arranged on the other reed switch 172 side. The magnetic power of the magnet 175 does not affect the reed switch 172, and causes the magnetic flux to face the side of the reed switch 172. Thus, the reed switch 172 is turned OFF (the magnet 175 is used to control, as shown in FIG. 32C, the charging device 165 side).

Therefore, the electric power of the battery 166 is supplied to the switching circuit 169. The switching circuit 169 performs the switching operation. A pulse current (alternating current) subjected to the switching by this switching operation is transmitted via the noncontact power feed coil 167 to the noncontact power feed coil 162 side where noncontact electromagnetic coupling is caused with the noncontact power feed coil 167.

Then, with the power supply circuit 161 connected to the noncontact power feed coil 162, a direct current power of a predetermined value is generated.

The charging device 165 has a circuit configuration of FIG. 32C to charge the battery 166 of the battery unit 164.

The alternating electric power from the AC power supply passes through an EMI filter 181 and is input to a rectifying/smoothing circuit 182 to be converted into a smoothed direct current electric power. After that the power is supplied to a charge control circuit 183 for performing switching operations and the like to perform charge control almost in the same manner as the switching circuit 169. The noncontact power feed coil 184 is connected to an output terminal of the charge control circuit 183, and the alternating electric power switched by the charge control circuit 183 is supplied via the noncontact power feed coil 184 to the noncontact power feed coil 167 side.

In addition, a reed switch 185 is connected to the charge control circuit 183. By mounting the battery unit 164 to the concave section of the charging device 165, the reed switch 185 is turned ON in response to the magnetic power from the magnet 175 provided on the battery unit 164 side. With a magnet 186 provided on the charging device 165, the reed switch 172 connected to the charging circuit 170 can be turned ON.

Thus, in this case, the charge control circuit 183 is in an operating status. Through the switching operation, the alternating electric power is supplied from the noncontact power feed coil 184 to the noncontact power feed coil 167 side. The alternating electric power supplied to the noncontact power feed coil 167 side is converted by the charging circuit 170 into a direct current voltage for charging the battery 166 to thereby charge the battery 166.

Also, while the charge control circuit 183 monitors a current or the like supplied from the noncontact power feed coil 184 to the noncontact power feed coil 167 side, the charge status of the battery 166 is detected on the basis of the current value. When a predetermined charge status is reached, the alternating electric power supplied is stopped to notify about the charge completion by turning on an LED or the like which is not shown in the drawing.

In this manner, according to the fourth embodiment, by mounting the detachable battery unit 164 to the endoscope main body 18, the collective control operation can be operated through the control circuit 57 provided inside the operation section 22.

When the electric energy of the battery 166 is exhausted or low in the battery unit 164, as shown in FIG. 32C, by mounting the battery unit 164 to the charging device 165 in a noncontact way, the battery 166 can be charged.

According to this embodiment, it is unnecessary to insert the electric signal lines through the tube unit 19, the tube unit 19 can be obtained in further low costs and realized to be more suitable to the disposal application. In addition, the reduction in diameter of the tube unit 19 itself can be achieved, thereby improving the operability in operating the operation section 22.

Also, according to this embodiment, in the case where the air water operation and the suction operation are not required, as has been described in the third embodiment too, the endoscope can be used even when the tube unit 19 side can be removed from the endoscope main body 18.

It should be noted that embodiments and the like which are structured by combining parts of the above-mentioned embodiments are within the scope of the present invention. Furthermore, modified examples obtained by modifying the above embodiments are also within the scope of the present invention. For example, a deformed structure in which a connection section of the tube unit 19 is shifted to the base end (rear end) side of the insert section 21 than the grasping section 68 or the operation section 22 side is basically within the scope of the present invention.

Subsequently, a fifth embodiment of the present invention will be described.

Figure 33:
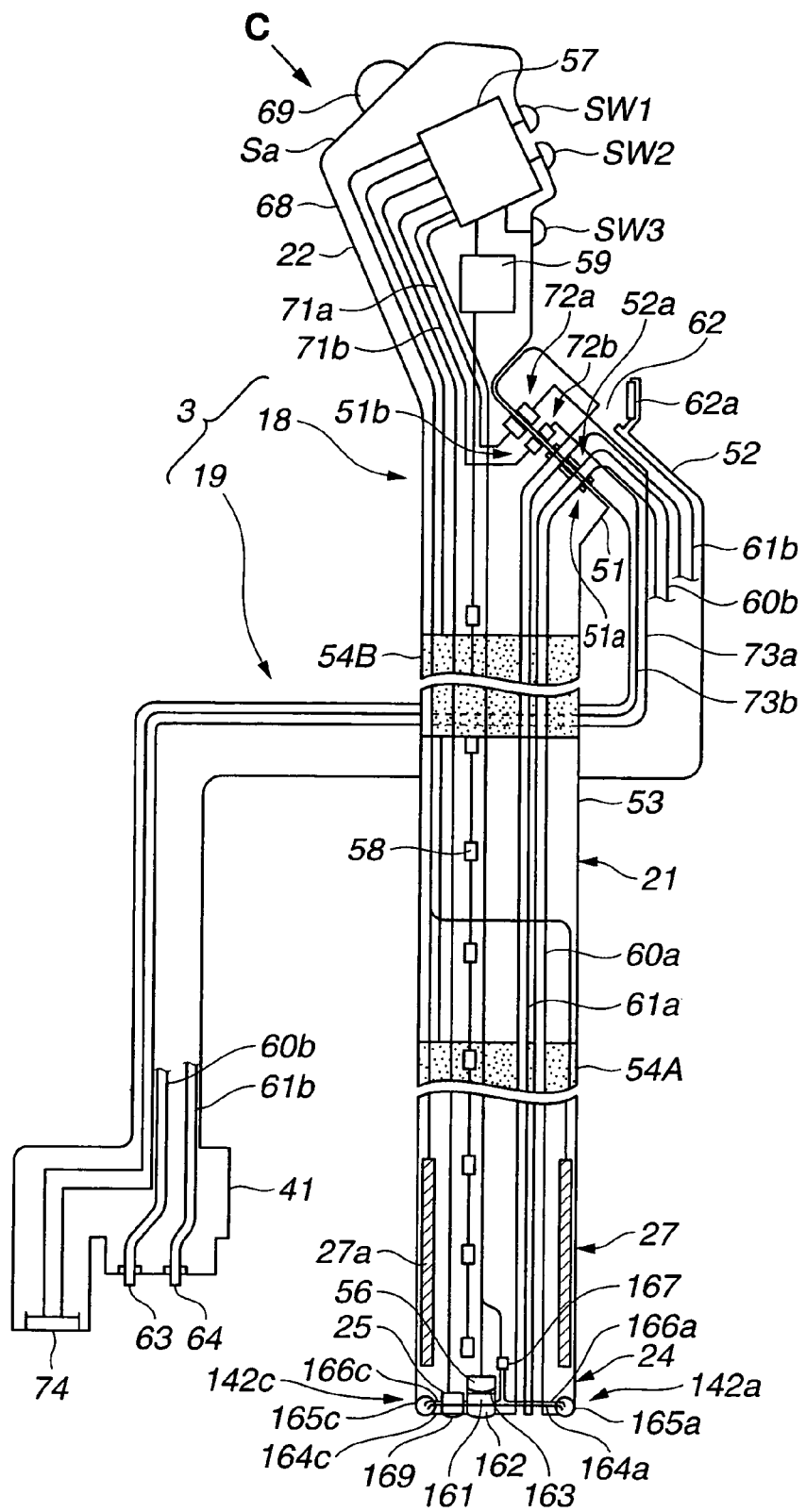
FIG. 33 is a side view with a see-through of a part of internal components of the endoscope in the endoscopic system according to a fifth embodiment of the present invention.
Figure 34:
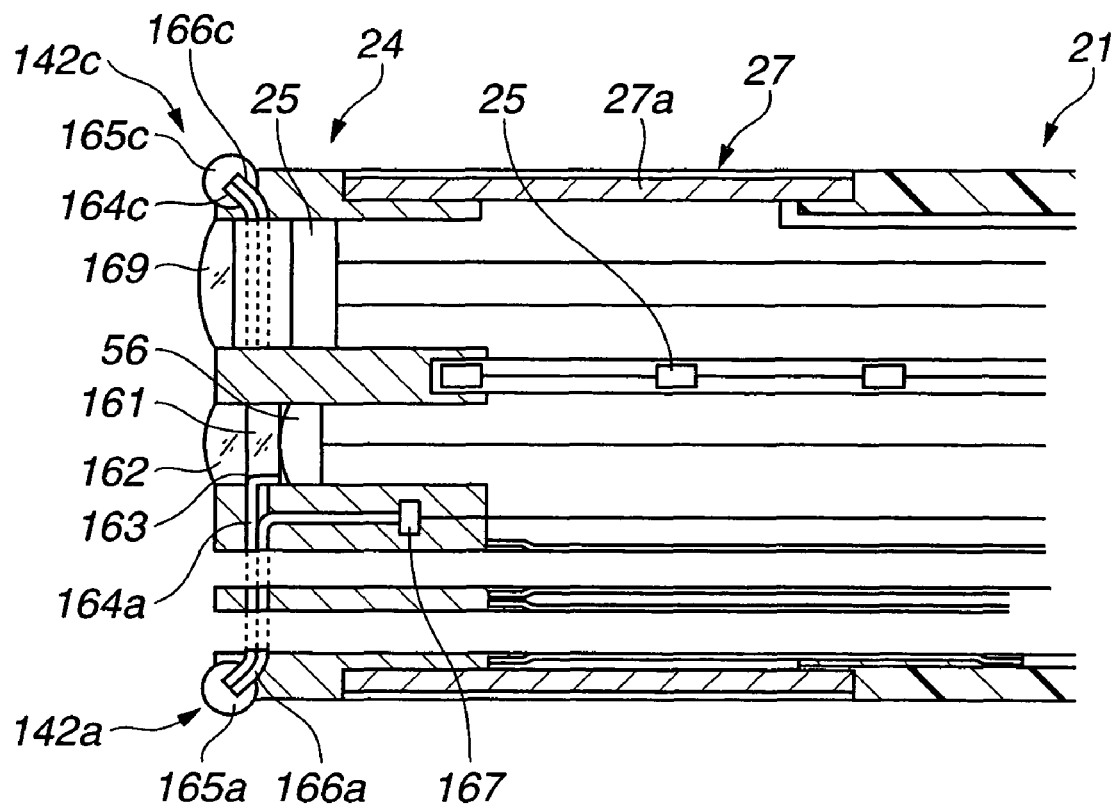
FIG. 34 is a main part enlarged cross-sectional view showing a structure of the endoscope on a distal end side of an insert section in the endoscopic system according to the fifth embodiment.
Figure 35A:
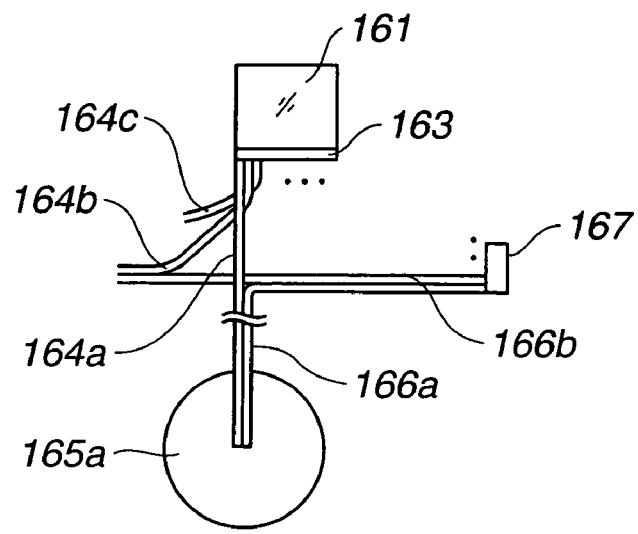
FIG. 35A shows a schematic structure of an optical pressure amount detection section of the endoscope in the endoscopic system according to the fifth embodiment.
Figure 35B:
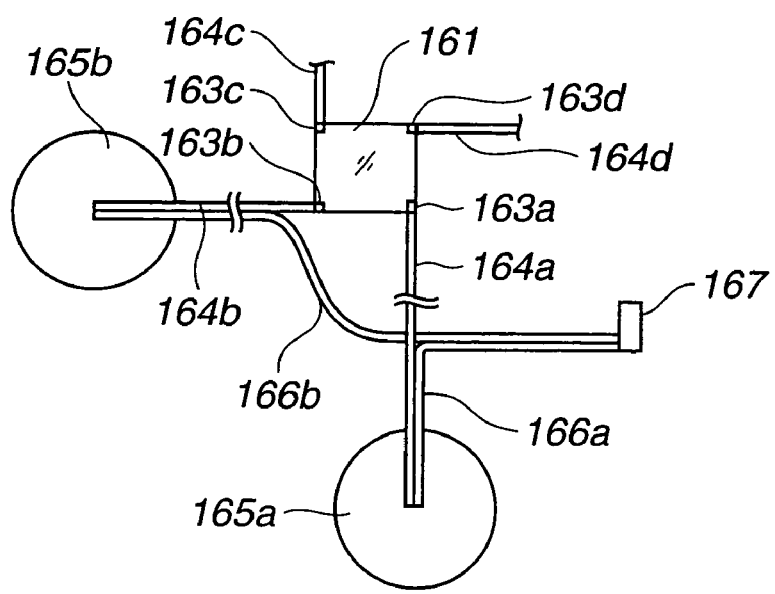
FIG. 35B shows a schematic structure of the optical pressure amount detection section of the endoscope in the endoscopic system according to the fifth embodiment.
Figure 36:
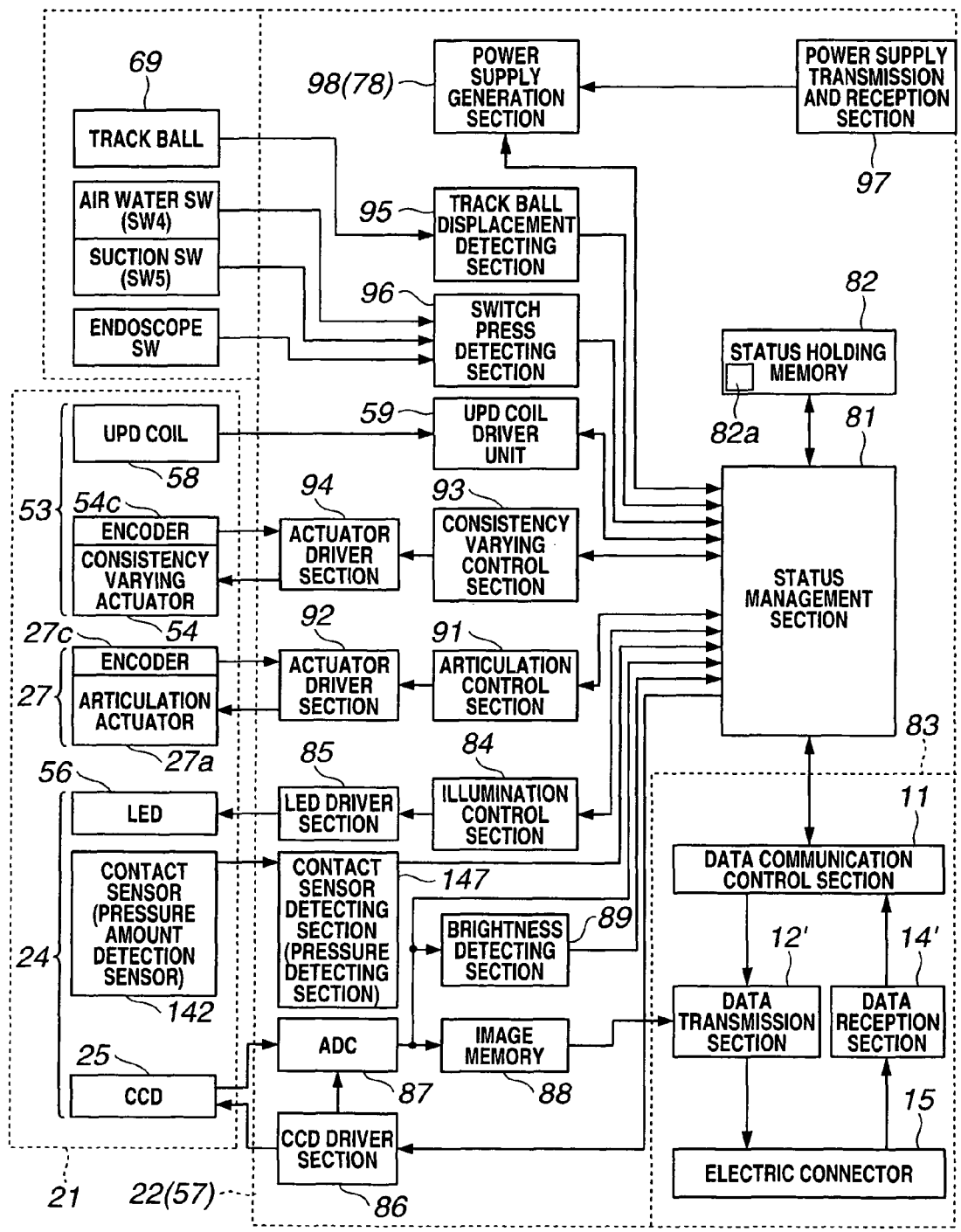
FIG. 36 is a block diagram showing an electric structure of the endoscope in the endoscopic system according to the fifth embodiment.
Figure 37:
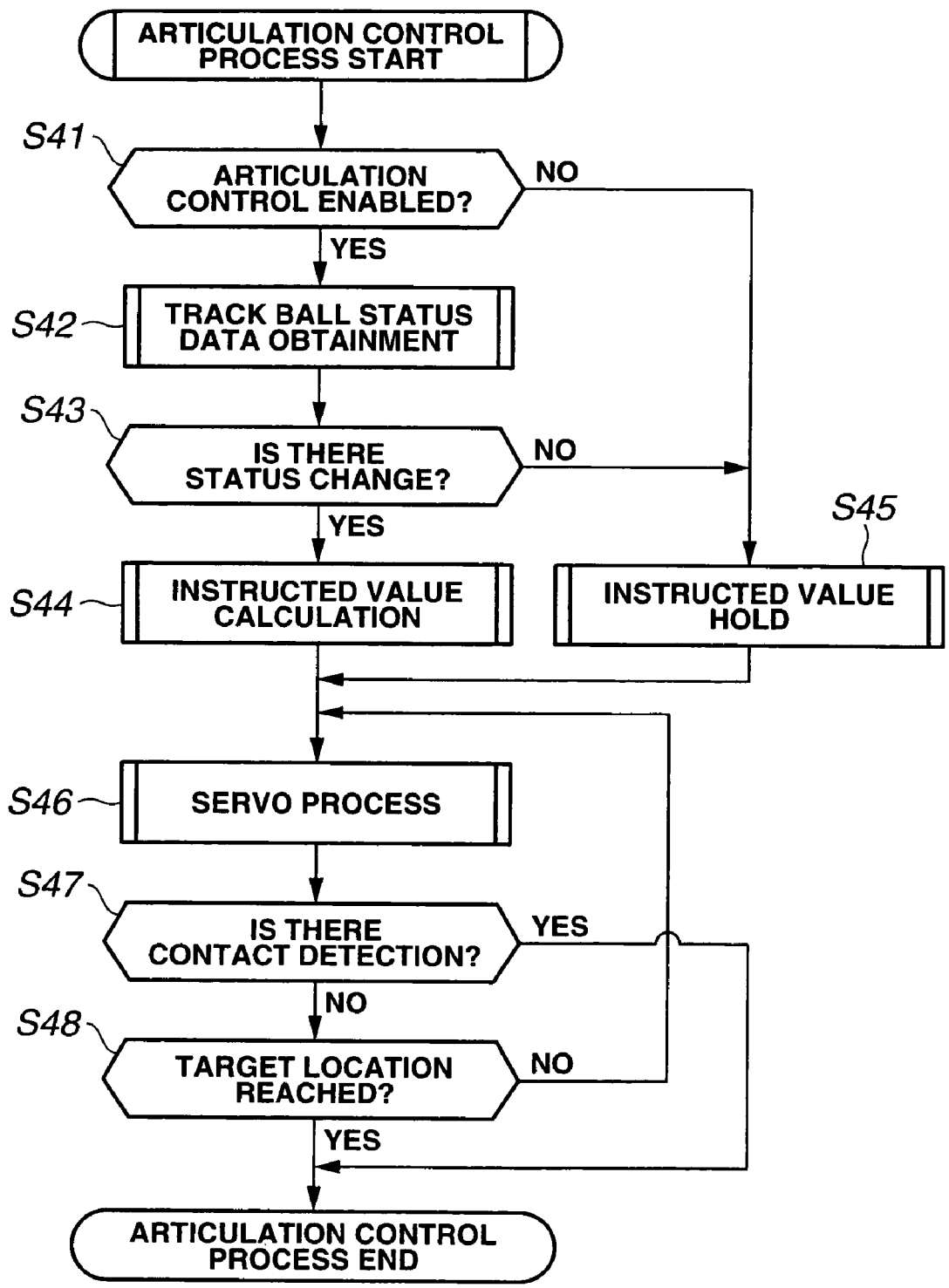
FIG. 37 is a flowchart showing a control process of an articulation operation of the endoscope in the endoscopic system according to the fifth embodiment.

FIG. 33 is a side view with a see-through of a part of internal components of the endoscope in the endoscopic system according to the fifth embodiment of the present invention. FIG. 34 is a main part enlarged view showing a structure of the endoscope on a distal end side of an insert section in the endoscopic system according to the fifth embodiment. FIGS. 35A and 35B show a schematic structure of an optical pressure amount detection section of the endoscope in the endoscopic system according to a fifth embodiment. FIG. 36 is a block diagram showing an electric structure of the endoscope in the endoscopic system according to a fifth embodiment. FIG. 37 is a flowchart showing a control process of an articulation operation of the endoscope in the endoscopic system according to a fifth embodiment.

The endoscope of the fifth embodiment has the fundamental structure which is basically the same as that of the first embodiment, so only difference will be described, and in the drawings, the same compositions have the same reference numerals while omitting a description.

As shown in FIG. 33 and FIG. 34, in the endoscope 3 of the fifth embodiment, the light emitting diode (abbreviated as LED) 56 is arranged as the illumination section on an inner side of the illumination window provided to the distal end section 24 of the insert section 21. The illumination light of the LED 56 is output forward via a lens integrally attached to the LED 56. In front of this lens, a transparent optical element 161 is arranged. Through the optical element 161 and an illumination lens 162 arranged in front thereof, the illumination light is output forward to illuminate a subject of a patient or the like.

According to the fifth embodiment, a light branch section 163 is formed in a peripheral section of the optical element 161. FIG. 35A is a schematic diagram of the optical element 161 as seen from the LED 56 side. That is, a prism or a beam splitter which has a function of splitting the light into transmission light and reflection light is formed in the peripheral section of the optical element 161, thereby forming the light branch section 163.

Then, one ends of optical fibers 164a, 164b, 164c, and 164d are arranged as light guide members on a side face functioning as a path for the reflection light due to the light branch section 163, and the other ends of the optical fibers 164a, 164b, 164c, and 164d are fixed into, for example, pressure deformation members 165a, 165b, 165c, and 165d provided to corners of up, down, left, and right of the distal end surface of the distal end section 24 (not all of which are shown in the drawing).

The pressure deformation members 165$i$ (i=a to d) have, for example, substantially spherical to be deformed in accordance with the pressure amount, and is made of urethane or the like having an appropriate reflection characteristic. Also, one end of other optical fibers 166$i$ that each form a pair with the optical fibers 164$i$ is fixed in the pressure deformation members 165$i$ (i=a to d), and the other end of the optical fibers 166$i$ is arranged at a position opposing the light detection device element that detects light and structures a light detection device array 167 (it should be noted that in the drawing, only the light detection device array 167 is shown).

When the pressure deformation members 165$i$ are pressed and deformed, the reflection characteristic of the like guided by the optical fibers 164$i$ in the pressure deformation members 165$i$ changes to change the quantity of light input to the optical fibers 166$i$. Therefore, when the pressure deformation members 165$i$ are pressed and deformed, the electric signal intensity (signal level) detected by the light detection device of the light detection device array 167 via the optical fibers 166$i$ also changes. It should be noted that the light detection device array 167 is connected via the signal line to the control circuit 57.

Then, the control circuit 57 judges whether or not on the basis of the output from the light detection device array 167, a pressure equal to or larger than a predetermined value is effected depending on whether or not the output change amount changes by the amount equal to or larger than a predetermined value. In the case of driving and bending the bending section 27, when it is judged that the output change amount changes by the amount equal to or larger than a predetermined value, a regulation section for regulating the bending drive is formed. It should be noted that this operation will be described in detail.

It should be noted that in FIG. 35A, the light branch section 163 is formed to be elongated on the lower side of the optical element 161, but the light branch section 163a, 163b, 163c, and 163d may be formed, as shown in FIG. 35B, at four corners of the optical element 161. As a result, light guide to the pressure deformation members 165$i$ arranged at the respective positions of up, down, left, and right in the bending section 27 is facilitated.

Then, in the case of the structure of FIG. 35B, only a part of the periphery side of the illumination light is used, so the illumination light for illuminating the subject side is hardly reduced, and the pressure amount detection can be conducted.

In this manner, a pressure detection section in which a part of light in the illumination light is used to optically detect the pressure amount on the respective corners of up, down, left, and right in the distal end section 24 (in FIG. 15, the contact sensor 142 for simplification) is formed.

It should be noted that the LED 56 may be an LED for emitting white light or R-LED, G-LED, or B-LED for emitting light in the wavelength of red (R), green (G), or blue (B). The light emitting element forming the illumination section is not limited to the LED 56, and may also be formed by using a LD(laser diode) or the like.

An objective lens 169 is attached to the observation window provided so as to be adjacent to the illumination window. The CCD 25 having the gain varying function is arranged at an image forming position of the objective lens, forming an image pickup section for capturing a subject. The CCD 25 according to embodiment has the gain varying function in the CCD element itself. With the gain varying function, the CCD output signal gain can be easily varied up to several hundred fold. Thus, under the illumination light by the LED 56, it is possible to obtain a bright image with low S/N reduction. Also, the LED 56 is efficient in light emitting as compared with the case of lamp, thereby suppressing temperature increase in the vicinity of the LED 56.

The ends of the signal lines inserted through the insert section 21 are respectively connected to the LED 56 and the CCD 25, and the other ends of the signal lines inserted through are connected, for example, to the control circuit 57 that is provided inside the operation section 22 and performs the central control process (concentrated control process). In addition, a plurality of the UPD coils 58 are arranged inside the insert section 21 along the longitudinal direction thereof at a predetermined interval. The signal lines connected to the respective UPD coils 58 are connected to the control circuit 57 via a UPD coil driver unit 59 provided inside the operation section 22.

Also, as shown in FIG. 36, the status management section 81 controls, via the illumination control section 84 for controlling the illumination, the LED driver section 85 that is controlled by the illumination control section 84. The LED driver section 85 applies the LED 56 with an LED driver signal for causing the LED 56 functioning as the illumination section to emit light.

With the light emission from the LED 56, the illuminated subject of the patient or the like is image-formed on the image forming surface of the CCD 25 provided at the image forming position by the objective lens 169 attached to the observation window and is photoelectrically converted by the CCD 25.

The CCD 25 outputs a signal charge accumulated through the photoelectrical conversion as an image pickup signal, in response to the application of the CCD driver signal from the CCD driver section 86 controlled by the status management section 81. The image pickup signal is converted by the A/D converter 87 from an analog signal to a digital signal, and thereafter input to the status management section 81. At the same time the digital signal (the image data) is stored in the image memory 88. The image data of the image memory 88 is sent to the data transmission section 12' of the transmission and reception unit 83.

Then, the data is transmitted from the electric connector 15 via the signal line 73b inside the tube unit 19 to the AWS unit 4 side. Furthermore, the data is wirelessly transmitted from the AWS unit 4 to the endoscopic system control device 5.

The output signal of the ADC 87 is sent to the brightness detection section 89, and the image brightness information detected by the brightness detection section 89 is sent to the status management section 81. The status management section 81 performs light adjustment control on the basis of this information via the illumination control section 84, so that the illumination light quantity of the LED 56 becomes an appropriate brightness.

It should be noted that as will be described below, when an operation for performing optical pressure amount detection, the light adjustment control keeps the illumination light quantity of the LED 56 constant to obtain an image of an appropriate brightness through the gain varying of the CCD 25.

As described above, in this embodiment, the contact sensor 142 is provided on the outer surface of the distal end section 24. The contact sensor 142 is connected via a contact detection section (press detection section) 147 for performing contact detection (press detection) on the basis of the detection output to the status management section 81.

When the status management section 81 performs the articulation operation, on the basis of the detection result from the contact sensor 142 at that time, the control for regulating the bending of the bending section 27. With this control, the bending section 27 does not apply unnecessary force to the inner wall of the body cavity for pain relief For example, when the insert section 21 is inserted in the body cavity, smooth insertion can be conducted while reducing the pain to the patient.

In addition, the status management section 81 controls the actuator driver section 92 via the articulation control section 91 to manage the drive of the articulation actuator (EPAM) 27a by the actuator driver section 92. It should be noted that the drive amount of the articulation actuator (EPAM) 27a is detected by the encoder 27c, and the control is performed so that the drive amount matches the instructed value.

Next, the effect of the endoscope having such a structure of the fifth embodiment will be described.

In this embodiment as will be described below, the output of the optical press amount detection section is used for the articulation operation to enable smooth inserting operations for the insert section 21 and the like.

Now, with reference to FIG. 37, the articulation operation control process will be described.

When the articulation control process is started, similarly to the first embodiment, as shown in Step S41, the status management section 81 judges whether or not the articulation control is enabled.

According to this embodiment, regarding the track ball 69, the status management section 81 judges whether or not the articulation control is enabled as shown in Step S41 on the basis of whether or not the track ball 69 is pressed. To be specific, the status management section 81 can detect the displacement operation and the press operation of the track ball 69 on the basis of the output of the track ball displacement detecting section 95. It should be noted that when the track ball 69 is pressed, the articulation control is turned OFF.

The status management section 81 judges whether or not the articulation control is enabled on the basis of the output of the track ball displacement detecting section 95.

Then, when it is judged that the articulation control is not enabled, the flow shifts to Step S45, where the previous instructed value is held. On the other hand, when it is judged that the articulation control is enabled, the flow proceeds to the next Step S42, where the status management section 81 obtains the status data based on the operation of the track ball 69. Then, in the next Step S43, the status management section 81 judges whether or not there is a status change on the basis of the output of the track ball displacement detecting section 95.

In this case, regarding the status management section 81, when it is judged that there is no status change, the flow shifts to Step S45. On the other hand, when it is judged that there is a status change, in the next Step S44, an instructed value corresponding to the rotation direction and the rotation amount of the track ball 69 is calculated.

After the process in Step S44 or S45, as shown in Step S46, the status management section 81 sends the instructed value to the actuator driver section 92 via the articulation control section 91 to perform the servo process on the articulation actuator 27a.

That is, the actuator driver section 92 drives the articulation actuator so that an articulation angle state (bending angle) corresponding to the instructed value is obtained on the basis of the instructed value.

Also, during the start of the servo process in Step S46, the status management section 81 takes in the detection result of the contact sensor 142 via the contact sensor detection section 147 as shown in Step S47 to detect (judge) whether or not the distal end section 24 contacts the inner wall or the like in the body cavity with a pressure equal to or larger than the appropriate value.

Then, when it is judged that the contact is not performed with a pressure equal to or larger than the appropriate value, the flow proceeds to the next Step S48, where the status management section 81 judges whether or not the target position corresponding to the instructed value for the articulation is reached on the basis of the detection value of the encoder 27c. When the target position is not reached, the flow returns to Step S46. On the other hand, when the target position is reached, the control process for the articulation operation is ended.

On the other hand, in Step S47, when it is judged that the contact is performed with a pressure equal to or larger than the appropriate value, the process in the next Step S48 is not performed, and the status management section 81 ends the control process for the articulation operation.

In this way, when the articulation operation is performed, the status management section 81 conducts the control process so that the bending section 27 is bend to the target position corresponding to the instructed value by the articulation operation. When the contact on the inner wall or the like in the body cavity has a pressure equal to or larger than the value set by the distal end section 24, the control is performed so that the bending is suppressed for further bending.

Therefore, when the user inserts the insert section 21 into the body cavity, even when the articulation operation is performed to insert the insert section along the bending duct line, it is possible to avoid the contact with a pressure equal to or larger than the set value, whereby the pain to the patient can be reduced, and also the smooth insertion can be realized.

With the endoscope 3 according to this embodiment which forms the endoscopic system 1 for performing such an operation, as the pressure amount detection (contact amount) is structured using a part of light on the periphery side of the illumination light output from the illumination window, the smooth insertion operations and the like can be performed while efficiently using the illumination light.

Next, a sixth embodiment of the present invention will be described.

Figure 38:
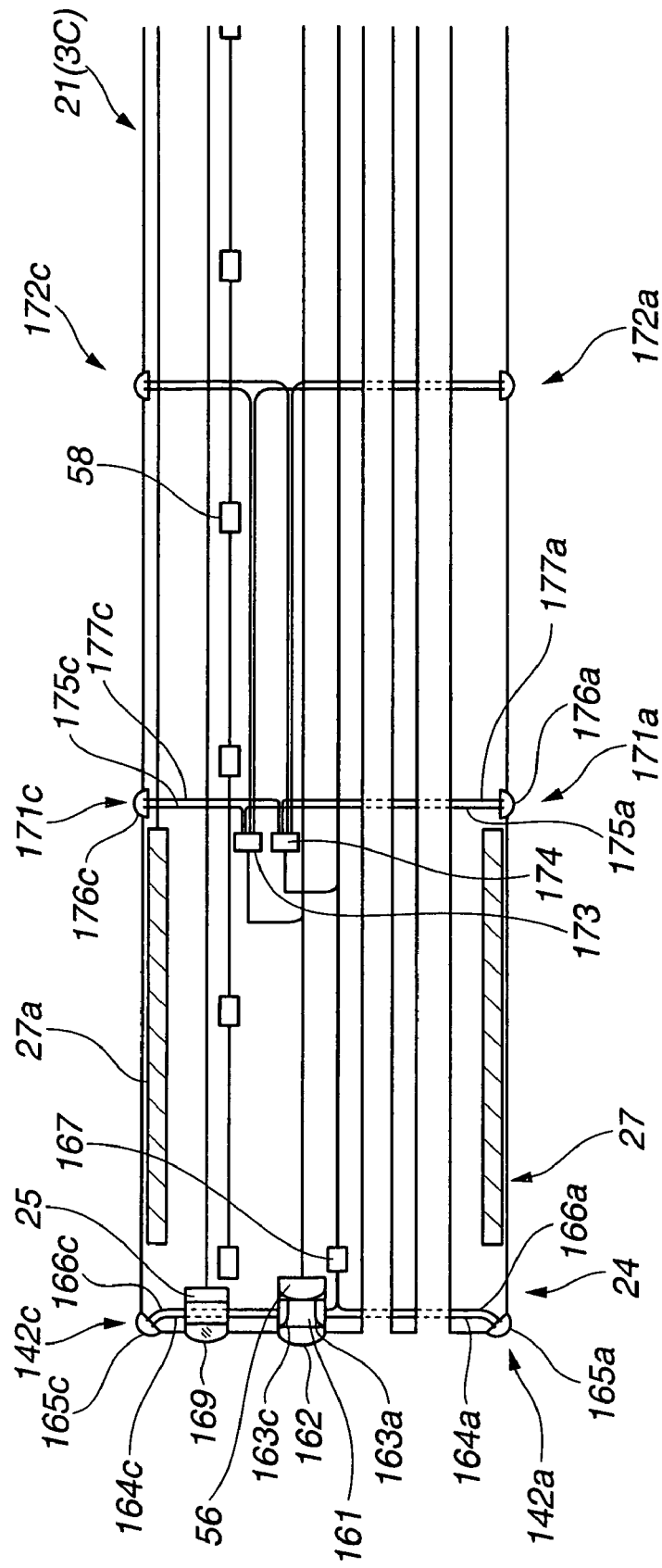
FIG. 38 is a main part enlarged cross-sectional view showing a structure of the endoscope on a distal end side of an insert section in the endoscopic system according to a sixth embodiment of the present invention.
Figure 39:
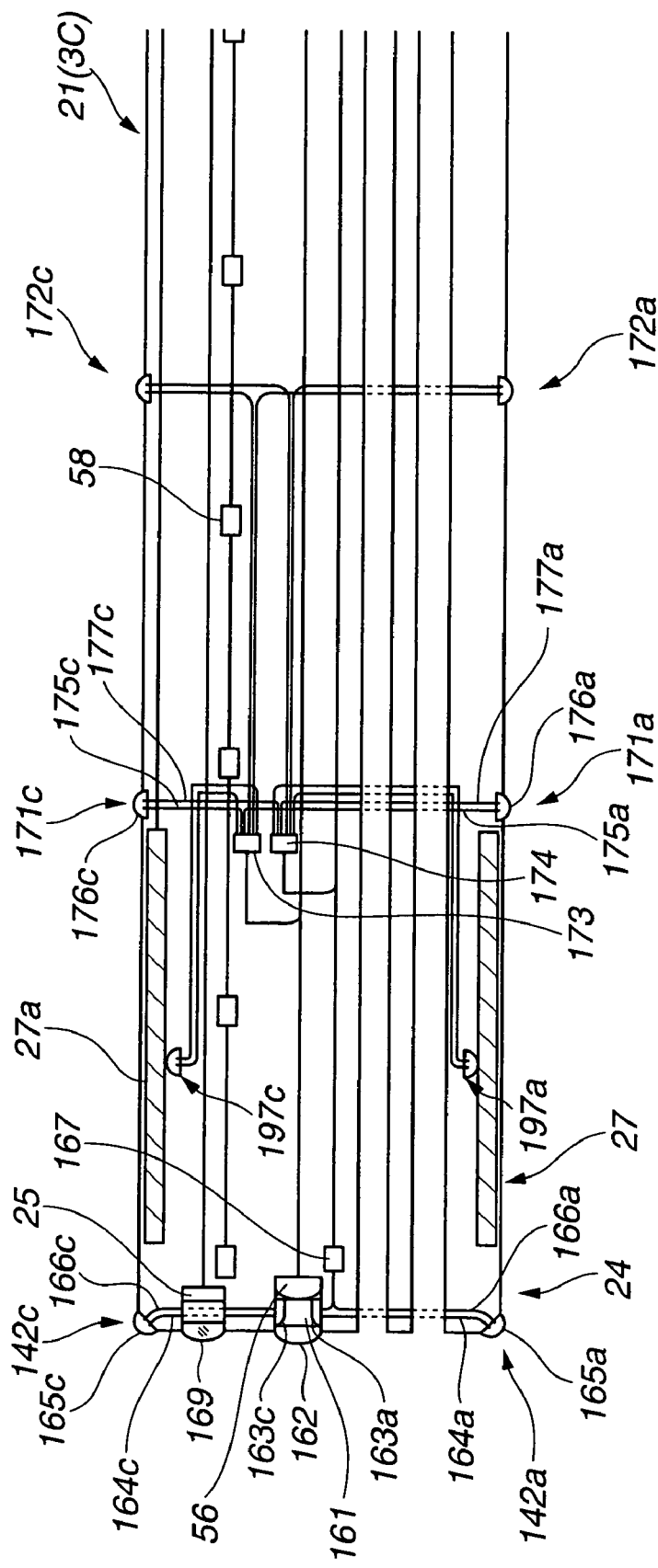
FIG. 39 is a main part enlarged cross-sectional view showing a structure of the endoscope on a distal end side of the insert section in the endoscopic system according to a first modified example of the sixth embodiment.
Figure 40:
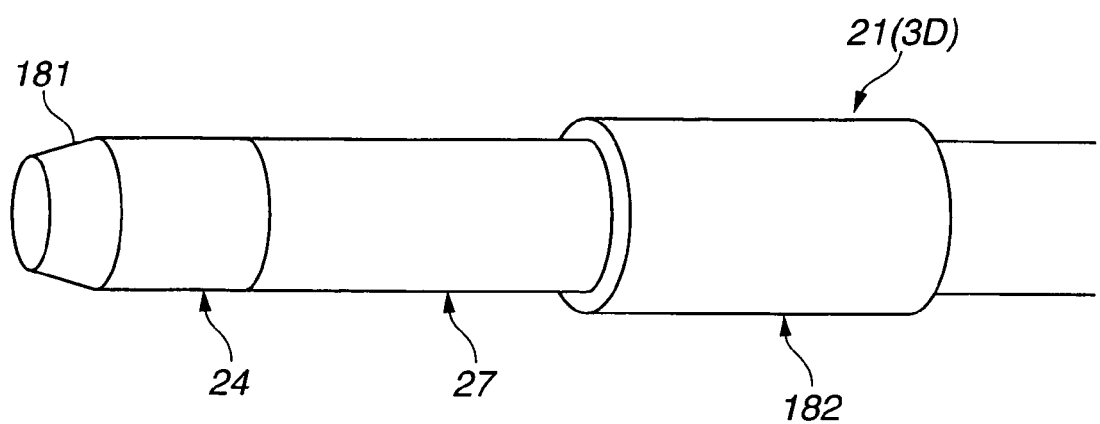
FIG. 40 is a main part enlarged perspective view showing a structure of the endoscope on a distal end side of the insert section in the endoscopic system according to a second modified example of the sixth embodiment.
Figure 41:
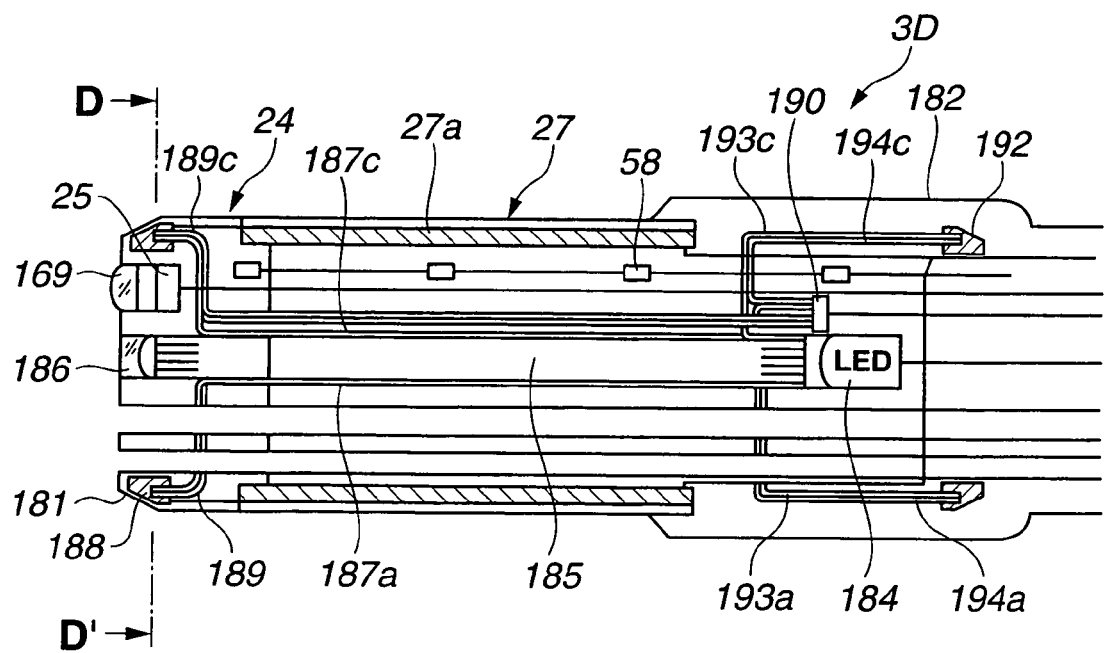
FIG. 41 is a main part enlarged cross-sectional view showing the structure of the endoscope on the distal end side of the insert section in the endoscopic system according to the second modified example of the sixth embodiment.
Figure 42A:
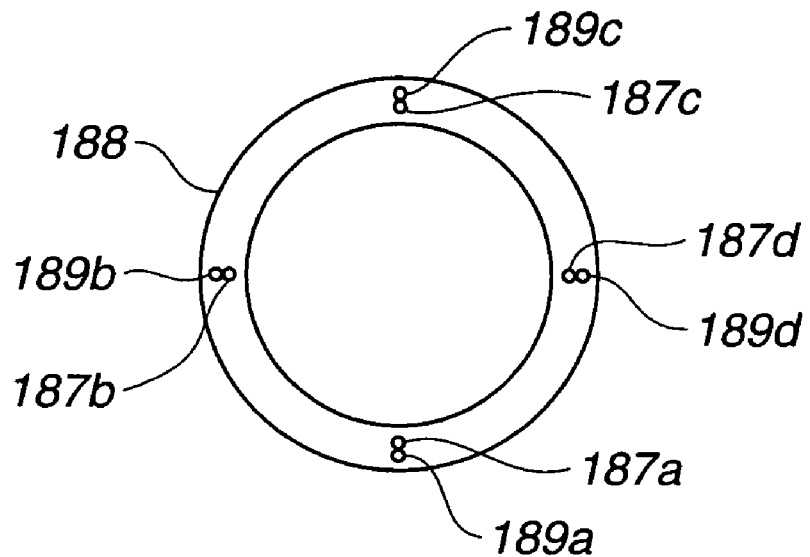
FIG. 42A is a main part enlarged cross-sectional view as taken along the line D-D' in FIG. 41.
Figure 42B:
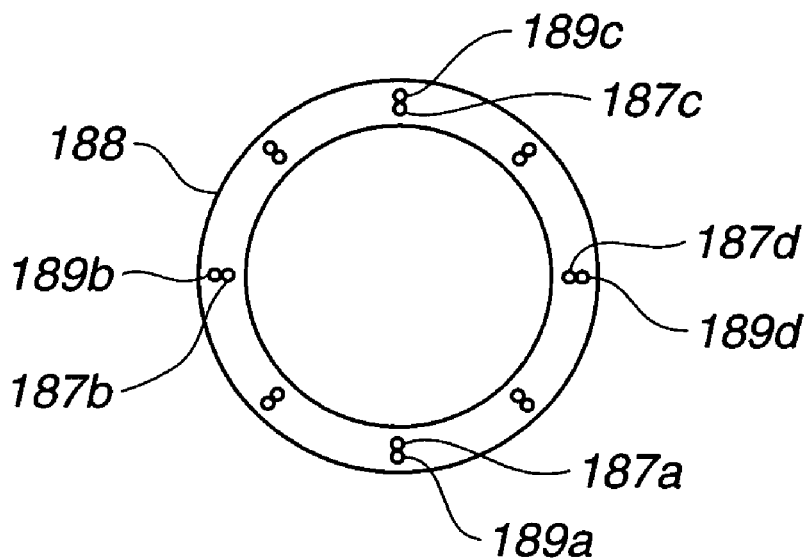
FIG. 42B is another main part enlarged cross-sectional view as taken along the line D-D' in FIG. 41.

FIG. 38 is a main part enlarged cross-sectional view showing a structure of the endoscope on a distal end side of an insert section in the endoscopic system according to the sixth embodiment of the present invention. FIG. 39 is a main part enlarged cross-sectional view showing a structure of the endoscope on a distal end side of the insert section in the endoscopic system according to a first modified example of the sixth embodiment. FIG. 40 is a main part enlarged perspective view showing a structure of the endoscope on a distal end side of the insert section in the endoscopic system according to a second modified example of the sixth embodiment. FIG. 41 is a main part enlarged cross-sectional view showing the structure of the endoscope on the distal end side of the insert section in the endoscopic system according to the second modified example of the sixth embodiment. FIGS. 42A and 42B are main part enlarged cross-sectional views as taken along the line D-D' in FIG. 41.

In the endoscope 3 according to the fifth embodiment, the contact sensors 142*a* to 142*d* are provided at the respective positions of up, down, left, and right in the periphery of the distal end section 24. Whereas in the endoscope 3B according to the sixth embodiment, contact sensors 171*a* to 171*d*, and 172*a* to 172*d* are further provided at positions near the rear end of the bending section 27 and positions on the further back side of the bending section 27.

The contact sensors 171*a* to 171*d* will be described below.

In the vicinity near the rear end of the bending section 27, an LED 173 and the light detection device array 174 are arranged. The light of the LED 173 is guided by the optical fibers 175*i* into pressure deformation members 176*i*, and one ends of a pair of optical fibers 177*i* are arranged in the pressure deformation member 176*i*. Then, the light detected by optical fibers 177*i* is received by the light detection device array 174.

The LED 173 and the light detection device array 174 are connected via the signal lines to the control circuit 57. The contact sensors 172*a* to 172*d* have the same structure so the description will be omitted.

In this embodiment, it is possible to detect a state where the periphery section of the distal end section 24 (to be specific, at the positions of up, down, left, and right) is pressed and deformed while contacting the body cavity inner wall, and at the same time it is possible to detect a pressed deformed state at the positions of up, down, left, and right in the outer circumferential surface near the rear end of the bending section 27 and a pressed deformed state at the positions of up, down, left, and right in the outer circumferential surface on the further back side of the bending section 27.

In this embodiment too, the detection outputs from the contact sensor 142*a* to 142*d*, 171*a* to 171*d*, and 172*a* to 172*d* are input to the control circuit 57. While the bending section 27 is bent, when the pressure amount is detected, the bending to the side where the pressure amount is detected is suppressed, whereby the smooth insertion or the like can be performed.

In the sixth embodiment, as in the fifth embodiment, the distal end section 24 has sensors near the rear end of the bending section 27 and on the further rear end side in addition to the contact sensor 142*a* to 142*d*. Thus, the pressure status in a wider area in the insert section 21 can be detected. Other structure has the same operations and effects as those in the first embodiment.

It should be noted that in the sixth embodiment, a light source for detecting the pressure amount is used, which is different from the LED 56 that generates the illumination light. However, it is also possible to adopt a structure of detecting the pressure amount by using the light from the light flux on the periphery side of the LED 56.

FIG. 39 shows a structure of the endoscope 3C on the distal end side according to a first modified example. According to this modified example, in the structure shown in FIG. 38, the contact sensors 197*a* to 197*d* are arranged at four positions of up, down, left, and right on the inner side of the bending section 27, for example. In FIG. 39, the contact sensors 197*a* and 197*c* are shown on the up and down sides. Then, the outputs from the contact sensors 197*j* are used for detection section for detecting the bending status in the up, down, left, and right directions of the bending section 27.

In other words, if the bending section 27 is bent, for example, in the down direction, such a pressure is effected that the contact sensor 197*a* inside thereof is pressed so as to be crashed. The light quantity change to be detected is occurred, and a relation between the bending amount (bending angle) and the light quantity change is checked in advance, and the data is referenced, whereby the bending amount can be detected.

FIG. 40 shows a shape on the distal end side of the insert section 21 in the endoscope 3D according to a second modified example. In this modified example, a tapered section 181 is provided in the distal end peripheral part of the distal end section 24. Also, at the rear end part of the bending section 27, an increased diameter rigid section 182 which is thicker than the outer diameter of the insert section 21 is provided.

FIG. 41 shows an internal structure on the distal end side of the insert section 21 in the endoscope 3D. In this modified example, an illuminating LED 184 is arranged inside the increased diameter rigid section 182. A light guide fiber bunch 185 whose rear end (entry terminal) is arranged so as to oppose the LED 184 transmits the illumination light of the LED 184 to be output from the distal end surface fixed to the illumination window of the distal end section 24 via an illumination lens 186 toward the front side.

Also, light guide fibers 187*a*, 187*b*, 187*c*, and 187*d* are arranged ring-shaped at an outermost periphery of the light guide fiber bunch 185, whereby a pat of the illumination light of the LED 184 is entered.

Then, the illumination light of the LED 184 entering from the rear end of the respective light guide fibers 187*j* is guided to exit from the distal end surface. The distal end of the respective light guide fibers 187*j* is arranged inside a circular ring pressure deformation member 188 arranged at the tapered section 181 of the distal end section 24, causing the guided light to exit.

FIG. 42A is a cross sectional view of the light guide fibers 187*j* (and 189*j*) arranged inside the circular ring pressure deformation member 188 as seen from the D-D' line in FIG. 41. It should be noted that as shown in FIG. 42B, light guide fibers 187 (and 189) may be provided in a direction other than the directions of up, down, left, and right.

Inside the pressure deformation member 188, a distal end surface of the light guide fibers 189*j* forming a pair with the light guide fibers 187*j* is arranged. The light entering after reflected by the pressure deformation member 188 is guided to the rear end. A light detection device array 190 is arranged at the rear end thereof to receive and photoelectrically convert the guided light. The outer periphery of the pressure deformation member 188 is covered with a protecting member 191.

Also, in this modified example, for example, a reference pressure deformation member 192 having substantially the same shape and characteristic as those of the pressure deformation member 188 is arranged inside the increased diameter rigid section 182. In addition, the pressure deformation member 192 is set in a status where no deformation is effected.

Furthermore, inside the pressure deformation member 192, by using the light guides 193*j* at the outermost periphery of the light guide fiber bunch 185, the light is guided into the pressure deformation member 192. Then, the light guides 194*j* forming the pair with the light guides 193*j* guide the light into the light detection device of the light detection device array 190.

Moreover, the light guided by the light guide 194*j* is used as the reference and by detecting the change amount from the photoelectric conversion output value of the light in that case, the press (contact) can be detected with high precision.

It should be noted that the optical fibers 193*j* and 194*j* on the reference side may be provided by only one pair to simplify the structure. In this case, it also suffices that the pressure deformation member 192 is only provided in the vicinity of the reference optical fibers 193 and 194 instead of the providing in a circular ring manner similarly to the pressure deformation member 188.

According to this modified embodiment, the pressure amount can be detected with further satisfactory precision.

It should be noted that embodiments and the like which are structured by combining parts of the above-mentioned embodiments are within the scope of the present invention.

Next, a seventh embodiment of the present invention will be described.

Figure 43:
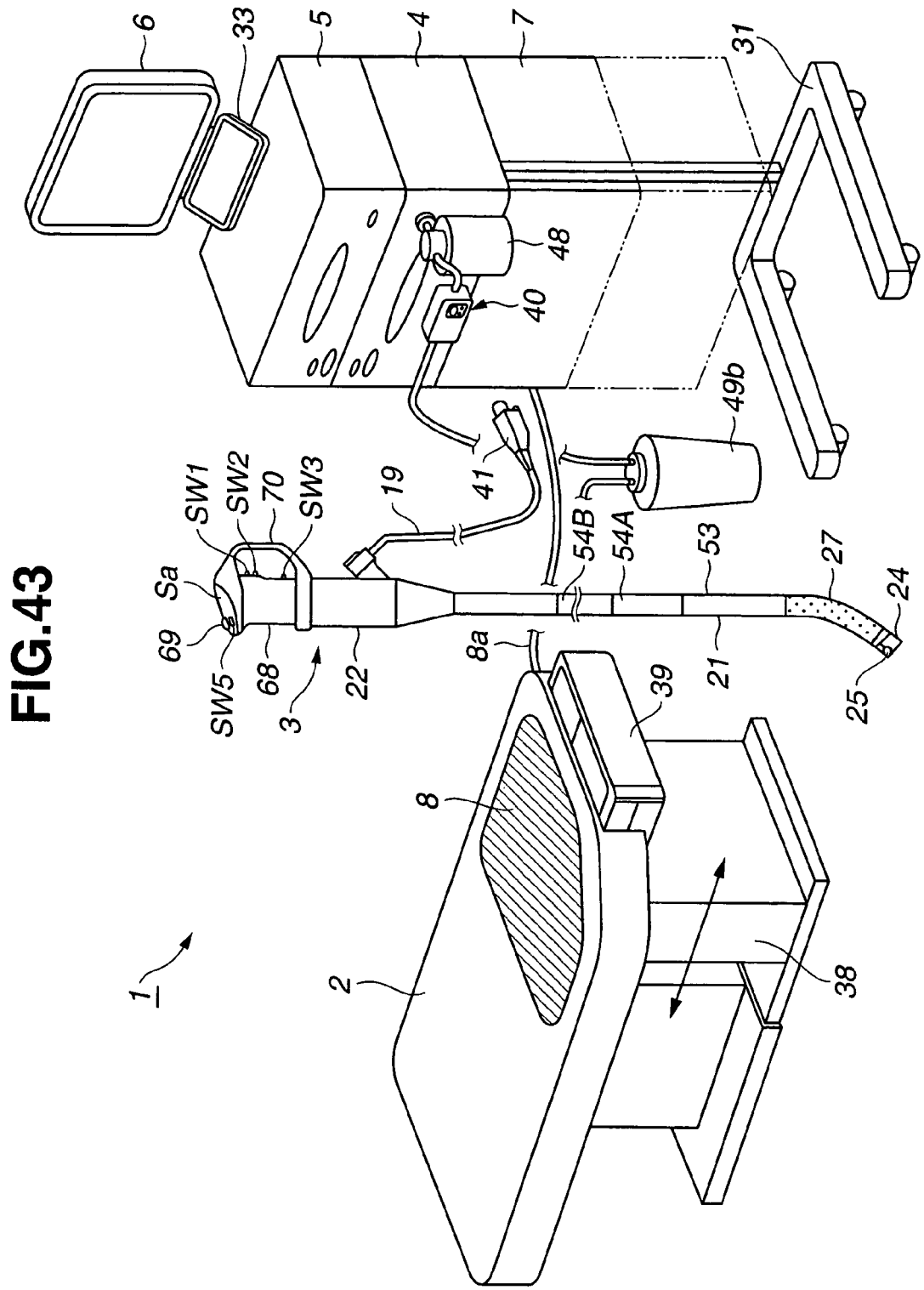
FIG. 43 shows an overall structure of an endoscopic system according to a seventh embodiment of the present invention.
Figure 44:
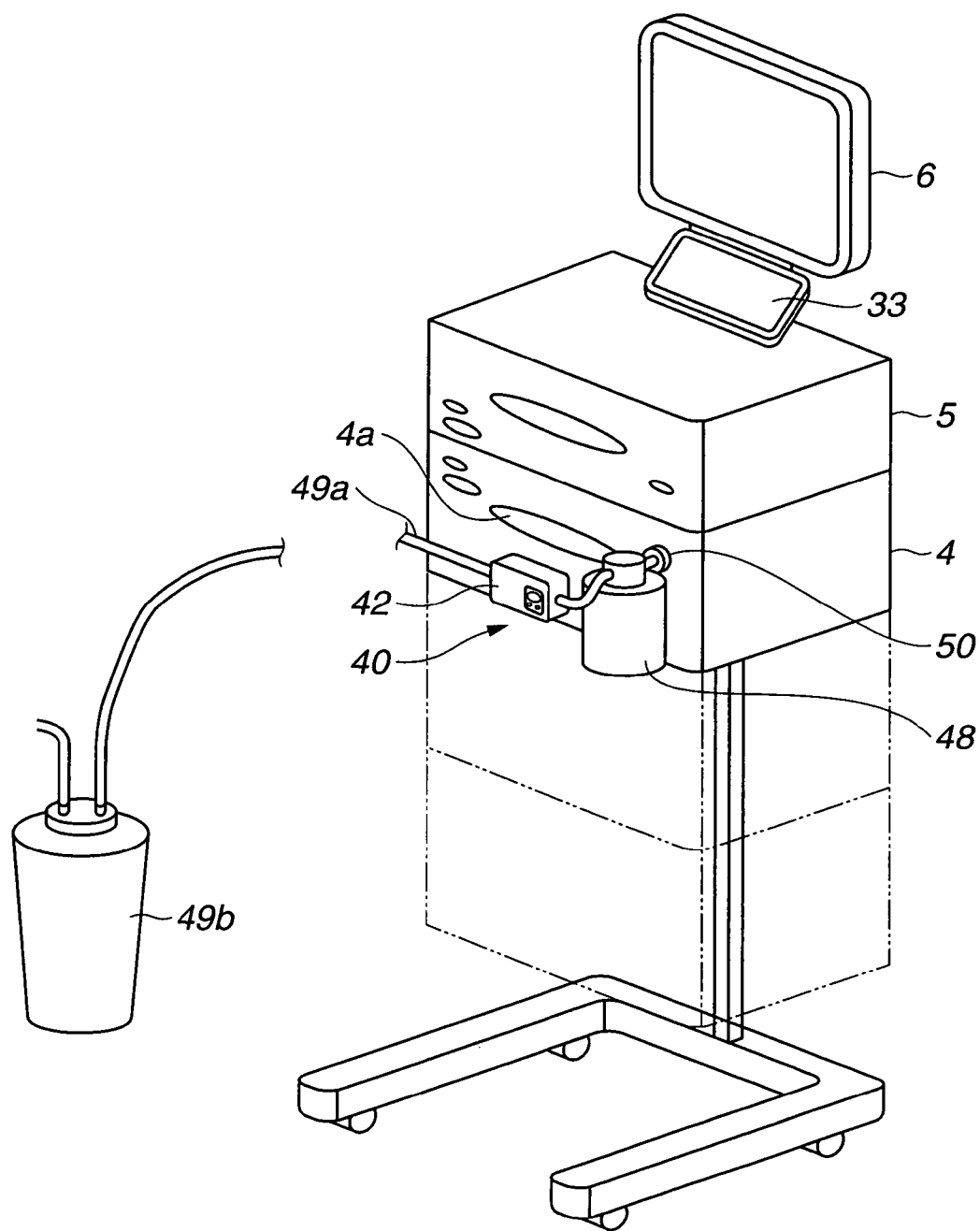
FIG. 44 is a perspective view showing a specific appearance shape of an AWS unit periphery section in the endoscopic system according to the seventh embodiment.

FIG. 43 shows an overall structure of an endoscopic system according to the seventh embodiment of the present invention. FIG. 44 is a perspective view showing a specific appearance shape of an AWS unit periphery section in the endoscopic system according to the seventh embodiment.

As shown in FIG. 43, the endoscopic system 1 includes the flexible endoscope (also referred to as scope) 3 for performing an endoscopic inspection by inserting the endoscope in a body cavity of a patient (not shown) lying on an inspection bed 2. The endoscopic system 1 includes the air water supply/suction unit having functions of airing, watering, and suction (hereinafter, abbreviated as AWS unit) 4, the endoscopic system control device 5 for performing a signal process on the image pickup element built in the endoscope 3 and a control process, a video process, and the like on various operation sections provided to the endoscope 3, and the observation monitor 6 such as a liquid crystal monitor for displaying a video signal generated by the endoscopic system control device 5, which are connected to the endoscope 3. It should be noted that the observation monitor 6 includes the touch panel 33.

In addition, the endoscopic system 1 further includes the image recording unit 7 for filing digital video signals, for example, generated by the endoscopic system control device 5, and the UPD coil unit 8 connected to the AWS unit 4, for displaying, when shape detecting coils (hereinafter, abbreviated as UPD coil) are built in the insert section of the endoscope 3, a shape of the insert section of the endoscope 3 by detecting each position of the UPD coils while a magnet field is received by the UPD coil.

In the case of FIG. 43, the UPD coil unit 8 is provided while embedded in an upper surface of the inspection bed 2. Then, the UPD coil unit 8 is connected to the AWS unit 4 via a cable 8*a*.

Also, in this embodiment, an accommodating concave portion is formed at one end section in the longitudinal direction of the inspection bed 2 and a position below the end section, whereby the tray conveyance trolley 38 can be accommodated. An endoscope tray 39 for accommodating the endoscope 3 is placed on an upper part of the tray conveyance trolley 38.

Then, the endoscope tray 39 accommodating the endoscope 3 after sterilization or disinfection can be conveyed by the tray conveyance trolley 3 8 and can be accommodated in the accommodating concave portion of the inspection bed 2. The surgeon can use the endoscope 3 by removing from the endoscope tray 39 and also accommodate the endoscope 3 in the endoscope tray 39 after the end of the endoscopic inspection again. After that, with use of the tray conveyance trolley 38, by conveying the endoscope tray 39 accommodating the endoscope 3 after use, sterilization or disinfection can be performed smoothly as well.

Then, the AWS unit 4 and the endoscopic system control device 5 shown in FIG. 43 wirelessly perform information transmission and reception in this embodiment. It should be noted that in FIG. 43, the endoscope 3 is connected to the AWS unit 4 via a tube unit 19, but wireless information transmission and reception (bidirectional transmission) may be performed. The endoscopic system control device 5 may wirelessly perform information transmission and reception with the endoscope 3.

It should be noted that in this embodiment too, the three method for the transmission and reception unit (communication section) for performing data transmission and reception between the unit and device, between the endoscope 3 and the unit, or between the devices in the endoscopic system 1 are the same as those in the first embodiment.

As shown in FIG. 43, the endoscope 3 of this embodiment includes the endoscope main body 18 and the disposal tube unit 19 detachably connected to the endoscope main body 18.

The endoscope main body 18 includes an elongated flexible insert section 21 inserted in the body cavity, and an operation section 22 provided at a rear end of the insert section 21. A base end of the tube unit 19 is detachably connected to the operation section 22.

In addition, an image pickup unit is arranged at a distal end section 24 of the insert section 21 as the image pickup element. The image pickup unit uses a charged coupled device (abbreviated as CCD) 25 capable of varying a gain inside the image pickup element.

A bending section 27 which can be bent with a small power is provided at a rear end of the distal end section 24. By operating a track ball 69 as an operation section (instruction input section) provided at the operation section 22, the bending section 27 can be bent. The track ball 69 is also used for the articulation operation (bending operation) and changing and setting of other endoscope switch functions, for example, setting of articulation sensitivity, airing amount, and the like.

Consistency varying sections including consistency varying actuators 54A and 54B which are consistency variable are formed at plural locations of the insert section 21, whereby an insert operation or the like can be smoothly performed.

In this embodiment, the AWS unit 4 and the endoscopic system control device 5 side perform the data transmission and reception, for example, with wireless transmission and reception units 77 and 101, as shown in FIG. 8. Then, the observation monitor 6 is connected to a monitor connector 35 of the endoscopic system control device 5 with use of a monitor cable.

As will be described later, image data captured by a CCD 25 from the AWS unit 4 side and image data of the insert section shape of the endoscope 3 detected by using the UPD coil unit 8 (the UPD image) are transmitted to the endoscopic system control device 5. Thus, the endoscopic system control device 5 transmits video signals of the image data to the observation monitor 6, whereby the UPD image can be also displayed with the endoscope image on the display screen.

The observation monitor 6 is composed of a monitor of a high definition TV (HDTV) so that images of plural types can be displayed on the image screen at the same time in this way.

Furthermore, as shown in FIG. 43, for example, the AWS unit 4 includes an endoscope connector 40. Then, an endoscope connector 41 of the endoscope 3 is detachably connected to the endoscope connector 40.

In this case, FIG. 44 shows an outer appearance shape of the endoscope connector 40 on the AWS unit 4 side (also refer to FIGS. 6A AND 6B). Other structure of the AWS unit 4 is the same as that in the first embodiment.

Next, the endoscope according to a seventh embodiment will be described.

Figure 45:
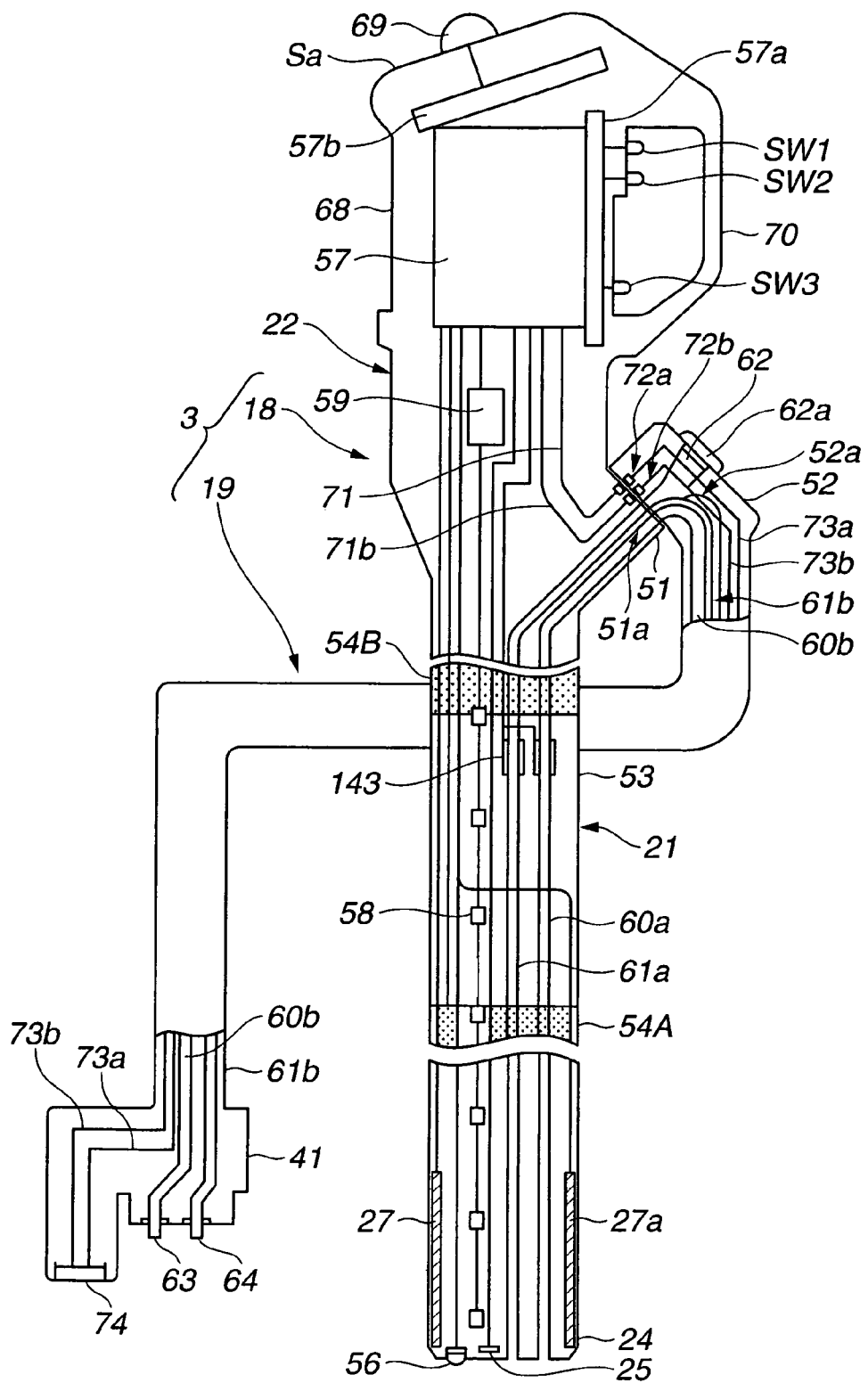
FIG. 45 is a side view with a see-through of a part of an internal structure component of an endoscope in the endoscopic system according to the seventh embodiment.

FIG. 45 is a side view with a see-through of a part of an internal structure component of an endoscope in the endoscopic system according to the seventh embodiment. FIGS. 46A to 46E show a specific outer appearance shape of the endoscope in the endoscopic system according to the seventh embodiment.

Figure 47A:
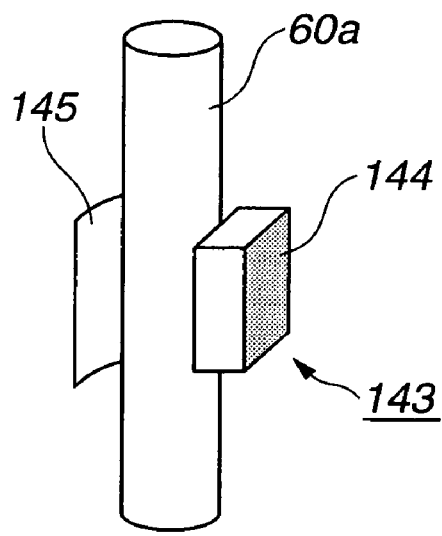
FIG. 47A shows a structure of a transparency sensor of the endoscope in the endoscopic system according to the seventh embodiment.
Figure 47B:
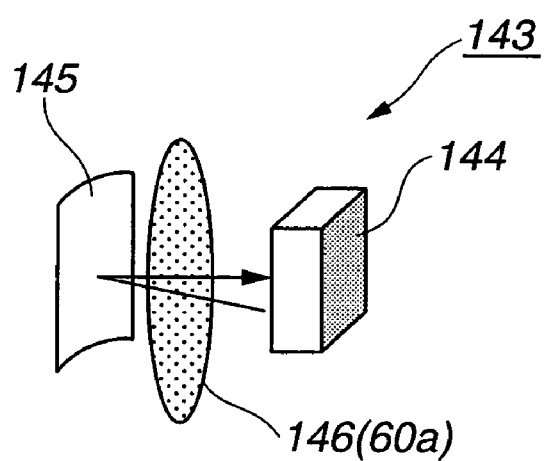
FIG. 47B shows an operation of the transparency sensor of the endoscope in the endoscopic system according to the seventh embodiment.
Figure 48:
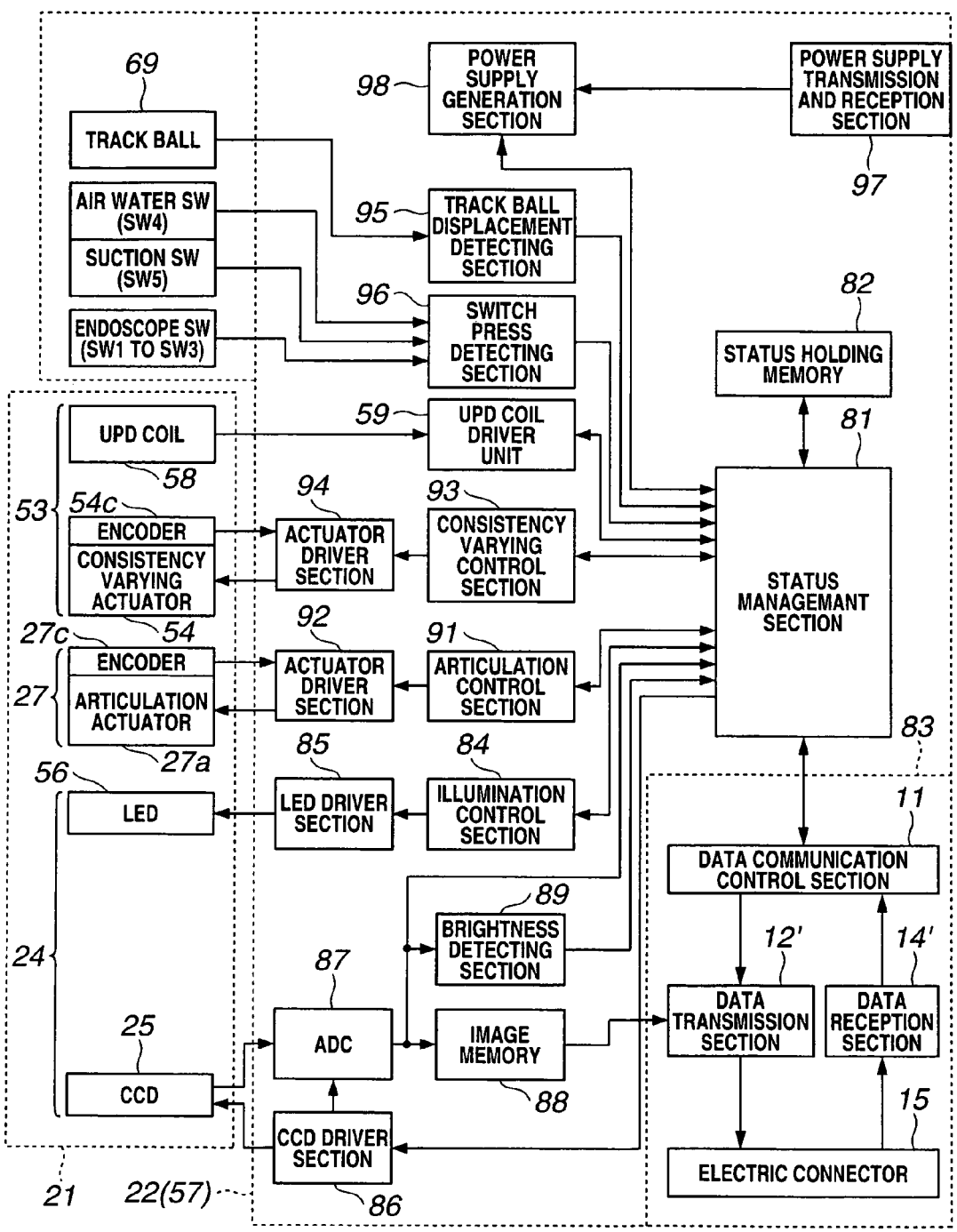
FIG. 48 is a block diagram showing an electric structure of the endoscope in the endoscopic system according to the seventh embodiment.

FIGS. 47 show a structure and an operation of a transparency sensor of the endoscope in the endoscopic system according to the seventh embodiment. FIG. 48 is a block diagram showing an electric structure of the endoscope in the endoscopic system according to the seventh embodiment.

It should be noted that FIG. 46A shows a vicinity of the operation section of the endoscope 3 from a side, FIG. 46B is a front view as seen from the right hand side of FIG. 46A, FIG. 46C is a back view as seen from the left hand side of FIG. 46A, FIG. 46D is a plan view as seen from the top of FIG. 46A. Then, FIG. 46E shows an example of an optimal angle range of the inclined surface.

In FIG. 43, as the outline has been described, the flexible endoscope 3 includes the endoscope main body 18 having the elongated flexible insert section 21 and the operation section 22 provided at the rear end, and the disposal tube unit 19 having an overall connecter section 52 at the base end which is detachably connected to a (tube unit connection) connecter section 51 in the vicinity of a base end (front end) of the operation section 22 in the endoscope main body 18.

The endoscope connector 41 detachably connected to the AWS unit 4 described above is provided to a tail end of the tube unit 19.

The insert section 21 includes the rigid distal end section 24 provided at the distal end of the insert section 21, the freely bendable bending section 27 provided at the rear end of the distal end section 24, and an elongated flexible portion (corrugated tube section) 53 extending from the rear end of the bending section 27 to the operation section 22. The consistency varying actuators 54A and 54B formed of an electroconductive polymer artificial muscle (abbreviated as EPAM) or the like which expands upon voltage application while the consistency can be changed) are provided at plural positions, to be specific, two locations, in the middle way of the flexible portion 53.

For example, a light emitting diode (abbreviated as LED) 56 is arranged as the illumination section on an inner side of an illumination window provided to the distal end section 24 of the insert section 21. The illumination light of the LED 56 is output forward via an illumination lens integrally attached to the LED 56 for illuminating a subject such as an affected area. It should be noted that the light emitting element forming the illumination section is not limited to the LED 56, and the illumination section can be formed by using an LD (laser diode) or the like.

An objective lens not shown is attached to the observation window adjacently provided to this illumination window, and the CCD 25 including the gain varying function is arranged at the image forming location, thereby forming the image pickup section for capturing the subject.

The signal line that is inserted in the insert section 21 and whose ends are connected to the LED 56 and the CCD 25, respectively, is provided in the operation section 22 and connected to the control circuit 57 for performing a central control process (collective control process).

The UPD coils 58 are arranged at plural positions with a predetermined interval along the longitudinal direction in the insert section 21, and the signal line connected to each of the UPD coils 58 is connected to the control circuit 57 via a UPD coil driver unit 59 provided in the operation section 22.

Also, the articulation actuators 27a formed by arranging EPAM in the longitudinal direction as articulation elements (bending elements) are arranged at four locations in the circumferential direction on the inner side of an outer skin in the bending section 27. The articulation actuator 27a and the consistency varying actuators 54A and 54B are also connected the control circuit 57 via the signal line. The control circuit 57 is structured by mounting, for example, electronic circuit elements on a switch board 57a and a track ball board 57b.

The EPAM used for the articulation actuator 27a and the consistency varying actuators 54A and 54B has, for example, electrodes attached on board-shaped both sides. With the application of a voltage, contraction in a thickness direction is caused, whereby expansion in the longitudinal direction can be achieved. It should be noted that this EPAM can vary a warpage, for example, in proportion to approximately a square of the applied voltage.

When used as the articulation actuator 27a, the EPAM is formed into a wire to expand on one side and contract on the other side, thereby bending the bending section 27 similarly to the normal wire function. Also, with the expansion or contraction, the consistency can be varied. By using the functions of the EPAM, the consistency varying actuators 54A and 54B can vary, the consistency of that part.

An air water duct line 60a and a suction duct line 61a are inserted through the insert section 21, and the rear end functions as a duct line connector 51a which is opened in the connecter section 51. Then, a duct line connector 52a in the overall connecter section 52 at the base end of the tube unit 19 is detachably connected to the duct line connector 51.

Then, the air water duct line 60a is connected to an air water duct line 60b inserted through the tube unit 19. The suction duct line 61a is connected to a suction duct line 61b inserted through the tube unit 19 and is branched in the duct line connector 52a to have an opening at the outside, which is in communication with an insertion port (also referred to as biopsy port) 62 for allowing insertion of an endo-therapy product such as forceps. The biopsy port 62 is closed by a forceps valve 62a when not used.

The rear ends of the air water duct line 60b and the suction duct line 61b function as the air water connecter 63 and the suction connecter 64 in the endoscope connector 41.

The air water connecter 63 and the suction connecter 64 are connected to the air water connecter 42c and the suction connecter 42d of the AWS adapter 42, respectively. Then, the air water connecter 42c is branched into the air duct and the water duct line inside the AWS adapter 42, the air duct is connected to an airing watering pump 65 in the AWS unit 4 via an electromagnetic valve B1, whereas the water duct line is connected to the watering tank 48. Also, the watering tank 48 is connected to the airing watering pump 65 via an electromagnetic valve B2 in the middle way.

The airing watering pump 65, and the electromagnetic valves B1 and B2 are connected to the AWS control unit 66 through a control line (driver line). With the AWS control unit 66, closing and opening are controlled, whereby airing and watering can be conducted. It should be noted that the AWS control unit 66 performs an operation control for suction under the control of opening and closing of the pinch valve 45.

Then, the operation section 22 of the endoscope main body 18 includes a grasping section 68 grasped by the surgeon. According to this embodiment, as shown in FIGS. 46A to 46D, the grasping section 68 is formed of a side part of a cylindrical shape, for example, in the vicinity of the rear end (base end) in the operation section 22 (on the opposite side to the insert section 21).

Regarding the grasping section 68, in the peripheral section including the grasping section 68, for example, three endoscope switches SW1, SW2, and SW3 for performing remote control operations such as release and freeze are arranged along a longitudinal axial direction of the grasping section 68, which are connected to the control circuit 57 (refer to FIG. 45).

Furthermore, a base end surface at the rear end (base end) of the grasping section 68 (or the operation section 22) (referred to as upper end surface in general, because the base end side is set as the up direction as shown in FIGS. 46A to 46D to be used in the endoscopic inspection) is formed to be an inclined surface Sa. The track ball 69 of a water proof structure for performing the articulation operation (bending operation) and setting of other remote control operation by switching from the articulation operation is provided in the vicinity of the opposite side to the locations where the endoscope switches SW1, SW2, and SW3 are provided in the inclined surface Sa. It should be noted that the water proof structure in this case refers to, in actuality, a structure in which the encoder side for rotatably holding the track ball 69 and detecting the rotation amount of the track ball 69 is covered with a water proof coating, and the track ball 69 is rotatably held outside thereof In addition, a substantially U-shaped hook 70 is provided for connecting vicinities of both the end of the longitudinal direction in the grasping section 68 provided in the vicinity of the rear end of the operation section 22. As shown in FIG. 46B, the surgeon puts a finger of the hand into the inside of the hook 70 for grasping by right hand (or left hand), even in the case in which the grasping section 68 is not firmly grasped, the endoscope 3 can be effectively prevented from dropping due to the weight.

In other words, even if the endoscope 3 tries to drop due to the weight, a lower side of the hook 70 is touched by the hand, whereby the drop of the endoscope 3 can be prevented. In this way, in this embodiment, even when the surgeon does not grasp (hold) the grasping section 68 firmly, the endoscope 3 can be effectively prevented from dropping down due to the weight. Therefore, in the case where the surgeon performs various operations while grasping the grasping section 68 and the surgeon is tired from using the grasping hand or finger for the operations, even when the surgeon stops grasping (holding) the grasping section 68, if the surgeon puts a part of the hand into the hook 70, the drop of the endoscope 3 or the like can be prevented, so the operability can be improved.

Also, as shown in FIGS. 46A to 46C, the air water switch SW4 and the suction switch SW5 are bilaterally symmetrically arranged on both sides of the track ball 69 in the inclined surface Sa.

The track ball 69 and the endoscope switches SW4 and SW5 are also connected to the control circuit 57. As will be described further with reference to FIG. 46A to FIG. 46D, the operation section 22 or the grasping section 68 has a shape bilaterally symmetric to a center line O (as the reference line) extending in the longitudinal direction of the operation section 22 or the grasping section 68 in the front view shown in FIG. 46B. The inclined surface Sa at a location on the center line O has the track ball 69 arranged. Then, the air water switch SW4 and the suction switch SW5 are arranged at bilaterally symmetric positions on both the sides of the track ball 69.

A back view on the opposite side to this front view is FIG. 46C. In this back view too, the three endoscope switches SW1, SW2, and SW3 are arranged on the outer surface of the grasping section 68 so as to be bilaterally symmetric with respect to the center line O on the center line O.

Also, in this embodiment, as shown in FIG. 46A, the inclined surface Sa is formed of an angle φ which is an angle larger than 90° with respect to a parallel line to the center line O or the side face of the grasping section 68. In other words, the inclined surface Sa is formed to be an inclined surface to have an angle θ with respect to a surface perpendicular to the center line O of the grasping section 68. The track ball 69, and the air water switch SW4, and the suction switch SW5 are bilaterally symmetrically provided at low section side positions in the inclined surface Sa. Then, as shown in FIG. 46B, with a thumb of the grasping hand, the track ball 69 or the like can be easily operated.

As described above, the inclined surface Sa can be operated when an angle φ is an obtuse angle to the center line O, in other words, from 90° to 180°. More specifically, as shown in FIG. 46E, if the angle is from 120° that is an angle φ 1 to 150° that is an angle φ 2, a further satisfactory operability can be ensured.

In this manner, in this embodiment, the operation section (instruction input section) such as the track ball 69 provided to the operation section 22 is arranged bilaterally symmetric to the center line O in the longitudinal direction of the grasping section 68, thereby attaining one feature that is the satisfactory operation even when the surgeon grasps by using the right hand or the left hand.

Also, the grasping section 68 includes the hook 70 for connecting substantially both the ends in the longitudinal direction of the grasping section 68 by forming the ends into a substantially U-shaped. Even if the surgeon does not sufficiently grasp the grasping section 68, as the index finger or the like is inserted inside the hook 70, when the endoscope 3 drops down due to the weight, the hook 70 is hooked by the index finger or the like, thereby providing the function of effectively preventing the drop of the endoscope 3.

Also, in this embodiment, the grasping section 68 is formed in the vicinity of the rear end of the operation section 22, and a connection section with the tube unit 19 is provided at a position nearer to the insert section 21 than the grasping section 68. Thus, it is possible to reduce the effect of eccentricity of the gravity center of the grasping section 68 when grasped, from the position of the center axis.

In other words, if the tube unit 19 is extended to the side from the rear side (upper side) position than the grasping section position of the prior art, the position of the gravity center at that case is easy to decenter due to the weight of the tube unit. In this embodiment, the tube unit 19 is extended from a position nearer the insert section 21 than the grasping section 68, in other words, toward the side from the position on the lower side. Thus, the eccentricity of the gravity center position can be reduced, and the operability can be improved.

Then, in the endoscope 3 of this embodiment as well, when the operator (the user) such as the surgeon grasps the grasping section 68 by the left hand or the right hand, such a state that the inner surface side of the hook 70 is lightly touched by an area in the vicinity of the side section of the index finger. Even if the gravity center position is decentered to cause an effect that the center axis is inclined, (in other words, the longitudinal direction of the operation section 22 is inclined), the hook 70 is touched by the hand and the inclination is restricted, whereby the satisfactory operability can be ensured.

As shown in FIG. 45, a power supply line 71a and a signal line 71b extending from the control circuit 57 are connected via electromagnetic coupling connection sections 72a and 72b that are formed in the connecter section 51 and the overall connecter section 52 to a power supply line 73a and a signal line 73b inserted through the tube unit 19 by way of electromagnetic coupling. The power supply line 73a and the signal line 73b are connected to a power supply and signal terminal which form an electric connector 74 in the endoscope connector 41.

Then, while the user connects the endoscope connector 41 to the AWS unit 4, the power supply line 73a is connected to the power supply unit 75 via the endoscope electric connector 43 of the AWS unit 4, and the signal line 73b is connected (via the power supply unit 75) the UPD unit 76, the transmission and reception unit 77, and the AWS control unit 66. It should be noted that the transmission and reception unit 77 is connected to the antenna section 77a for performing wireless transmission and reception of radio waves.

In addition, as shown in FIG. 45, transparency sensors 143 are provided in the midway of the air water duct line 60a and the suction duct line 61a, making it possible that each duct line of the air water duct line 60a and the suction duct line 61a formed of a transparent tube is transmitted with light to detect the contamination degree of the inner wall of the duct line and the transparency of fluid passing through the inside of the duct line.

The transparency sensor 143 is connected to the control circuit 57 with a signal line. FIGS. 47A and 47B are explanatory diagrams for the effect of the washing level detection by the transparency sensor 143.

As shown in FIG. 47A, a photo reflector 144 and the reflection mirror 145 are arranged so as to oppose to each other on the outer periphery of the air water duct line 60a (same in the suction duct line 61a) formed of a transparent tube, thereby forming the transparency sensor 143.

Then, as shown in FIG. 47B, the light emitted by the light emitting element forming the photo reflector 144 is output to the reflection mirror 145 side, and the reflection light reflected by the reflection mirror 145 is received by a light reception element forming the photo reflector 144.

In this case, in actuality, as a transmittance detection body 146 such as the air water duct line 60a formed of a transparent tube is arranged between the photo reflector 144 and the reflection mirror 145, when a transparent washing liquid is poured into the inner wall side of the air water duct line 60a to wash the air water duct line 60a, once the inner wall surface is in a clean state, the light reception element of the photo reflector 144 receives larger light quantity, so the washing degree can be detected.

Therefore, with this function, the washing level of the inner wall surface of the air water duct line 60a and that of the inner wall surface of the suction duct line 61a can be quantitative detected.

It should be noted that in the description in this case, the operation in the case of washing with a cleaning solution has been described. During the endoscope inspection or the like, by referring to the detection output of the transparency sensor 143, the contamination levels on the inner wall surface of the air water duct line 60a and the inner wall surface of the suction duct line 61a can be found out. Moreover, it is possible to detect the transparency, to put it the other way around, the turbidity, of a physiological fluid when the physiological fluid or the like is brought into a body cavity.

If it suffices that the photo reflector 144 outputs light to a transparent duct line section such as the air water duct line 60a and detects the light quantity of the light transmitted through the transparent duct line section and reflected by a reflection mirror 145, the transparent tube section may only form a part of the air water duct line 60a instead of the whole of the air water duct line 60a or the like.

Thus, even when the endoscope is being used, it is possible to detect the contamination of the duct line, the transparency of the fluid passing through the duct line, or the like. In addition, during the endoscope cleaning and disinfection, the photo detector can be used as the cleaning level detector, and the output can be used as an output which indicates the cleaning level.

FIG. 48 shows the control circuit 57 and the like arranged in the operation section 22 of the endoscope main body 18 according to the seventh embodiment and a structure of an electric system of main component elements arranged at the respective sections of the insert section 21.

The CCD 25 and the LED 56 are arranged at the distal end section 24 of the insert section 21 shown in the lower section on the left hand side of FIG. 43. The articulation actuator (in this embodiment, specifically, EPAM) 27a and an encoder 27c are arranged at the bending section 27 shown in the upper section in the drawing. The consistency varying actuator(In this embodiment, specifically, EPAM) 54 and an encoder 54c are arranged are arranged at the flexible portion 53 shown in the upper section in the drawing. In addition, the transparency sensor 143 and the UPD coil 58 are arranged in the flexible portion 53.

Moreover, the track ball 69, the air water SW (SW4), the suction SW (SW5), and the endoscope SW (SW1 to SW3) are arranged on the surface of the operation section 22 in the upper section of the flexible portion 53 in the insert section 21. It should be noted that as will be described later, with the operation of the track ball 69, a function of selecting and setting the articulation operation and other functions is allocated.

As shown in the left hand side of FIG. 48, these are connected to via the signal line to the control circuit 57 including most of the inside of the operation section 22 shown on the right hand side (but except for the UPD coil driver unit 59 and the like), and the control circuit 57 performs the drive control for the functions, a signal processing, etc.

The control circuit 57 includes the status management section 81 composed of the CPU for managing the control status and the like. The status management section 81 is connected to the status holding memory 82 for holding (storing) the status of the respective sections and also to the transmission and reception unit 83 of the wired method for performing wired communication with the AWS unit 4 (in this embodiment).

Then, the status management section 81 controls via an illumination control section 84 for controlling the illumination to a LED driver section 85 that is controlled by the illumination control section 84. The LED driver section 85 applies the LED 56 with the LED driver signal to cause the LED 56 functioning as the illumination section to emit light.

With the light emittance of the LED 56, the illuminated subject such as the affected area is image-focused on an image pickup surface of the CCD 25 located at the image forming location by an objective lens not shown attached to the observation window, and photoelectric conversion is performed by the CCD 25.

In response to the CCD driver signal application from a CCD driver section 86 controlled by the status management section 81, the CCD 25 outputs the signal charge accumulated through the photoelectric conversion in the form of the image pickup signal. The image pickup signal is converted from an analog signal to a digital signal by an A/D converter (abbreviated as ADC) 87 and then input to the status management section 81. At the same time, the digital signal (image data) is stored in an image memory 88. The image data in the image memory 88 is sent to the data transmission section 12' of the transmission and reception unit 83.

Furthermore, although not shown in the drawing, the above-mentioned output value of the transparency sensor 143 is also input to the status management section 81 as the data on the duct line contamination or the transparency of the fluid passing through the duct line. The data is supplied from the transmission and reception unit 83 to the AWS unit 4.

Then, the image data is transmitted to the AWS unit 4 side from the electric connector 15 via the signal line 73b in the tube unit 19. Furthermore, the image data is wirelessly transmitted from the AWS unit 4 to the endoscopic system control device 5.

As shown in FIG. 8, the image data transmitted to the endoscopic system control device 5 is wirelessly received by the transmission and reception unit 101. A video signal is generated through the image processing by the image processing unit 116. The video signal is output from the monitor connector 35 to the observation monitor 6 via the system control unit 117 that controls the overall endoscopic system 1, whereby the endoscope image is displayed on the display screen of the observation monitor 6. It should be noted that in FIGS. 6A and 6B, a power supply unit 100 supplies the transmission and reception unit 101, the image processing unit 116, and the system control unit 117 with the operation power.

As shown in FIG. 48, an output signal of the ADC 87 is sent to a brightness detecting section 89. Information on the image brightness detected by the brightness detecting section 89 is sent to the status management section 81. The status management section 81 performs light intensity adjustment on the basis of this information, so that the illumination quantity by the LED 56 is set to an appropriate brightness via the illumination control section 84.

Then, the status management section 81 controls an actuator driver section 92 via the articulation control section 91 to perform a control for driving the articulation actuator (EPAM) 27a with the actuator driver section 92. It should be noted that the drive amount of the articulation actuator (EPAM) 27a is detected by the encoder 27c so that the drive amount is controlled to match the instructed amount.

The status management section 81 controls the actuator driver section 94 through the consistency varying control section 93. With the actuator driver section 94, the consistency varying actuator (EPAM) 54 (this reference numeral represents 54A and 54B herein) is controlled for the drive. It should be noted that the drive amount of the consistency varying actuator (EPAM) 54 is detected by the encoder 54c so that the drive amount is controlled to be a value corresponding to the instructed amount.

A detection signal from the transparency sensor 143 provided in the flexible portion 53 is converted into signal data corresponding to the transparency by a transparency detecting section 148, and is then input to the status management section 81. The status management section 81 compares the signal data with a reference value of the transparency previously stored in the status holding memory 82 or the like. When the signal data reaches the reference value, the information is transmitted from the transmission and reception unit 83 via the AWS unit 4 to the endoscopic system control device 5 side, and the observation monitor 6 displays that the signal data reaches the reference value.

Data corresponding to the operation amount from the track ball 69 or the like provided to the operation section 22 is input to the status management section 81 via a track ball displacement detecting section 95.

Furthermore, the switch press operation such as turning ON of the air water SW, the suction SW, and the endoscope SW is detected by a switch press detecting section 96, the detected information is input to the status management section 81.

The control circuit 57 includes a power supply transmission and reception section 97 and a power supply generating section 98. The power supply transmission and reception section 97 specifically means a transmission unit 51b in the operation section 22 or the electric connector 74 at the tail end of the tube unit 19. Then, the electric power transmitted from the power supply generating section 98 is converted into a direct current power supply in the power supply generating section 98. The power supply generated by the power supply generating section 98 supplies the respective sections of the control circuit 57 with necessary electric power for the operation.

In the endoscopic system 1 of this embodiment, when the power supply is activated, the observation monitor 6 displays various images shown in FIG. 16A. In this case, in addition to an information display area Rj for displaying patient information or the like, a display area Ri of the endoscope image, a display area Ru of the UPD image, a display area Rf of a freeze image, and a display area Ra of an articulation shape, a menu display Rm is provided. The menu display Rm displays a menu.

As a menu displayed on the menu display Rm, a main menu shown in FIG. 16B is displayed. This main menu displays a return item for return operation instruction for returning to the previous menu screen and an end item for end, in addition to the endoscope switch, the articulation sensitivity, the insert section consistency, zoom, image emphasis, and the airing amount.

Then, when the user selects the endoscope switch item with a selection frame through the operation of the track ball 69 or the like, the frame of the endoscope switch item is displayed in bold and the display indicates the selected state. Furthermore, when the track ball 69 is pressed to perform a determined operation, whereby the functions to be allocated to the five switches SW1 to SW5 can be selected and set as shown in FIG. 16C.

Next, operation of the endoscopic system of the seventh embodiment will be described.

As a prearrangement for the endoscopic inspection, first of all, the overall connecter section 52 of the disposal tube unit 19 is connected to the connecter section 51 in the operation section 22 of the endoscope main body 18. In this case, the electromagnetic coupling connection sections 72a and 72b are connected to each other in an insulated and water tight way. With this connection, the preparation of the endoscope 3 is completed.

Next, the endoscope connector 41 of the tube unit 19 is connected to a connector 40 of the AWS unit 4. With one touch connection of this part, various duct lines, the power supply line, the signal line, and optical connection are completed at once. Unlike the prior art endoscopic system, it is unnecessary to perform connection of various duct lines, connection of the electric connector, and the like on each occasion.

In addition, the user connects the UPD coil unit 8 to the AWS unit 4, and connects the endoscopic system control device 5 to the observation monitor 6. If necessary, the endoscopic system control device 5 is connected to the image recording unit 7 or the like, thereby completing the setup of the endoscopic system 1.

Next, the power supplies of the AWS unit 4 and the endoscopic system control device 5 are turned ON. As a result, the respective sections are activated in the AWS unit 4, the power supply unit 75 can be in a status for supplying the endoscope 3 side with an electric power via the power supply line.

In this case, the AWS unit 4 firstly turns OFF the electric power supply, activates the timer, and confirms that a signal is returned from the endoscope 3 in a given period of time, and then continuously supplies the electric power.

Then, as the surgeon inserts the insert section 21 of the endoscope 3 in the body cavity of the patient, the subject such as the affected area in the body cavity is captured by the CCD 25 provided to the distal end section 24 of the insert section 21. The captured image data is wirelessly transmitted via the AWS unit 4 to the endoscopic system control device 5 to generate a video signal through image processing, whereby the subject body image is displayed as the endoscope image on the display screen of the observation monitor 6. Therefore, while the surgeon observes the endoscope image, a diagnosis on the affected area or the like is performed, and treatment for a therapy can be also performed by using the endo-therapy product if necessary.

In the endoscope 3 of this embodiment, the track ball 69 having the function of the articulation instruction input section, the endoscope switches SW1 to SW3 for performing various operation instruction such as the freeze instruction operation, the air water switch (SW4), and the suction switch (SW5) are arranged bilaterally symmetrically to the center line O in the longitudinal direction of the grasping section 68 as shown in FIG. 46.

Therefore, as shown in FIG. 46B, for example, when the surgeon uses the right hand to grasp the grasping section 68 of the operation section 22, the track ball 69 is located at a position easy to be manipulated by the thumb, and the air water switch (SW4) and the suction (SW5) bilaterally symmetrically arranged can be also easily operated.

Also, in the case of the grasping, the endoscope switches SW1 and SW2 are located in the vicinities of the grasping positions for the index finger and the middle finger, and further the endoscope switch SW3 is located in the vicinities of the grasping position for the little finger. Therefore, the surgeon can perform various operations with the satisfactory operability by the grasping right hand.

Then, in the case where the surgeon uses the left hand to grasp, the grasping position for grasping the grasping section 68 on the outer peripheral surface is on a side section side opposite to the side section grasped by the right hand. The positions for the respective fingers with respect to the instruction input sections are the same as those in the case of using the left hand.

That is, when the surgeon uses the left hand to grasp the grasping section 68 of the operation section 22, the track ball 69 is located as the position easy to be operated by the thumb, and the air water switch (SW4) and the suction switch (SW5) arranged so as to be bilaterally symmetric can be also operated.

Also, in the case of the grasping, the endoscope switches SW1 and SW2 are located in the vicinities of the grasping positions for the index finger and the middle finger, and further the endoscope switch SW3 is located in the vicinities of the grasping position for the little finger.

Therefore, the surgeon can perform various operations by the grasping the left hand with the satisfactory operability.

As described above, in this embodiment, as the hook 70 that links both the ends in the longitudinal direction of the grasping section 68 for allowing the grasping hand to pass through the inside. Thus, even when the grasping section 68 is not firmly held, the endoscope 3 can be effectively prevented from dropping due to the weight.

Also, in this embodiment, as shown in FIG. 16, change setting of the function allocation for the endoscope switches SW1 to SW5 can be conducted. Therefore, each surgeon can also perform the endoscopic inspection in the most facilitated manner of the operations by changing and setting the function allocation for the endoscope switches SW1 to SW5.

Figure 49A:
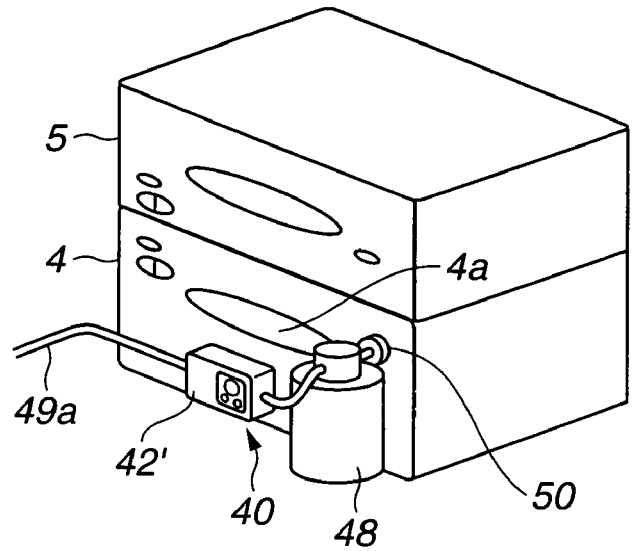
FIG. 49A is a perspective view showing a state in which the detachable AWS adapter is attached to the AWS unit in the endoscopic system according to the seventh embodiment.
Figure 49B:
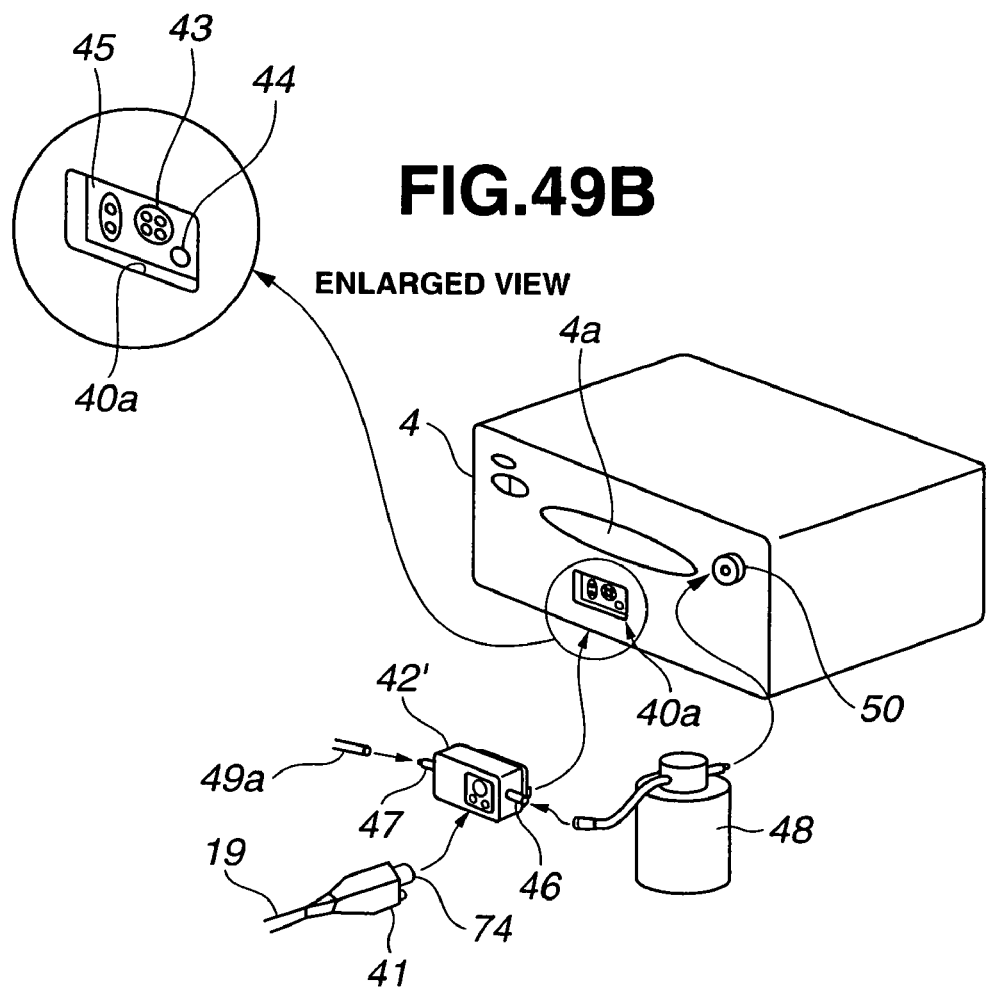
FIG. 49B is a perspective view showing a state in which the detachable AWS adapter is removed from the AWS unit in the endoscopic system according to the seventh embodiment.

It should be noted that in the above-mentioned embodiment, the description has been given of the structure where the pinch valve 45 is provided on the AWS unit 4 side, to which the AWS adapter 42 is connected, but as shown in FIG. 49, an electromagnetic valve unit 42' may be detachably attached to the concave portion 40a of the AWS unit 4 (which is also a modified example of the AWS adaptor). Then, in the state where the electromagnetic valve unit 42' is attached to the AWS unit 4, the endoscope connector 41 of the endoscope 3 is detachably mounted.

It should be noted that FIG. 50A is a front view of the electromagnetic valve unit 42', FIGS. 50B and 50C are left and right side views, and FIGS. 50D and 50E are cross-sectional views taken by the lines A-A' and B-B' of FIG. 50A, respectively.

In the AWS adapter 42, the concave portion 42f accommodating the pinch valve 45 (protruding from the front face of the AWS unit 4) is provided on the back (base end) side, but the electromagnetic valve unit 42' shown in FIG. 50 has the structure in which the pinch valve 45 is provided inside thereof, and the relief duct line 47a penetrates in the pinch valve 45.

Then, in the electromagnetic valve unit 42', a pinch valve connector 42g that is detachably connected to the electromagnetic valve 42' of the AWS unit 4 and transmits the signal for driving the pinch valve 45 is attached to the back side. Other structure is the same as that of the AWS adaptor 42.

The operation effects in the case of adopting the AWS unit 4 and the electromagnetic valve 42' shown in FIGS. 49 and 50 are substantially the same as those in the case of using the AWS unit 4 and the electromagnetic valve unit 42 according to the seventh embodiment.

As described above, according to the seventh embodiment, the transparency sensor is provided in the midway of the duct line. Thus, not only at the time of cleaning and disinfection of the endoscope, but at the time of bedside cleaning conducted immediately after the endoscope use, the contamination on the duct line or the transparency of the fluid passing through the duct line or the like can be detected.

According to the endoscope of the present invention, by inserting the insert section in the body cavity and operating the various operation parts such as the track ball provided to the operation sections, the endoscopic inspection can be conducted under the satisfactory operability.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
    an insert section including a freely bendable bending section;
    an illumination section for emitting illumination light;
    an optical element for splitting the illumination light emitted from the illumination section into transmission light and reflection light, by a light branch section provided at a peripheral portion of the optical element;
    a first light guide member for guiding the reflection light;
    a pressure deformation member arranged at the insert section, into which the reflection light guided by the first light guide member is emitted, the pressure deforming member being deformed in accordance with an amount of pressure exerted from outside;
    a second light guide member for guiding light reflected inside the pressure deformation member;
    a light detection section for detecting quantity of the light guided by the second light guide member; and
    a control section for controlling driving of the bending section based on the quantity of the light detected by the light detection section.

2. The endoscope according to claim 1, wherein the first light guide member guides an illumination light on the periphery side of the illumination light output from the illumination window.

3. The endoscope according to claim 1, wherein the first and second light guide members are each composed of an optical fiber.

4. The endoscope according to claim 1, wherein the pressure deformation member is arranged on an inner side of the bending section and forms a detection section for a bending amount of the bending section.

5. The endoscope according to claim 1, wherein the first light guide member is composed by using a light guide fiber arranged on the peripheral side in a light guide fiber bundle that structures a light guide for outputting an illumination light from the illumination window.

6. The endoscope according to claim 1, wherein the pressure deformation members are arranged at plural positions in a longitudinal direction of the insert section in the peripheral section including the bending section.

7. The endoscope according to claim 1, wherein a plurality of pressure deformation members, each of which comprising the pressure deformation member, are arranged at.

8. The endoscope according to claim 1, wherein the control section determines whether or not the amount of pressure equal to or larger than a predetermined value is effected on the basis of the quantity of the light detected by the light detection section.

9. The endoscope according to claim 1, wherein the control section comprises a regulation section for regulating the driving of the bending section on the basis of the quantity of the light detected by the light detection section.

10. The endoscope according to claim 1, wherein the illumination section is a light emitting diode disposed at a distal end section of the insert section.

11. The endoscope according to claim 1, wherein the pressure from outside is a contact pressure between an inner wall in a body cavity of a subject body and the pressure deformation member.

12. A bending drive control method, comprising:
    a first step of performing bending drive of a bending section in a bending instruction direction in response to a bending instruction, the bending section including an optical element for splitting illumination light emitted from an illumination section into transmission light and reflection light by a light branch section provided at a peripheral portion of the optical element, a pressure deformation member into which the reflection light is emitted, the pressure deformation member being deformed in accordance with an amount of pressure exerted from outside, and a freely bendable bending section;
    a second step of detecting whether or not a change of an amount of light reflected inside the pressure deformation member is equal to or larger than a reference value; and
    a third step of regulating the bending drive when the change of the amount of the reflected light is equal to or larger than the reference value.

* * * * *